US008183263B2

(12) United States Patent
Wang et al.

(10) Patent No.: US 8,183,263 B2
(45) Date of Patent: *May 22, 2012

(54) HETEROARYL SUBSTITUTED THIAZOLES

(75) Inventors: Xiangzhu Wang, Branford, CT (US);
Suoming Zhang, Madison, CT (US);
Venkat Gadhachanda, Hamden, CT (US); Cuixian Liu, Madison, CT (US);
Jesse Quinn, Windsor, CT (US);
Shouming Lee, Cheshire, CT (US);
Dawei Chen, Middletown, CT (US);
Milind Deshpande, Madison, CT (US);
Avinash Phadke, Branford, CT (US)

(73) Assignee: Achillion Pharmaceuticals, Inc., New Haven, CT (US)

( * ) Notice: Subject to any disclaimer, the term of this patent is extended or adjusted under 35 U.S.C. 154(b) by 630 days.

This patent is subject to a terminal disclaimer.

(21) Appl. No.: 12/125,554

(22) Filed: May 22, 2008

(65) Prior Publication Data
US 2009/0041720 A1    Feb. 12, 2009

Related U.S. Application Data

(60) Provisional application No. 60/939,424, filed on May 22, 2007.

(51) Int. Cl.
A01N 43/40       (2006.01)
A61K 31/44       (2006.01)
C07D 417/04      (2006.01)
C07D 417/14      (2006.01)

(52) U.S. Cl. ..................... 514/338; 546/270.4
(58) Field of Classification Search .................. None
See application file for complete search history.

(56) References Cited

U.S. PATENT DOCUMENTS

| | | | |
|---|---|---|---|
| 3,467,666 | A | 9/1969 | Dexter et al. |
| 3,933,838 | A | 1/1976 | Manghisi et al. |
| 5,856,347 | A | 1/1999 | Hashiguchi et al. |
| 6,583,163 | B2 | 6/2003 | Chihiro et al. |
| 7,115,746 | B2 | 10/2006 | Snoonian et al. |
| 7,163,952 | B2 | 1/2007 | Inaba et al. |
| 7,169,931 | B2 | 1/2007 | Takemoto et al. |
| 7,232,838 | B2 | 6/2007 | Love et al. |
| 2002/0016471 | A1 | 2/2002 | Salituro et al. |
| 2004/0110810 | A1 | 6/2004 | Ciulfolini et al. |
| 2004/0186148 | A1 | 9/2004 | Shankar et al. |
| 2004/0254191 | A1 | 12/2004 | Love et al. |
| 2004/0267017 | A1 | 12/2004 | Bierer et al. |
| 2007/0004711 | A1 | 1/2007 | Zhang et al. |
| 2007/0213301 | A1 | 9/2007 | Zhang et al. |
| 2008/0004279 | A1 | 1/2008 | Moussy et al. |

FOREIGN PATENT DOCUMENTS

| | | |
|---|---|---|
| EP | 0154190 A1 | 8/1985 |
| EP | 0790057 B1 | 5/2002 |
| EP | 1321463 B1 | 12/2002 |
| EP | 1354603 A1 | 10/2003 |
| EP | 1599468 B1 | 3/2007 |
| EP | 1525200 B1 | 10/2007 |
| WO | 0006575 A2 | 2/2000 |
| WO | 0033837 A2 | 6/2000 |
| WO | 0121160 A2 | 3/2001 |
| WO | 0153267 A1 | 7/2001 |
| WO | 0164674 A1 | 9/2001 |
| WO | 0174793 A2 | 10/2001 |
| WO | 02051410 A2 | 7/2002 |
| WO | 03015773 A2 | 2/2003 |
| WO | 03027085 A2 | 4/2003 |
| WO | 03028729 A2 | 4/2003 |
| WO | 03066215 A1 | 8/2003 |
| WO | 03048140 A1 | 12/2003 |
| WO | 2004071447 A2 | 8/2004 |
| WO | 2004076693 A1 | 9/2004 |
| WO | 2004085385 A2 | 10/2004 |

(Continued)

OTHER PUBLICATIONS

Bhoga, et. al., European Journal of Medicinal Chemistry (2007), 42(8), 1144-1150.*
Bhoga, U., "Novel synthetic approach to N-aryl-4-(3-pyridyl)thiazol-2-amino and analogues sing HMCM-41 as catalyst, and their biological evaluation as human platelet aggregation inhibitors," Eur. J. Med. Chem. (2007) 42: 1144-1150.
Kuleshova, L.N. et al., "Conformational Polymorphism of N-(4-Butoxyphenyl)-4-(4'-Nitrophenyl)-2-Thiazolamine," Crystallography Reports, (2003) 49(5): 798-806.
Parvate, J.A. "Synthesis of substituted 4,2'-bis thiazoles," Indian Drugs (1989) 26(5): 222-226.
Pathak, V. N. "Synthesis and Biological Activities of Some New 2-(N-arylamino)-4-(fluoroaryl) thiazoles," Journal of the Indian Chemical Society (1979) 56(10): 1010-1012. (Abstract Only).

(Continued)

Primary Examiner — Jeffrey Murray
(74) Attorney, Agent, or Firm — Cantor Colburn LLP

(57) ABSTRACT

The invention provides heteroaryl substituted thiazolo compounds of Formula I and II

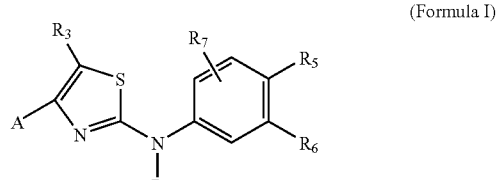
(Formula I)

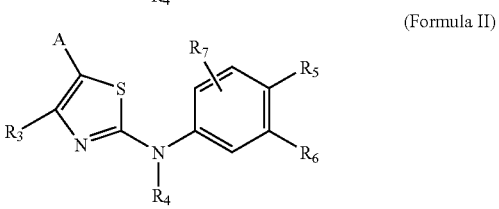

(Formula II)

and pharmaceutically acceptable salts thereof. The variables A and $R_3$ to $R_7$ are defined herein. The invention also includes methods for preparing compounds and salts of Formula I and II. The present invention also includes pharmaceutical compositions containing heteroaryl substituted thiazolo compounds and methods for using heteroaryl substituted thiazolo compounds, including methods for using the compounds in the treatment of hepatitis C virus.

25 Claims, No Drawings

FOREIGN PATENT DOCUMENTS

| | | |
|---|---|---|
| WO | 2004092145 A1 | 10/2004 |
| WO | 2004096225 A2 | 11/2004 |
| WO | 2004098612 A2 | 11/2004 |
| WO | 2004110350 A2 | 12/2004 |
| WO | 2005007647 A1 | 1/2005 |
| WO | 2005016323 A2 | 2/2005 |
| WO | 2005051318 A2 | 6/2005 |
| WO | 2005058887 A2 | 6/2005 |
| WO | 2005073225 A1 | 8/2005 |
| WO | 2005077368 A2 | 8/2005 |
| WO | 2005082089 A2 | 9/2005 |
| WO | 2005099673 A1 | 10/2005 |
| WO | 2005102318 A1 | 11/2005 |
| WO | 2005102325 A1 | 11/2005 |
| WO | 2005102326 A2 | 11/2005 |
| WO | 2005102346 A2 | 11/2005 |
| WO | 2005102455 A1 | 11/2005 |
| WO | 2005112920 A1 | 12/2005 |
| WO | 2005115304 A2 | 12/2005 |
| WO | 2005115385 A1 | 12/2005 |
| WO | 2006028029 A1 | 3/2006 |
| WO | 2006033005 A2 | 3/2006 |
| WO | 2006113261 A2 | 10/2006 |
| WO | 2006122011 A2 | 11/2006 |
| WO | 2006122250 A2 | 11/2006 |
| WO | WO2006122011 * | 11/2006 |
| WO | 2007026251 A2 | 3/2007 |
| WO | 2007065939 A1 | 6/2007 |
| WO | 03062215 A1 | 7/2007 |
| WO | 2007088996 A1 | 8/2007 |
| WO | 2007089743 A2 | 8/2007 |
| WO | 2007095603 A2 | 8/2007 |
| WO | 2007103550 A2 | 9/2007 |
| WO | 2008033932 A2 | 3/2008 |

OTHER PUBLICATIONS

Shipps, G. W. et al. "Aminothiazole Inhibitors of HVC RNA Polymerase," Bioorganic & Medicinal Chemistry Letters (2005) 15(1): 115-119.

Truce, W.E., et al. "The Stereochemistry of the Reaction of Tetrachloroethylene with p-toluene-thiolate reagent," Tetrahedron 21: 2899-2905 (1965).

International Search Report for PCT/US2006/017692 dated Jan. 19, 2007.

International Search Report for PCT/US2007/006023 dated Aug. 21, 2007.

International Search Report for PCT/US2008/006676 dated Jul. 30, 2009.

Written Opinion for PCT/US2006/017692 dated Jan. 19, 2007.

Written Opinion for PCT/US2007/006023 dated Aug. 21, 2007.

* cited by examiner

HETEROARYL SUBSTITUTED THIAZOLES

CROSS REFERENCE TO RELATED APPLICATION

This application claims priority from U.S. Provisional Application No. 60/939,424 filed May 22, 2007, which is hereby incorporated by reference in its entirety.

FIELD OF THE INVENTION

The present invention provides heteroaryl substituted thiazolo compounds. The invention also includes methods for preparing such compounds. The present invention further includes pharmaceutical compositions containing heteroaryl substituted thiazolo compounds and methods for using such compounds, including methods for using the compounds to treat hepatitis C infection.

BACKGROUND

An estimated 3% of the world's population is infected with the hepatitis C virus. Of those exposed to HCV, 80% become chronically infected, at least 30% develop cirrhosis of the liver and 1-4% develop hepatocellular carcinoma. Hepatitis C Virus (HCV) is one of the most prevalent causes of chronic liver disease in the United States, reportedly accounting for about 15 percent of acute viral hepatitis, 60 to 70 percent of chronic hepatitis, and up to 50 percent of cirrhosis, end-stage liver disease, and liver cancer. Chronic HCV infection is the most common cause of liver transplantation in the U.S., Australia, and most of Europe. Hepatitis C causes an estimated 10,000 to 12,000 deaths annually in the United States. While the acute phase of HCV infection is usually associated with mild symptoms, some evidence suggests that only about 15% to 20% of infected people will clear HCV.

HCV is an enveloped, single-stranded RNA virus that contains a positive-stranded genome of about 9.6 kb. HCV is classified as a member of the Hepacivirus genus of the family Flaviviridae. At least 4 strains of HCV, GT-1-GT-4, have been characterized.

The HCV lifecycle includes entry into host cells; translation of the HCV genome, polyprotein processing, and replicase complex assembly; RNA replication, and virion assembly and release. Translation of the HCV RNA genome yields a more than 3000 amino acid long polyprotein that is processed by at least two cellular and two viral proteases. The HCV polyprotein is:

NH2-C-E1-E2-p7-NS2-NS3-NS4A-NS4B-NS5A-NS5B-COOH.

The cellular signal peptidase and signal peptide peptidase have been reported to be responsible for cleavage of the N-terminal third of the polyprotein (C-E1-E2-p7) from the nonstructural proteins (NS2-NS3-NS4A-NS4B-NS5A-NS5B). The NS2-NS3 protease mediates a first cis cleavage at the NS2-NS3 site. The NS3-NS4A protease then mediates a second cis-cleavage at the NS3-NS4A junction. The NS3-NS4A complex then cleaves at three downstream sites to separate the remaining nonstructural proteins. Accurate processing of the polyprotein is asserted to be essential for forming an active HCV replicase complex.

Once the polyprotein has been cleaved, the replicase complex comprising at least the NS3-NS5B nonstructural proteins assembles. The replicase complex is cytoplasmic and membrane-associated. Major enzymatic activities in the replicase complex include serine protease activity and NTPase helicase activity in NS3, and RNA-dependent RNA polymerase activity of NS5B. In the RNA replication process, a complementary negative strand copy of the genomic RNA is produced. The negative strand copy is used as a template to synthesize additional positive strand genomic RNAs that may participate in translation, replication, packaging, or any combination thereof to produce progeny virus. Assembly of a functional replicase complex has been described as a component of the HCV replication mechanism. Provisional application 60/669,872 "Pharmaceutical Compositions and Methods of Inhibiting HCV Replication" filed Apr. 11, 2005, is hereby incorporated by reference in its entirety for its disclosure related to assembly of the replicase complex.

Current treatment of hepatitis C infection typically includes administration of an interferon, such as pegylated interferon (IFN), in combination with ribavirin. The success of current therapies as measured by sustained virologic response (SVR) depends on the strain of HCV with which the patient is infected and the patient's adherence to the treatment regimen. Only 50% of patients infected with HCV strain GT-1 exhibit a sustained virological response. Direct acting antiviral agents such as ACH-806, VX-950 and NM 283 (prodrug of NM 107) are in clinical development for treatment of chronic HCV. Due to lack of effective therapies for treatment for certain HCV strains and the high mutation rate of HCV, new therapies are needed. The present invention fulfills this need and provides additional advantages, which are described herein.

SUMMARY OF THE INVENTION

Compounds useful for treating and preventing hepatitis C infections, pharmaceutical compositions, and methods for use of such compounds are provided herein.

In one aspect, the present invention includes compounds of Formula I and II and pharmaceutically acceptable salts thereof.

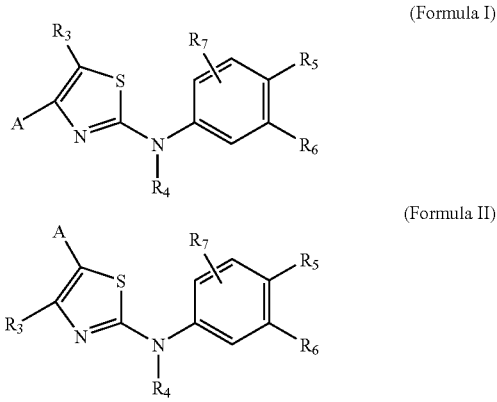

Within Formula I and II the variables A, $R_3$, $R_4$, $R_5$, $R_6$, and $R_7$ carry the definitions set forth below.

A is a mono- or -bicyclic group of the formula:

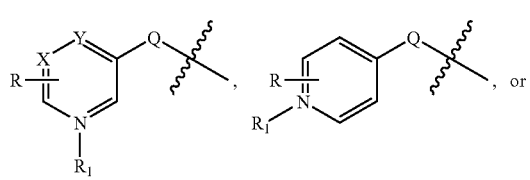

-continued

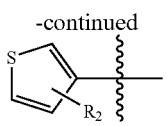

where Q is O, S, N, $CH_2$, or absent; and X is N or CH; Y is N or CH; and not more that 1 of X and Y are N.

R represents 0 or 1 or more substituents independently chosen from
  (a) hydroxyl, halogen, amino, cyano, —COOH, —$CONH_2$, —$PO_4$, $C_1$-$C_2$haloalkyl, and $C_1$-$C_2$haloalkoxy; and
  (b) $C_1$-$C_4$alkyl, $C_1$-$C_4$alkoxy, mono- and di-$C_1$-$C_4$alkylamino, $C_2$-$C_4$alkanoyl, mono- and di-$C_1$-$C_4$alkylphosphate, and $C_1$-$C_4$alkylester, each of which is substituted with 0 or 1 or more substituents independently chosen from halogen, hydroxyl, amino, cyano, $C_1$-$C_2$alkoxy, and mono- and di-$C_1$-$C_2$alkylamino.

Or, any two R groups, covalently bound to adjacent atoms, may be joined to form a 5-membered heterocyclic group containing 1 or 2 additional heteroatoms independently chosen from N, O, and S, wherein the 5-membered heterocyclic group is optionally substituted.

$R_1$ is absent, oxygen, or $C_1$-$C_4$alkyl.

Or, R and $R_1$ may be joined to form a 5-membered heterocyclic group containing 1 or 2 additional heteroatoms independently chosen from N, O, and S, wherein the 5-membered heterocyclic group is optionally substituted, when R and $R_1$ are bound to adjacent carbon atoms.

$R_2$ is 0 or 1 or more substituents independently chosen from
  (a) hydroxyl, halogen, amino, cyano, —COOH, —$CONH_2$, —$PO_4$, $C_1$-$C_2$haloalkyl, and $C_1$-$C_2$haloalkoxy;
  (b) $C_1$-$C_4$alkyl, $C_1$-$C_4$alkoxy, mono- and di-$C_1$-$C_4$alkylamino, $C_2$-$C_4$alkanoyl, $C_1$-$C_4$alkylphosphate, and $C_1$-$C_4$alkylester, each of which is substituted with 0 or 1 or more substituents independently chosen from halogen, hydroxyl, amino, cyano, $C_1$-$C_2$alkoxy, mono- and di-$C_1$-$C_2$alkylamino.

$R_3$ is hydrogen, halogen, hydroxyl, amino, cyano, $C_1$-$C_2$alkyl, or (mono- or di-$C_1$-$C_2$alkylamino)$C_0$-$C_2$alkyl.

$R_4$ is hydrogen, amino, or $R_4$ is $C_1$-$C_6$alkyl, $C_2$-$C_6$alkenyl, mono- or di-$C_1$-$C_6$alkylamino, or $C_2$-$C_6$alkenylamino, each of which alkyl or alkenyl chain contains 0 or 1 to 4 oxygen atoms and each of which is substituted with 0 or 1 or more of amino, hydroxyl, —COOH, $C_1$-$C_4$alkoxy, mono- and di-$C_1$-$C_4$alkylamino, mono- and di-$C_1$-$C_4$alkylcarboxamide, and $C_1$-$C_4$alkylester.

$R_5$ and $R_6$ are L and M, where one of $R_5$ and $R_6$ is L and the other is M, or wherein:

L is hydrogen, halogen, hydroxyl, amino, cyano, —COOH, —$CONH_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and M is $C_2$-$C_{20}$carbohydryl, $C_2$-$C_{20}$carbohydryloxy, $C_2$-$C_{20}$alkanoyl, mono- or di-$C_2$-$C_{20}$alkylamino, where each carbohydryl, carbohydryloxy, alkanoyl, or alkylamino chain may contain one or more oxygen atoms, nitrogen atoms, sulfur atoms, or sulfonyl groups and may be substituted with one or more halogen, hydroxyl, cyano, amino, $C_1$-$C_2$haloalkyl, $C_1$-$C_2$haloalkoxy, and oxo, and may also be substituted with one aryl, mono- or bicyclic heteroaryl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy.

Or, M is mono- or bicyclic carbocycloxy, or 5- or 6-membered heteroaryloxy, each of which contains 0, 1, or 2 heteroatoms chosen from N, O, and S and is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy.

Or, $R_5$ and $R_6$ are taken together to form a 5- or 6-membered carbocyclic or heterocyclic ring, which is saturated, partially unsaturated, or aromatic, and is substituted with 0, 1, or 2 substituents independently chosen from halogen, hydroxyl, amino, cyano, $C_1$-$C_{10}$alkyl, $C_2$-$C_{10}$alkenyl, $C_1$-$C_{10}$alkoxy, and optionally substituted (phenyl)$C_0$-$C_4$alkyl.

$R_7$ is 0 or 1 or more substituents independently chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy.

The invention includes pharmaceutical compositions comprising a compound of the invention or a salt thereof, containing at least one pharmaceutically acceptable carrier. The invention also includes pharmaceutical compositions comprising a compound of the invention and containing at least one additional active agent. The invention includes packaged pharmaceutical compositions comprising a compound of the invention in a container and further comprising instructions for using the composition to treat a patient infected with a hepatitis C virus or susceptible to infection with a hepatitis C virus.

In another aspect the invention provides a method for treating or preventing hepatitis C infection comprising providing an effective amount of a compound or salt of the invention to a patient in need of such treatment or prevention.

A method of inhibiting HCV replication in vivo comprising administering to a patient infected with HCV a concentration of a compound or salt of the invention sufficient to inhibit HCV replicon replication in vitro is also included in the invention.

These and other aspects of the invention will be more clearly understood with reference to the following detailed description, examples and claims.

DETAILED DESCRIPTION OF THE INVENTION

Terminology

Prior to setting forth the invention in detail, it may be helpful to provide definitions of certain terms to be used herein. Compounds of the present invention are described using standard nomenclature. Unless defined otherwise, all technical and scientific terms used herein have the same meaning as is commonly understood by one of skill in the art to which this invention belongs.

Formula I and II include all subformulae thereof. For example Formula I includes compounds of Formulas III to V and the pharmaceutically acceptable salts, prodrugs and other derivatives, hydrates, and polymorphs, thereof.

The terms "a" and "an" do not denote a limitation of quantity, but rather denote the presence of at least one of the referenced items. The term "or" means "and/or". The terms "comprising", "having", "including", and "containing" are to be construed as open-ended terms (i.e., meaning "including, but not limited to"). Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this invention belongs.

An "active agent" means a compound (including a compound of the invention), element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound, crystalline forms, non-crystalline forms, and any polymorphs of the compound are included. Compounds may contain one or more asymmetric elements such as stereogenic centers, stereogenic axes and the like, e.g., asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, all optical isomers in pure form and mixtures thereof are encompassed. In addition, compounds with carbon-carbon double bonds may occur in Z- and E-forms, with all isomeric forms of the compounds. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column. All forms are contemplated herein regardless of the methods used to obtain them.

All forms (for example solvates, optical isomers, enantiomeric forms, polymorphs, free compound and salts) of an active agent may be employed either alone or in combination.

In certain situations, the compounds of the invention may contain one or more asymmetric elements such as stereogenic centers, including chiral centers, stereogenic axes and the like, e.g. asymmetric carbon atoms, so that the compounds can exist in different stereoisomeric forms. These compounds can be, for example, racemates or optically active forms. For compounds with two or more asymmetric elements, these compounds can additionally be mixtures of diastereomers. For compounds having asymmetric centers, it should be understood that all of the optical isomers and mixtures thereof are encompassed. In addition, compounds with carbon-carbon double bonds may occur in Z- and E-forms, with all isomeric forms of the compounds being included in the present invention. Formula I and II include all chiral forms, stereoisomers, diastereomers, and enantiomers of compounds of Formula I and II.

The term "chiral" refers to molecules, which have the property of non-superimposability of the mirror image partner.

"Stereoisomers" are compounds, which have identical chemical constitution, but differ with regard to the arrangement of the atoms or groups in space.

A "Diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example a chiral HPLC column.

"Enantiomers" refer to two stereoisomers of a compound, which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Where a compound exists in various tautomeric forms, the invention is not limited to any one of the specific tautomers, but rather includes all tautomeric forms.

The invention includes compounds of the invention having all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. A, $R_3$, $R_4$, $R_5$, $R_6$, and $R_7$. Unless otherwise specified, each variable within the invention is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds.

The term "substituted", as used herein, means that any one or more hydrogens on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —(CH$_2$)C$_3$-C$_7$cycloalkyl is attached through carbon of the methylene (CH$_2$) group.

"Alkyl" includes both branched and straight chain saturated aliphatic hydrocarbon groups, having the specified number of carbon atoms, generally from 1 to about 12 carbon atoms. The term C$_1$-C$_6$alkyl as used herein indicates an alkyl group having from 1 to about 6 carbon atoms. When C$_0$-C$_n$ alkyl is used herein in conjunction with another group, for example, (phenyl)C$_0$-C$_4$ alkyl, the indicated group, in this case phenyl, is either directly bound by a single covalent bond (C$_0$), or attached by an alkyl chain having the specified number of carbon atoms, in this case from 1 to about 4 carbon atoms. Examples of alkyl include, but are not limited to, methyl, ethyl, n-propyl, isopropyl, n-butyl, 3-methylbutyl, t-butyl, n-pentyl, and sec-pentyl.

"Alkanoyl" is an alkyl group as defined above, attached through a keto (—(C=O)—) bridge. Alkanoyl groups have the indicated number of carbon atoms, with the carbon of the keto group being included in the numbered carbon atoms. For example a C$_2$alkanoyl group is an acetyl group having the formula CH$_3$(C=O)—.

"Alkenyl" means straight and branched hydrocarbon chains comprising one or more unsaturated carbon-carbon bonds, which may occur in any stable point along the chain. Alkenyl groups described herein typically have from 2 to about 12 carbons atoms. Preferred alkenyl groups are lower alkenyl groups, those alkenyl groups having from 2 to about 8 carbon atoms, e.g. C$_2$-C$_8$, C$_2$-C$_6$, and C$_2$-C$_4$ alkenyl groups. Examples of alkenyl groups include ethenyl, propenyl, and butenyl groups.

"Alkoxy" means an alkyl group, as defined above, with the indicated number of carbon atoms attached via an oxygen bridge. Examples of alkoxy include, but are not limited to, methoxy, ethoxy, 3-hexoxy, and 3-methylpentoxy.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. The alkyl groups are independently chosen. Examples of mono- and di-alkylamino groups include ethylamino, dimethylamino, and methyl-propyl-amino. "Mono- and/or dialkylaminoalkyl" groups are mono- and/or di-alkylamino groups attached through an alkyl linker having the specified number of carbon atoms, for example a di-methylaminoethyl group. Tertiary amino substituents may by designated by nomenclature of the form N—R—N—R', indicating that the groups R and R' are both attached to a single nitrogen atom.

"Alkylester" indicates an alkyl group as defined above attached through an ester linkage. The ester linkage may be in either orientation, e.g. a group of the formula —O(C=O) alkyl or a group of the formula —(C=O)Oalkyl.

"Alkylphosphate" indicates a phosphoester linkage which is mono- or di-substituted with independently chosen alkyl groups. A mono-alkyl phosphate substituent has the formula alkyl-HPO$_4$- and a di-alkyl phosphate has the formula alkyl$_1$alkyl$_2$PO$_4$-and the structure

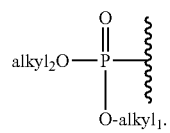

The alkyl groups are as defined above.

"Aryl" means aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and bi-phenyl.

"Mono- and/or di-alkylcarboxamide" indicates groups of formula (alkyl$_1$)-NH—(C=O)— and (alkyl$_1$)(alkyl$_2$)—N—(C=O)— in which the alkyl1 and alkyl2 groups are independently chosen alkyl groups as defined above having the indicated number of carbon atoms. Mono and/or di-alkylcarboxamide also refers to groups of the formula —NH(C=O)(alkyl$_1$) and —N(alkyl$_2$)(C=O)(alkyl$_1$), carboxamide groups in which the point of attachment is the nitrogen atom, in which the alkyl$_1$ and alkyl$_2$ groups are independently chosen alkyl groups as defined above having the indicated number of carbon atoms.

"Alkylsulfonyl" means alkyl-(SO$_2$)—, where the alkyl group is an alkyl group as defined above having the defined number of carbon atoms. An exemplary alkylsulfonyl group is methylsulfonyl.

"Carbohydryl" as used herein, includes both branched and straight-chain hydrocarbon groups, which are saturated or unsaturated, having the specified number of carbon atoms. Examples of carbohydryl groups include C$_1$-C$_6$alkyl, such as methyl, or 5-butyl, C$_2$-C$_6$alkynyl such as hexynyl, and C$_2$-C$_6$ alkenyl, such as 1-propenyl.

"Carbohydryloxy" indicates a carbohydryl group, as defined above, attached through an oxygen bridge.

"Cycloalkyl" indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane.

"Mono- or bicyclic carbocycloxy" is a group that contains a mono-cyclic carbocyclic group or a bicyclic carbocylic group having two fused carbocyclic rings which mono- or bi-cyclic carbocyclic group is attached via an oxygen linker. The ring(s) of a mono- or bi-cyclic carbocyclic group may be saturated (cycloalkyl), partially saturated, or aromatic. Typically, a carbocyclic ring comprises contains from 3 to 8 ring members or is some embodiments 5 to 7 ring members.

"Mono- or bicyclic heteroaryl" indicates a stable 5- to 7-membered monocyclic or 7- to 10-membered bicyclic heterocyclic ring which contains at least 1 aromatic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Heteroaryloxy" is a heteroaryl group as defined above, attached via an oxygen bridge.

"Heterocycloalkyl" means a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

"Haloalkyl" indicates both branched and straight-chain alkyl groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge (oxygen of an alcohol radical).

"Halo" or "halogen" as used herein refers to fluoro, chloro, bromo, or iodo.

"Sulfonyl" is used herein to indicate an —$SO_2$— linker.

"Pharmaceutical compositions" are compositions comprising at least one active agent, such as a compound or salt of the invention, and at least one other substance, such as a carrier, excipient, or diluent. Pharmaceutical compositions meet the U.S. FDA's GMP (good manufacturing practice) standards for human or non-human drugs.

"Pharmaceutically acceptable salts" includes derivatives of the disclosed compounds in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions of the invention refers to a diluent, excipient, or vehicle with which an active compound is administered.

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the present application includes both one and more than one such excipient.

A "patient" is a human or non-human animal in need of medical treatment. Medical treatment can include treatment of an existing condition, such as a disease or disorder, prophylactic or preventative treatment, or diagnostic treatment. In some embodiments the patient is a human patient.

"Prodrug" means any compound that becomes compound of the invention when administered to a mammalian subject, e.g., upon metabolic processing of the prodrug. Examples of prodrugs include, but are not limited to, acetate, formate and benzoate and like derivatives of functional groups (such as alcohol or amine groups) in the compounds of the invention.

"Providing" means giving, administering, selling, distributing, transferring (for profit or not), manufacturing, compounding, or dispensing.

"Providing a compound of the invention with at least one additional active agent" means the compound of the invention and the additional active agent(s) are provided simultaneously in a single dosage form, provided concomitantly in separate dosage forms, or provided in separate dosage forms for administration separated by some amount of time that is within the time in which both the compound of the invention and the at least one additional active agent are within the blood stream of a patient. The compound of the invention and the additional active agent need not be prescribed for a patient by the same medical care worker. The additional active agent or agents need not require a prescription. Administration of the compound of the invention or the at least one additional active agent can occur via any appropriate route, for example, oral tablets, oral capsules, oral liquids, inhalation, injection, suppositories or topical contact.

"Treatment," as used herein includes providing a compound of the invention and at least one additional active agent sufficient to: (a) prevent a disease or a symptom of a disease from occurring in a patient who may be predisposed to the disease but has not yet been diagnosed as having it (e.g. including diseases that may be associated with or caused by a primary disease as in liver fibrosis that can result in the context of chronic HCV infection); (b) inhibiting the disease, i.e. arresting its development; and (c) relieving the disease, i.e., causing regression of the disease. "Treating" and "treatment" also means providing a therapeutically effective amount of a compound of the invention and at least one additional active agent to a patient having or susceptible to a hepatitis C infection.

A "therapeutically effective amount" of a pharmaceutical combination of this invention means an amount effective, when administered to a patient, to provide a therapeutic benefit such as an amelioration of symptoms, e.g., an amount effective to decrease the symptoms of a hepatitis C infection. For example a patient infected with a hepatitis C virus may present elevated levels of certain liver enzymes, including AST and ALT. Normal levels of AST are from 5 to 40 units per liter of serum (the liquid part of the blood) and normal levels of ALT are from 7 to 56 units per liter of serum. A therapeutically effect amount is thus an amount sufficient to provide a significant reduction in elevated AST and ALT levels or an amount sufficient to provide a return of AST and ALT levels to the normal range. A therapeutically effective amount is also an amount sufficient to prevent a significant increase or significantly reduce the detectable level of virus or viral antibodies in the patient's blood, serum, or tissues. One method of determining treatment efficacy includes measuring HCV RNA levels by a convention method for determining viral RNA levels such as the Roch TaqMan assay. In certain preferred embodiments treatment reduces HCV RNA levels below the limit of quantitation (30 IU/mL, as measured by the Roche TaqMan(R) assay) or more preferably below the limit of detection (10 IU/mL, Roche TaqMan).

A significant increase or reduction in the detectable level of virus or viral antibodies is any detectable change that is statistically significant in a standard parametric test of statistical significance such as Student's T-test, where $p<0.05$.

Antiviral Compounds

The invention includes compounds of Formula I and II, as discussed above. Additionally the invention includes, as alternate embodiments, compound and salts of Formula I and II

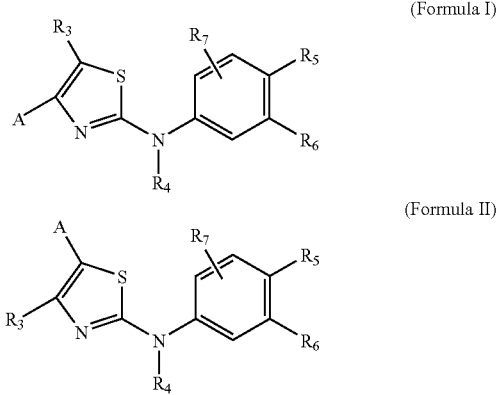

(Formula I)

(Formula II)

in which the variables A and $R_3$-$R_7$ carry any of the values set forth below.

The inventions includes compounds of Formula I and II as described in the Summary of Invention section, wherein the compound is not:

N-(3-(trifluoromethyl)-4-(pentyloxy)phenyl)-4-(pyridin-3-yl)thiazol-2-amine;
4-(6-((dimethylamino)methyl)pyridin-3-yl)-N-(4-(pentyloxy)-3-(trifluoromethyl)phenyl)thiazol-2-amine;
N-(3-fluoro-4-(pentyloxy)phenyl)-4-(pyridin-3-yl)thiazol-2-amine;
N-(4-((piperidin-1-yl)methyl)phenyl)-4-(pyridin-3-yl)thiazol-2-amine;
N-(3-(2,3-dihydro-1H-inden-2-yloxy)phenyl)-4-(pyridin-3-yl)thiazol-2-amine;
N-(4-(cyclohexylmethoxy)-3-fluorophenyl)-4-(pyridin-3-yl)thiazol-2-amine;
5-(4-(pyridin-3-yl)thiazol-2-ylamino)-2-(heptyloxy)benzonitrile;
N-(3-methyl-4-(pentyloxy)phenyl)-4-(pyridin-3-yl)thiazol-2-amine;
N-(4-butoxy-3-(trifluoromethyl)phenyl)-4-(pyridin-3-yl)thiazol-2-amine;
N-(4-(pentyloxy)phenyl)-4-(pyridin-3-yl)thiazol-2-amine;
N-(4-pentylphenyl)-4-(pyridin-3-yl)thiazol-2-amine;
N-(3-(benzyloxy)phenyl)-4-(pyridin-3-yl)thiazol-2-amine;
N-(3-phenoxyphenyl)-4-(pyridin-3-yl)thiazol-2-amine;
N-(3-(phenethyloxy)phenyl)-4-(pyridin-3-yl)thiazol-2-amine;
N-(4-(hexyloxy)phenyl)-4-(pyridin-3-yl)thiazol-2-amine;
N-(4-butoxyphenyl)-4-(pyridin-3-yl)thiazol-2-amine;
N-(4-(heptyloxy)phenyl)-4-(pyridin-3-yl)thiazol-2-amine;
N-(4-(octyloxy)phenyl)-4-(pyridin-3-yl)thiazol-2-amine;
N-(4-hexylphenyl)-4-(pyridin-3-yl)thiazol-2-amine;
N-(4-octylphenyl)-4-(pyridin-3-yl)thiazol-2-amine;
N-(4-butylphenyl)-4-(pyridin-3-yl)thiazol-2-amine;
N-(3-benzylphenyl)-4-(pyridin-3-yl)thiazol-2-amine;
2-(4-(4-(pyridin-3-yl)thiazol-2-ylamino)phenyl)acetonitrile;
N1-isopropyl-N1-phenyl-N4-(4-(pyridin-3-yl)thiazol-2-yl)benzene-1,4-diamine;
butyl 4-(4-(pyridin-3-yl)thiazol-2-ylamino)benzoate;
ethyl 2-(4-(4-(pyridin-3-yl)thiazol-2-ylamino)phenyl)acetate;
N-(4-propylphenyl)-4-(pyridin-3-yl)thiazol-2-amine;
N-(4-phenoxyphenyl)-4-(pyridin-3-yl)thiazol-2-amine;
N-(3-(trifluoromethyl)-4-(pentyloxy)phenyl)-4-(6-methylpyridin-3-yl)thiazol-2-amine;
N-(3-(trifluoromethyl)-4-(pentyloxy)phenyl)-4-(pyrazin-2-yl)thiazol-2-amine; or
N-(3-(trifluoromethyl)-4-(pentyloxy)phenyl)-N-methyl-4-(pyridin-3-yl)thiazol-2-amine.

The invention further includes a compound of Formula I or Formula II, as defined in the Summary of Invention section, wherein one or more of the following conditions (i) to (ix) is met.

(i) $R_3$ is fluoro;
(ii) $R_3$ is amino, $C_1$-$C_2$alkyl, or (mono- or di-$C_1$-$C_2$alkylamino)$C_0$-$C_2$alkyl;
(iii) $R_5$ is $C_6$-$C_{20}$carbohydryl, $C_6$-$C_{20}$carbohydryloxy, $C_2$-$C_{20}$alkanoyl, or $C_6$-$C_{20}$mono- or di-alkylamino, where the carbohydryl, carbohydryloxy, alkanoyl or mono- or di-alkylamino chain may be substituted with one or more halogen, hydroxyl, cyano, amino, $C_1$-$C_2$haloalkyl, $C_1$-$C_2$haloalkoxy, and oxo, and
    $R_6$ is halogen, hydroxyl, amino, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;
(iv) $R_6$ is $C_4$-$C_{20}$carbohydryl, $C_4$-$C_{20}$carbohydryloxy, or $C_2$-$C_{20}$alkanoyl, where the carbohydryl, carbohydryloxy, or alkanoyl chain may be substituted with one or more substituents independently chosen from halogen, hydroxyl, cyano, amino, $C_1$-$C_2$haloalkyl, $C_1$-$C_2$haloalkoxy, and oxo, and
    $R_5$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;
(v) one of $R_5$ and $R_6$ is $C_4$-$C_{20}$carbohydryl, $C_4$-$C_{20}$carbohydryloxy, or $C_2$-$C_{20}$alkanoyl, where the carbohydryl, carbohydryloxy, or alkanoyl chain contains one or more oxygen atoms, nitrogen atoms, sulfur atoms, or sulfonyl groups and may be substituted with one or more independently chosen halogen, hydroxyl, cyano, amino, $C_1$-$C_2$haloalkyl, $C_1$-$C_2$haloalkoxy, and oxo, and the other of $R_5$ and $R_6$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;

(vi) one of $R_5$ and $R_6$ is a group of the formula —O(CH$_2$)$_2$O—, or $C_4$-$C_{20}$carbohydryl, $C_4$-$C_{20}$carbohydryloxy, or $C_4$-$C_{10}$alkanoyl, where the carbohydryl, carbohydryloxy, or alkanoyl chain may contain one or more oxygen atoms, nitrogen atoms, sulfur atoms, or sulfonyl groups and may be substituted with one or more independently chosen halogen, hydroxyl, cyano, amino, $C_1$-$C_2$haloalkyl, $C_1$-$C_2$haloalkoxy, and oxo, and where the group of the formula —O(CH$_2$)$_2$O—, or the $C_4$-$C_{10}$-carbohydryl, $C_4$-$C_{10}$-carbohydryloxy, or $C_4$-$C_{10}$alkanoyl is substituted with one aryl, mono- or bicyclic heteroaryl, $C_3$-$C_7$cycloalkyl, or 5- to 7-membered heterocycloalkyl, each of which is substituted with 0 or 1 or more substituents independently chosen from halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy; and the other of $R_5$ and $R_6$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;

(vii) one of $R_5$ and $R_6$ is phenoxy, benzyloxy, or indanyloxy; each of which is substituted with 0 or 1 or more independently chosen halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy;

(viii) one of $R_5$ and $R_6$ is ($C_3$-$C_7$cycloalkyl)$C_0$-$C_2$alkyl or ($C_3$-$C_7$cycloalkyl)$C_0$-$C_2$alkoxy and the other of $R_5$ and $R_6$ is hydrogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and (ix) $R_5$ and $R_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, hydroxyl, amino, cyano, $C_1$-$C_{10}$alkyl, $C_2$-$C_{10}$alkenyl, $C_1$-$C_{10}$alkoxy, and optionally substituted (phenyl)$C_0$-$C_4$alkyl.

The A, R, and $R_1$ Variables

The invention includes embodiments in which compounds the variables A, R, and $R_1$, in Formula I and Formula II carries any of the following definitions.

(1) $R_1$ is hydrogen.

(2) A is a group of the formula:

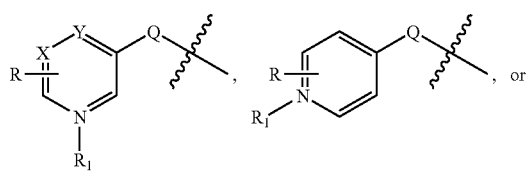

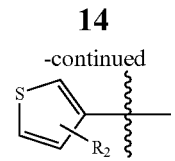

where Q is O, S, N, CH$_2$, or absent; and X is N or CH; Y is N or CH; and not more that 1 of X and Y are N, wherein R is hydrogen, and R and $R_2$ may carry any of the definitions set forth herein for these variables.

(3) A is

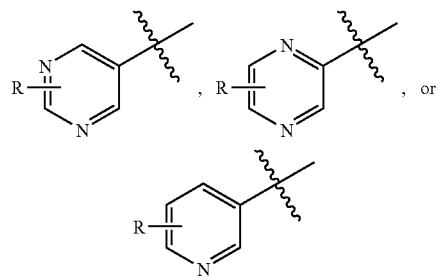

in which

R represents 0 or 1 or more substituents independently chosen from (a) hydroxyl, halogen, amino, cyano, —COOH, —CONH$_2$, —PO$_4$, $C_1$-$C_2$haloalkyl, and $C_1$-$C_2$haloalkoxy; and (b) $C_1$-$C_4$alkyl, $C_1$-$C_4$alkoxy, mono- and di-$C_1$-$C_4$alkylamino, $C_2$-$C_4$alkanoyl, mono- and di-$C_1$-$C_4$alkylphosphate, and $C_1$-$C_4$alkylester, each of which is substituted with 0 or 1 or more substituents independently chosen from halogen, hydroxyl, amino, cyano, $C_1$-$C_2$alkoxy, mono- and di-$C_1$-$C_2$alkylamino.

(4) A is 3-pyridyl substituted with 0 or 1 substituents R, where R carries any of the definitions set forth herein.

(5) R is 0, 1, or 2 substituents independently chosen from hydroxyl, halogen, amino, cyano, —COOH, —CONH$_2$, —PO$_4$, $C_1$-$C_2$haloalkyl, $C_1$-$C_2$haloalkoxy, $C_1$-$C_4$alkyl, $C_1$-$C_4$alkoxy, mono- and di-$C_1$-$C_4$alkylamino, $C_2$-$C_4$alkanoyl, and mono- and di-$C_1$-$C_4$alkylphosphate.

(6) R is absent or R is hydroxyl, halogen, cyano, —CONH$_2$, $C_1$-$C_2$alkyl, $C_1$-$C_2$alkoxy, or mono- or di-$C_1$-$C_2$alkylphosphate.

(7) A is 3-pyridyl and R is absent or hydroxyl, fluoro, chloro, cyano, —CONH$_2$, methyl, methoxy, or di-methyl phosphate.

(8) A is

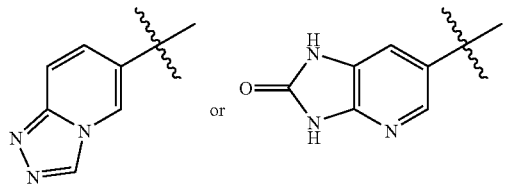

each of which is optionally substituted.

(9) A compound or salt of claim 1, wherein A is:

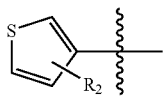

where $R_2$ is 0, 1, or more substituents independently chosen from hydroxyl, halogen, amino, cyano, —COOH, —CONH$_2$, $C_1$-$C_2$haloalkyl, $C_1$-$C_2$haloalkoxy; $C_1$-$C_4$alkyl, $C_1$-$C_4$alkoxy, mono- and di-$C_1$-$C_4$alkylamino, $C_2$-$C_4$alkanoyl, and $C_1$-$C_4$alkylester.

The $R_3$ Variable

The invention includes embodiments in which compounds the variable $R_3$ in Formula I and Formula II carries any of the following definitions.

(1) $R_3$ is halogen, amino, hydroxyl, methyl, methoxy, dimethylamino, or dimethylaminomethyl.

(2) $R_3$ is amino, $C_1$-$C_2$alkyl, or (mono- or di-$C_1$-$C_2$alkylamino)$C_0$-$C_2$alkyl.

(3) $R_3$ is halogen.

(4) $R_3$ is fluoro.

(5) $R_3$ is hydrogen

The $R_4$ Variable

The invention includes embodiments in which compounds the variable $R_4$ in Formula I and Formula II carries any of the following definitions.

(1) $R_4$ is hydrogen, amino, $C_1$-$C_2$alkyl, or $C_2$-$C_4$alkyenylamino.

(2) $R_4$ is hydrogen.

The $R_5$, $R_6$, and $R_7$ Variables

The invention includes embodiments in which compounds the variables $R_5$, $R_6$, and $R_7$ in Formula I and Formula II carries any of the following definitions.

The invention includes embodiments in which compounds the variable $R_4$ in Formula I and Formula II carries any of the following definitions.

(1) $R_5$ is $C_6$-$C_{10}$alkyl, $C_6$-$C_{10}$alkenyl, $C_6$-$C_{10}$alkoxy, $C_6$-$C_{10}$alkenyloxy, or $C_6$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and $R_6$ is halogen, —COOH, —CONH$_2$, $C_1$-$C_2$alkyl, $C_1$-$C_2$alkoxy, methylester, methylsulfonyl, —CF$_2$CH$_3$, trifluormethyl, or trifluoromethoxy.

(2) $R_6$ is $C_4$-$C_{10}$alkyl, $C_4$-$C_{10}$alkenyl, $C_4$-$C_{10}$alkoxy, $C_4$-$C_{10}$alkenyloxy, or $C_4$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and $R_5$ is hydrogen, halogen, cyano, —COOH, —CONH$_2$, $C_1$-$C_2$alkyl, $C_1$-$C_2$alkoxy, methylester, methylsulfonyl, —CF$_2$CH$_3$, trifluormethyl, or trifluoromethoxy.

(3) $R_5$ is halogen, —COOH, —CONH$_2$, $C_1$-$C_2$alkyl, $C_1$-$C_2$alkoxy, methylester, methylsulfonyl, trifluormethyl, or trifluoromethoxy.

(4) $R_5$ is halogen, cyano, —COOH, —CONH$_2$, methyl, methylester, methylsulfonyl, trifluormethyl, or —CF$_2$CH$_3$.

(5) one of $R_5$ and $R_6$ is a group of the formula —O(CH$_2$)$_2$O—, $C_4$-$C_{10}$-carbohydryl, $C_4$-$C_{10}$-carbohydryloxy, or $C_4$-$C_{10}$alkanoyl, where the carbohydryl, carbohydryloxy, or alkanoyl chain may contain one or more oxygen atoms and may be substituted with one or more halogen, hydroxyl, cyano, amino, $C_1$-$C_2$haloalkyl, $C_1$-$C_2$haloalkoxy, and oxo, and where the group of the formula —O(CH$_2$)$_2$O—, $C_4$-$C_{10}$-carbohydryl, $C_4$-$C_{10}$-carbohydryloxy, or $C_4$-$C_{10}$alkanoyl is substituted with one phenyl, naphthyl, pyridyl, pyrimidinyl, pyrazinyl, thienyl, pyrrolyl, furanyl, pyrazoloyl, imidazolyl, pyrrolidinyl, piperidinyl, piperazinyl, morpholinyl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; and the other of $R_5$ and $R_6$ is hydrogen, halogen, cyano, —COOH, —CONH$_2$, $C_1$-$C_2$alkyl, $C_1$-$C_2$alkoxy, methylester, methylsulfonyl, trifluormethyl, or trifluoromethoxy.

(6) One of $R_5$ and $R_6$ is (cyclohexyl)$C_1$-$C_2$alkyl or (cyclohexyl)$C_1$-$C_2$alkoxy and the other of $R_5$ and $R_6$ is hydrogen, —COOH, —CONH$_2$, $C_1$-$C_2$alkyl, $C_1$-$C_2$alkoxy, methylester, $C_1$-methylsulfonyl, trifluormethyl, or trifluoromethoxy.

(7) $R_5$ and $R_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, cyano, $C_1$-$C_8$alkyl, $C_1$-$C_8$alkoxy, and (phenyl)$C_1$-$C_4$alkyl.

(8) $R_5$ and $R_6$ are L and M where:
L is hydrogen, halogen, hydroxyl, amino, cyano, —COOH, —CONH$_2$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and
M is $C_4$-$C_{10}$alkyl, $C_4$-$C_{10}$alkenyl, $C_4$-$C_{10}$alkoxy, or $C_2$-$C_{10}$alkanoyl, each of which may contain one or more oxygen atoms, nitrogen atoms, sulfur atoms or sulfonyl groups and may be substituted with one or more independently chosen halogen, hydroxyl, cyano, amino, $C_1$-$C_2$haloalkyl, $C_1$-$C_2$haloalkoxy, and oxo.

(9) $R_5$ and $R_6$ are L and M, where one of $R_5$ and $R_6$ is L and the other is M, where
L is hydrogen, halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and
M is $C_8$-$C_{20}$alkyl, $C_8$-$C_{20}$alkenyl, $C_8$-$C_{20}$alkoxy, or $C_4$-$C_{20}$alkanoyl, each of which may contain one or more oxygen atoms, nitrogen atoms, sulfur atoms or sulfonyl groups and may be substituted with one or more halogen, hydroxyl, cyano, amino, $C_1$-$C_2$haloalkyl, $C_1$-$C_2$haloalkoxy, and oxo.

(10) $R_5$ and $R_6$ are L and M where:
L is hydrogen, halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and
M is $C_1$-$C_{10}$carbohydryl, $C_1$-$C_{10}$carbohydryloxy, $C_2$-$C_8$alkanoyl, mono- or di-$C_1$-$C_8$alkylamino, where each carbohydryl, carbohydryloxy, alkanoyl, or alkylamino chain may contain one or more oxygen atoms, nitrogen atoms, sulfur atoms, or sulfonyl groups and may be substituted with one or more halogen, hydroxyl, cyano, amino, $C_1$-$C_2$haloalkyl, $C_1$-$C_2$haloalkoxy, and oxo, and each of which carbohydryl, carbohydryloxy, alkanoyl, or alkylamino chain is substituted with one aryl, mono- or bicyclic heteroaryl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; or, M is phenyloxy, indanyloxy, thienyloxy, or pyridyloxy, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; where one of $R_5$ and $R_6$ is L and the other is M.

(11) One of $R_5$ and $R_6$ is L and the other is M, where:

L is hydrogen, halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$haloalkyl, or $C_1$-$C_2$haloalkoxy; and M is $C_1$-$C_{10}$carbohydryl or $C_1$-$C_{10}$carbohydryloxy where each carbohydryl or carbohydryloxy chain may contain one or more oxygen atoms, and may be substituted with one or more halogen, hydroxyl, cyano, amino, $C_1$-$C_2$haloalkyl, $C_1$-$C_2$haloalkoxy, and oxo, and each of which each carbohydryl or carbohydryloxy chain is substituted with one phenyl, naphthyl, pyridyl, thienyl, quinolinyl, isoquinolinyl, indolyl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; or M is phenyloxy or indanyloxy, thienyloxy, each of which is substituted with 0 or 1 or more halogen, hydroxyl, cyano, $C_1$-$C_2$alkyl, $C_1$-$C_2$alkoxy, acetyl, mono- or di-$C_1$-$C_2$alkylamino, $C_1$-$C_2$haloalkyl, or $C_1$-$C_2$haloalkoxy.

(12) One of $R_5$ and $R_6$ is L and the other is M, where: L is hydrogen, cyano, —COOH, —CONH$_2$, methyl, trifluoromethyl, difluoromethyl, acetyl, or CH$_3$O(C=O)— and M carries any of the definitions set forth for embodiments (9) to (11) for the other of the $R_5$ and $R_6$ variables.

(13) $R_5$ and $R_6$ are taken together to form a 5- or 6-membered ring, which is saturated, partially unsaturated, or aromatic, contains 0, 1, or 2 heteroatoms chosen from N, O, and S, and is substituted with 0, 1, or 2 substituents independently chosen from halogen, hydroxyl, amino, cyano, $C_1$-$C_8$alkyl, $C_2$-$C_8$alkenyl, $C_1$-$C_8$alkoxy, oxo, and optionally substituted (phenyl)$C_0$-$C_4$alkyl.

(14) $R_5$ and $R_6$ are taken together to form a 5-membered heteroaryl ring, containing 1 or 2 heteroatoms chosen from N and O, and substituted with 0, 1, or 2 substituents independently chosen from halogen, $C_1$-$C_8$alkyl, $C_1$-$C_8$alkoxy, and (phenyl)$C_0$-$C_4$alkyl.

(15) $R_5$ and $R_6$ are taken together to form a 5-membered heterocycloalkyl ring, containing 1 or 2 heteroatoms chosen from N and O, and substituted with 0, 1, or 2 substituents independently chosen from halogen, $C_1$-$C_8$alkyl, $C_1$-$C_8$alkoxy, and (phenyl)$C_0$-$C_4$alkyl.

(16) $R_7$ is hydrogen, halogen, or methyl.\

(17) $R_7$ is hydrogen.

(18) $R_5$ is $C_6$-$C_{20}$carbohydryl, $C_6$-$C_{20}$carbohydryloxy, $C_2$-$C_{20}$alkanoyl, or $C_6$-$C_{20}$mono- or di-alkylamino, where the carbohydryl, carbohydryloxy, alkanoyl or mono- or di-alkylamino chain may be substituted with one or more halogen, hydroxyl, cyano, amino, $C_1$-$C_2$haloalkyl, $C_1$-$C_2$haloalkoxy, and oxo, and $R_6$ is halogen, hydroxyl, amino, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

(19) $R_5$ is $C_6$-$C_{10}$alkyl, $C_6$-$C_{10}$alkenyl, $C_6$-$C_{10}$alkoxy, $C_6$-$C_{10}$alkenyloxy, or $C_6$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and $R_6$ is halogen, —COOH, —CONH$_2$, $C_1$-$C_2$alkyl, $C_1$-$C_2$alkoxy, methylester, methylsulfonyl, trifluormethyl, or trifluoromethoxy.

(20) $R_6$ is $C_4$-$C_{20}$carbohydryl, $C_4$-$C_{20}$carbohydryloxy, $C_2$-$C_{20}$alkanoyl, where the carbohydryl, carbohydryloxy, or alkanoyl chain may be substituted with one or more halogen, hydroxyl, cyano, amino, $C_1$-$C_2$haloalkyl, $C_1$-$C_2$haloalkoxy, and oxo, and $R_5$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

(21) $R_6$ is $C_4$-$C_{10}$alkyl, $C_4$-$C_{10}$alkenyl, $C_4$-$C_{10}$alkoxy, $C_4$-$C_{10}$alkenyloxy, or $C_4$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and $R_5$ is hydrogen, halogen, cyano, —COOH, —CONH$_2$, $C_1$-$C_2$alkyl, $C_1$-$C_2$alkoxy, methylester, methylsulfonyl, trifluormethyl, or trifluoromethoxy.

(22) $R_6$ is $C_4$-$C_{10}$alkyl, $C_4$-$C_{10}$alkenyl, $C_4$-$C_{10}$alkoxy, $C_4$-$C_{10}$alkenyloxy, or $C_4$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and $R_5$ is halogen, —COOH, —CONH$_2$, $C_1$-$C_2$alkyl, $C_1$-$C_2$alkoxy, methylester, methylsulfonyl, trifluormethyl, or trifluoromethoxy.

(23) One of $R_5$ and $R_6$ is $C_4$-$C_{20}$carbohydryl, $C_4$-$C_{20}$carbohydryloxy, or $C_2$-$C_{20}$alkanoyl, where the carbohydryl, carbohydryloxy, or alkanoyl chain contains one or more oxygen atoms, nitrogen atoms, sulfur atoms, or sulfonyl groups and may be substituted with one or more halogen, hydroxyl, cyano, amino, $C_1$-$C_2$haloalkyl, $C_1$-$C_2$haloalkoxy, and oxo, and the other of $R_5$ and $R_6$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

(24) One of $R_5$ and $R_6$ is a group of the formula —O(CH$_2$)$_2$O—, $C_4$-$C_{20}$carbohydryl, $C_4$-$C_{20}$carbohydryloxy, $C_4$-$C_{10}$alkanoyl, where the carbohydryl, carbohydryloxy, or alkanoyl chain may contain one or more oxygen atoms, nitrogen atoms, sulfur atoms, or sulfonyl groups and may be substituted with one or more halogen, hydroxyl, cyano, amino, $C_1$-$C_2$haloalkyl, $C_1$-$C_2$haloalkoxy, and oxo, and where the group of the formula —O(CH$_2$)$_2$O—, $C_4$-$C_{10}$carbohydryl, $C_4$-$C_{10}$-carbohydryloxy, or $C_4$-$C_{10}$alkanoyl is substituted with one aryl, mono- or bicyclic heteroaryl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; and the other of $R_5$ and $R_6$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

(25) One of $R_5$ and $R_6$ is a group of the formula —O(CH$_2$)$_2$O—, $C_4$-$C_{10}$-carbohydryl, $C_4$-$C_{10}$carbohydryloxy, or $C_4$-$C_{10}$alkanoyl, where the carbohydryl, carbohydryloxy, or alkanoyl chain may contain one or more oxygen atoms and may be substituted with one or more halogen, hydroxyl, cyano, amino, $C_1$-$C_2$haloalkyl, $C_1$-$C_2$haloalkoxy, and oxo, and where the group of the formula —O(CH$_2$)$_2$O—, $C_4$-$C_{10}$-carbohydryl, $C_4$-$C_{10}$-carbohydryloxy, or $C_4$-$C_{10}$alkanoyl is substituted with one phenyl, naphthyl, pyridyl, pyrimidinyl, pyrazinyl, thienyl, pyrrolyl, furanyl, pyrazoloyl, imidazolyl, pyrrolidinyl, piperidinyl, piperazinyl, morpholinyl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy;

and the other of $R_5$ and $R_6$ is hydrogen, halogen, cyano, —COOH, —CONH$_2$, $C_1$-$C_2$alkyl, $C_1$-$C_2$alkoxy, methylester, methylsulfonyl, trifluormethyl, or trifluoromethoxy.

(26) One of $R_5$ and $R_6$ is phenoxy, benzyloxy, or indanyloxy; each of which is substituted with 0, 1 or 2 substituents independently chosen from halogen, cyano, $C_1$-$C_2$alkyl, $C_1$-$C_2$alkoxy, mono- or di-$C_1$-$C_4$alkylamino, trifluoromethyl, or trifluoromethoxy; and the other of $R_5$ and $R_6$ is halogen, hydroxyl, amino, cyano, —COOH, —CONH$_2$, $C_1$-$C_2$alkyl, $C_1$-$C_2$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

(27) One of $R_5$ and $R_6$ is ($C_3$-$C_7$cycloalkyl)$C_0$-$C_2$alkyl or ($C_3$-$C_7$cycloalkyl)$C_0$-$C_2$alkoxy and the other of $R_5$ and $R_6$ is hydrogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and the other of $R_6$ is halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

(28) One of $R_5$ and $R_6$ is (cyclohexyl)$C_1$-$C_2$alkyl or (cyclohexyl)$C_1$-$C_2$alkoxy and the other of $R_5$ and $R_6$ is hydrogen, —COOH, —CONH$_2$, $C_1$-$C_2$alkyl, $C_1$-$C_2$alkoxy, methylester, $C_1$-methylsulfonyl, trifluoromethyl, or trifluoromethoxy.

(29) One of $R_5$ and $R_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, hydroxyl, amino, cyano, $C_1$-$C_{10}$alkyl, $C_2$-$C_{10}$alkenyl, $C_1$-$C_{10}$alkoxy, and optionally substituted (phenyl)$C_0$-$C_4$alkyl.

(29) $R_5$ and $R_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, cyano, $C_1$-$C_8$alkyl, $C_1$-$C_8$alkoxy, and (phenyl)$C_1$-$C_4$alkyl.

The invention includes all combinations of definitions for the variables A and $R_1$ to $R_7$ given above so long as a stable compound or salt of the invention results. For example the invention includes compounds and salts of Formula I, in which the A variable is carries definition (7), the $R_3$ variable carries definition (3) the $R_4$ variable carries definition (2), $R_5$ and $R_6$ carry definition (8) and $R_7$ carries definition (17). Thus the invention includes compounds and salts of Formula III

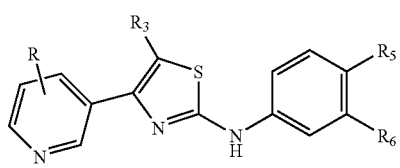

Formula III wherein:
R is absent or hydroxyl, fluoro, chloro, cyano, —CONH$_2$, methyl, methoxy, or di-methyl phosphate.
$R_3$ is halogen.
$R_5$ and $R_6$ are L and M where:
L is hydrogen, halogen, hydroxyl, amino, cyano, —COOH, —CONH$_2$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and
M is $C_4$-$C_{10}$alkyl, $C_4$-$C_{10}$alkenyl, $C_4$-$C_{10}$alkoxy, or $C_2$-$C_{10}$alkanoyl, each of which may contain one or more oxygen atoms, nitrogen atoms, sulfur atoms or sulfonyl groups and may be substituted with one or more independently chosen halogen, hydroxyl, cyano, amino, $C_1$-$C_2$haloalkyl, $C_1$-$C_2$haloalkoxy, and oxo.

The invention also includes compounds as salts of Formula IV

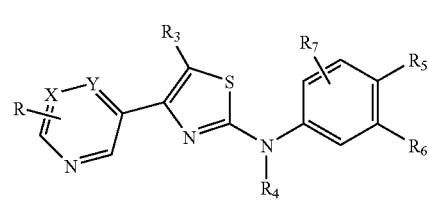

Formula IV wherein X, Y, R, and $R_3$ to $R_7$ carry any of the definitions set forth above for these variables.

The invention includes compounds and salts of Formula IV in which
X and Y are CH;
R is absent or R is hydroxyl, halogen, cyano, —CONH$_2$, $C_1$-$C_2$alkyl, $C_1$-$C_2$alkoxy, or mono- or di-$C_1$-$C_2$alkylphosphate;
$R_3$ is hydrogen, halogen, amino, hydroxyl, methyl, methoxy, dimethylamino, or dimethylaminomethyl;
$R_4$ is hydrogen;
$R_5$ and $R_6$ are taken together to form a 5-membered heteroaryl ring, containing 1 or 2 heteroatoms chosen from N and O, and substituted with 0, 1, or 2 substituents independently chosen from halogen, $C_1$-$C_8$alkyl, $C_1$-$C_8$alkoxy, and (phenyl)$C_0$-$C_4$alkyl; and
$R_7$ is hydrogen, halogen, or methyl.

The invention includes compounds and salts of Formula IV, wherein $R_3$ is halogen.

The invention also includes compounds and salts of Formula IV, wherein
X and Y are independently CH or N;
R is absent or R is hydroxyl, halogen, cyano, —CONH$_2$, $C_1$-$C_2$alkyl, $C_1$-$C_2$alkoxy, or mono- or di-$C_1$-$C_2$alkylphosphate;
$R_3$ is hydrogen, halogen, amino, hydroxyl, methyl, methoxy, dimethylamino, or dimethylaminomethyl (in some embodiments $R_3$ is halogen);
$R_4$ is hydrogen;
$R_5$ and $R_6$ are L and M, wherein: L is hydrogen, halogen, hydroxyl, amino, cyano, —COOH, —CONH$_2$, $C_1$-$C_2$alkyl, $C_1$-$C_4$alkoxy, $C_2$-$C_4$alkanoyl, $C_1$-$C_2$alkylester, $C_1$-$C_2$haloalkyl, or $C_1$-$C_2$haloalkoxy; and M is $C_1$-$C_{10}$carbohydryl or $C_1$-$C_{10}$carbohydryloxy where each carbohydryl or carbohydryloxy, chain may contain one or more oxygen atoms, and may be substituted with one or more halogen, hydroxyl, cyano, amino, $C_1$-$C_2$haloalkyl, $C_1$-$C_2$haloalkoxy, and oxo, and each of which is substituted with one phenyl, naphthyl, pyridyl, thienyl, quinolinyl, isoquinolinyl, indolyl, $C_3$-$C_7$cycloalkyl, or 5- to 7-membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; or
M is phenyloxy or indanyloxy, thienyloxy, each of which is substituted with 0 or 1 or more halogen, hydroxyl, cyano, $C_1$-$C_2$alkyl, $C_1$-$C_2$alkoxy, acetyl, mono- or di-$C_1$-$C_2$alkylamino, $C_1$-$C_2$haloalkyl, or $C_1$-$C_2$haloalkoxy; where one of $R_5$ and $R_6$ is L and the other is M; and
$R_7$ is hydrogen, halogen, or methyl.

The invention further includes compounds and salts of Formula IV in which X and Y are CH; R is absent or R is hydroxyl, halogen, cyano, —CONH$_2$, C$_1$-C$_2$alkyl, C$_1$-C$_2$alkoxy, or mono- or di-C$_1$-C$_2$alkylphosphate; R$_3$ is hydrogen or halogen; R$_4$ is hydrogen; and R$_7$ is hydrogen, halogen, or methyl; and one or more of the following conditions is met for R$_5$ and R$_6$.

(i) R$_5$ is C$_6$-C$_{10}$alkyl, C$_6$-C$_{10}$alkenyl, C$_6$-C$_{10}$alkoxy, C$_6$-C$_{10}$alkenyloxy, or C$_6$-C$_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and R$_6$ is halogen, —COOH, —CONH$_2$, C$_1$-C$_2$alkyl, C$_1$-C$_2$alkoxy, methylester, methylsulfonyl, trifluormethyl, or trifluoromethoxy.

(ii) R$_6$ is C$_4$-C$_{10}$alkyl, C$_4$-C$_{10}$alkenyl, C$_4$-C$_{10}$alkoxy, C$_4$-C$_{10}$alkenyloxy, or C$_4$-C$_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and R$_5$ is hydrogen, halogen, cyano, —COOH, —CONH$_2$, C$_1$-C$_2$alkyl, C$_1$-C$_2$alkoxy, methylester, methylsulfonyl, trifluoromethyl, or trifluoromethoxy.

(iii) One of R$_5$ and R$_6$ is C$_4$-C$_{20}$carbohydryl, C$_4$-C$_{20}$carbohydryloxy, or C$_2$-C$_{20}$alkanoyl, where the carbohydryl, carbohydryloxy, or alkanoyl chain contains one or more oxygen atoms, nitrogen atoms, sulfur atoms, or sulfonyl groups and may be substituted with one or more halogen, hydroxyl, cyano, amino, C$_1$-C$_2$haloalkyl, C$_1$-C$_2$haloalkoxy, and oxo, and the other of R$_5$ and R$_6$ is hydrogen, halogen, hydroxyl, amino, cyano, —COOH, —CONH$_2$, C$_1$-C$_4$alkyl, C$_1$-C$_4$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy.

(iv) One of R$_5$ and R$_6$ is a group of the formula —O(CH$_2$)$_2$O—, C$_4$-C$_{10}$-carbohydryl, C$_4$-C$_{10}$-carbohydryloxy, or C$_4$-C$_{10}$alkanoyl, where the carbohydryl, carbohydryloxy, or alkanoyl chain may contain one or more oxygen atoms and may be substituted with one or more halogen, hydroxyl, cyano, amino, C$_1$-C$_2$haloalkyl, C$_1$-C$_2$haloalkoxy, and oxo, and where the group of the formula —O(CH$_2$)$_2$O—, C$_4$-C$_{10}$-carbohydryl, C$_4$-C$_{10}$-carbohydryloxy, or C$_4$-C$_{10}$alkanoyl is substituted with one phenyl, naphthyl, pyridyl, pyrimidinyl, pyrazinyl, thienyl, pyrrolyl, furanyl, pyrazoloyl, imidazolyl, pyrrolidinyl, piperidinyl, piperazinyl, morpholinyl, C$_3$-C$_7$cycloalkyl, or 5- to 7-membered heterocycloalkyl, each of which is substituted with 0 or 1 or more halogen, hydroxyl, cyano, C$_1$-C$_4$alkyl, C$_1$-C$_4$alkoxy, C$_2$-C$_4$alkanoyl, mono- or di-C$_1$-C$_4$alkylamino, C$_1$-C$_2$haloalkyl, or C$_1$-C$_2$haloalkoxy; and the other of R$_5$ and R$_6$ is hydrogen, halogen, cyano, —COOH, —CONH$_2$, C$_1$-C$_2$alkyl, C$_1$-C$_2$alkoxy, methylester, methylsulfonyl, trifluormethyl, or trifluoromethoxy.

(v) One of R$_5$ and R$_6$ is phenoxy, benzyloxy, or indanyloxy; each of which is substituted with 0, 1 or 2 substituents independently chosen from halogen, cyano, C$_1$-C$_2$alkyl, C$_1$-C$_2$alkoxy, mono- or di-C$_1$-C$_4$alkylamino, trifluoromethyl, or trifluoromethoxy; and the other of R$_5$ and R$_6$ is halogen, hydroxyl, amino, cyano, —COOH, —CONH$_2$, C$_1$-C$_2$alkyl, C$_1$-C$_2$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy.

(vi) One of R$_5$ and R$_6$ is (cyclohexyl)C$_1$-C$_2$alkyl or (cyclohexyl)C$_1$-C$_2$alkoxy and the other of R$_5$ and R$_6$ is hydrogen, —COOH, —CONH$_2$, C$_1$-C$_2$alkyl, C$_1$-C$_2$alkoxy, methylester, C$_1$-methylsulfonyl, trifluoromethyl, or trifluoromethoxy; and the other of R$_6$ is halogen, hydroxyl, amino, cyano, —COOH, —CONH$_2$, C$_1$-C$_4$alkyl, C$_1$-C$_4$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy.

(vii) R$_5$ and R$_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, hydroxyl, amino, cyano, C$_1$-C$_{10}$alkyl, C$_2$-C$_{10}$alkenyl, C$_1$-C$_{10}$alkoxy, and optionally substituted (phenyl)C$_0$-C$_4$alkyl.

The invention also includes compounds and salts of Formula V

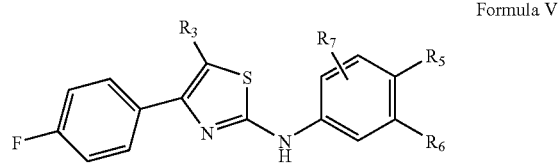

Formula V

Within Formula V:

R$_3$ is hydrogen or fluoro;

R$_5$ is C$_1$-C$_{10}$alkoxy, which alkoxy chain may contain one or more oxygen atoms and is substituted with one phenyl or C$_3$-C$_7$cycloalkyl, each of which is substituted with 0 or 1 or more halogen, hydroxyl, cyano, C$_1$-C$_2$alkyl, C$_1$-C$_2$alkoxy, C$_2$-C$_4$alkanoyl, mono- or di-C$_1$-C$_2$alkylamino, C$_1$-C$_2$haloalkyl, or C$_1$-C$_2$haloalkoxy; and R$_6$ is halogen, methyl, methoxy, acetyl, trifluoromethyl, or trifluoromethoxy; and R$_7$ is hydrogen, halogen, or methyl.

In certain embodiments R$_5$ is C$_5$-C$_{10}$alkoxy, which alkoxy chain may contain one or more oxygen atoms and is substituted with one phenyl or C$_3$-C$_7$cycloalkyl, each of which is substituted with 0 or 1 or more halogen, hydroxyl, cyano, C$_1$-C$_2$alkyl, C$_1$-C$_2$alkoxy, C$_2$-C$_4$alkanoyl, mono- or di-C$_1$-C$_2$alkylamino, C$_1$-C$_2$haloalkyl, or C$_1$-C$_2$haloalkoxy.

The invention also includes compounds of Formula VI

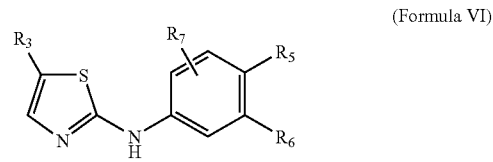

(Formula VI)

Within Formula VI

R$_3$ is halogen;

R$_5$ and R$_6$ are L and M, wherein: L is hydrogen, halogen, hydroxyl, amino, cyano, C$_1$-C$_2$alkyl, C$_1$-C$_4$alkoxy, C$_1$-C$_2$haloalkyl, or C$_1$-C$_2$haloalkoxy; and M is C$_6$-C$_{10}$alkyl or C$_6$-C$_{10}$alkoxy where each C$_6$-C$_{10}$alkyl or C$_6$-C$_{10}$alkoxy, chain may contain one or more oxygen atoms, and may be substituted with one or more halogen, hydroxyl, cyano, amino, C$_1$-C$_2$haloalkyl, C$_1$-C$_2$haloalkoxy, and oxo, and each of which may be substituted with one cyclic group chosen from phenyl, pyridyl, thienyl, C$_3$-C$_7$cycloalkyl, and 5- to 7-membered heterocycloalkyl, each of which cyclic group is substituted with 0 or 1 or more halogen, hydroxyl, cyano, C$_1$-C$_4$alkyl, C$_1$-C$_4$alkoxy, C$_2$-C$_4$alkanoyl, mono- or di-C$_1$-C$_4$alkylamino, C$_1$-C$_2$haloalkyl, or C$_1$-C$_2$haloalkoxy; where one of R$_5$ and R$_6$ is L and the other is M; and R$_7$ is hydrogen, halogen, or methyl.

The invention includes compounds and salts of Formula VII

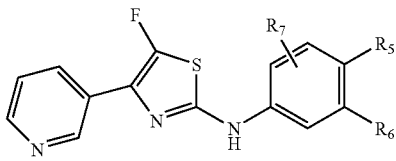

wherein:

$R_5$ is $C_4$-$C_{10}$alkyl or $C_4$-$C_{10}$alkoxy, each of which is substituted with 0 or 1 or more halogen, hydroxyl, cyano, $C_1$-$C_2$alkyl, $C_1$-$C_2$alkoxy, $C_2$-$C_4$alkanoyl, mono- or di-$C_1$-$C_2$alkylamino, $C_1$-$C_2$haloalkyl, or $C_1$-$C_2$haloalkoxy; and $R_6$ is halogen, cyano, —$CONH_2$, —COOH, methyl, methoxy, acetyl, trifluoromethyl, —$CF_2CH_3$, or trifluoromethoxy; and $R_7$ is hydrogen, halogen, or methyl.

Pharmaceutical Preparations

Compounds of the invention can be administered as the neat chemical, but are preferably administered as a pharmaceutical composition. Accordingly, the invention provides pharmaceutical formulations comprising a compound or pharmaceutically acceptable salt of the invention, together with at least one pharmaceutically acceptable carrier.

Compounds of the invention may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Binders are substances that bind or "glue" powders together and make them cohesive by forming granules, thus serving as the "adhesive" in the formulation. Binders add cohesive strength to that already available in the diluent or bulking agent. Examples of binders include starch, gelatin, natural sugars, corn sweeteners, natural and synthetic gums such as acacia, sodium alginate, carboxymethylcellulose, polyethylene glycol and waxes. The amount of binder in the composition can range, for example, from about 2 to about 20% by weight of the composition, or from about 3 to about 10% by weight, even more preferably from about 3 to about 6% by weight.

Diluents include sugars such as lactose, sucrose, mannitol and sorbitol; starches derived from wheat, corn, rice and potato; and celluloses such as microcrystalline cellulose. The amount of diluent in the composition may be, for example, about 10 to about 90% by weight of the total composition, about 25 to about 75%, about 30 to about 60% by weight, or about 12 to about 60%.

Disintegrants are materials added to a pharmaceutical composition to help it break apart (disintegrate) and release the active agent. Suitable disintegrants include starches; including "cold water soluble" modified starches such as sodium carboxymethyl starch; natural and synthetic gums such as locust bean, karaya, guar, and tragacanth gum and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range, for example, from about 2 to about 15% by weight of the composition or from about 4 to about 10% by weight.

Lubricants are substances added to a pharmaceutical formulation to enable the tablet, granules, etc. after it has been compressed, to release from the mold or die by reducing friction or wear. Examples of lubricants useful in pharmaceutical dosage forms include boric acid, sodium benzoate, sodium acetate, sodium chloride, and the like. Lubricants are usually added at the very last step before tablet compression, since they must be present on the surfaces of the granules and in between them and the parts of the tablet press. The amount of lubricant in the composition can range, for example, from about 0.1 to about 5% by weight of the composition, from about 0.5 to about 2%, or from about 0.3 to about 1.5% by weight. The amount of compound or salt of the invention in a unit dose may be generally varied or adjusted from about 1.0 milligram to about 1,000 milligrams, from about 1.0 to about 900 milligrams, from about 1.0 to about 500 milligrams, or from about 1 to about 250 milligrams, according to the particular application and the potency of the compound. The actual dosage employed may be varied depending upon the patient's age, sex, weight and severity of the condition being treated.

Pharmaceutical compositions formulated for oral administration are often preferred. These compositions contain between 0.1 and 99% of a compound of the invention and usually at least about 5% (weight %) of a compound of the invention. Some embodiments contain from about 25% to about 50% or from 5% to 75% of a compound of invention.

Liquids Formulations

Compounds of the invention can be incorporated into oral liquid preparations such as aqueous or oily suspensions, solutions, emulsions, syrups, tinctures, syrups, or elixirs, for example. Moreover, formulations containing these compounds can be presented as a dry product, e.g. as granules or powders, for constitution with water or other suitable vehicle before use. Typical components of carriers for syrups, elixirs, emulsions and suspensions include ethanol, glycerol, propylene glycol, polyethylene glycol, liquid sucrose, sorbitol and water. Liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid). Oral formulations may contain demulcent, flavoring agents, sweetening agents, such as sucrose or saccharin, taste-masking agents, and coloring agents.

Suspensions

Aqueous suspensions contain the active material(s) in admixture with excipients suitable for the manufacture of aqueous suspensions. Such excipients are suspending agents, for example AVICEL RC-591, sodium carboxymethylcellulose, methylcellulose, hydropropylmethylcellulose, sodium alginate, polyvinylpyrrolidone, gum tragacanth and gum acacia; dispersing or wetting agents, for example lecithin and polysorbate 80. The aqueous suspensions may also contain one or more preservatives, for example ethyl, n-propyl p-hydroxybenzoate, methyl parabens, propyl parabens, and sodium benzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Emulsions

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. Tablets and Capsules Tablets typically comprise conventional pharmaceutically compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard or soft shell capsules. A capsule is a dosage form administered in a special container or enclosure containing an active agent. The active agent may be present in solid, liquid, gel, or powder form, or any other pharmaceutically acceptable form. A capsule shell may be made of methyl cellulose, polyvinyl alcohols, or denatured gelatins or starch or other material. Hard shell capsules are typically made of blends of relatively high gel strength bone and pork skin gelatins. Soft shell capsule shells are often made of animal or plant gelatins. The capsule itself may contain small amounts of dyes, opaquing agents, plasticizers and preservatives.

The active agent in a capsule may be mixed with an inert solid diluent, for example, calcium carbonate, calcium phosphate or kaolin, or in the case of soft gelatin capsules the active ingredient may be mixed with water or an oil medium, for example peanut oil, liquid paraffin or olive oil.

Injectable and Parenteral Formulations

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid are useful in the preparation of injectables.

Compounds of the invention may be administered parenterally in a sterile medium. Parenteral administration includes subcutaneous injections, intravenous, intramuscular, intrathecal injection or infusion techniques. The drug, depending on the vehicle and concentration used, can either be suspended or dissolved in the vehicle. Advantageously, adjuvants such as local anesthetics, preservatives and buffering agents can be dissolved in the vehicle. In compositions for parenteral administration the carrier typically comprises least about 90% by weight of the total composition.

Methods of Treatment

The invention includes methods of preventing and treating hepatitis C infections, by providing a therapeutically effective amount of a compound of the invention to patient at risk for viral infection or having a viral infection. In certain embodiments the virus is a hepatitis C virus.

The pharmaceutical combinations disclosed herein are useful for preventing and treating viral infections, including hepatitis C infections, in patients. An effective amount of a pharmaceutical combination of the invention may be an amount sufficient to (a) prevent hepatitis C or a symptom of a hepatitis C from occurring in a patient who may be predisposed to hepatitis C but has not yet been diagnosed as having it or prevent diseases that may be associated with or caused by a primary hepatitis C infection (such as liver fibrosis that can result in the context of chronic HCV infection); (b) inhibit the progression of hepatitis C; and (c) cause a regression of the hepatitis C infection. An amount of a pharmaceutical composition effect to inhibit the progress or cause a regression of hepatitis C includes an amount effective to stop the worsening of symptoms of hepatitis C or reduce the symptoms experienced by a patient infected with the hepatitis C virus. Alternatively a halt in progression or regression of hepatitis C may be indicated by any of several markers for the disease. For example, a lack of increase or reduction in the hepatitis C viral load or a lack of increase or reduction in the number of circulating HCV antibodies in a patient's blood are markers of a halt in progression or regression of hepatitis C infection. Other hepatitis C disease markers include aminotransferase levels, particularly levels of the liver enzymes AST and ALT. Normal levels of AST are from 5 to 40 units per liter of serum (the liquid part of the blood) and normal levels of ALT are from 7 to 56 units per liter of serum. These levels will typically be elevated in a HCV infected patient. Disease regression is usually marked by the return of AST and ALT levels to the normal range.

Symptoms of hepatitis C that may be affected by an effective amount of a pharmaceutical combination of the invention include decreased liver function, fatigue, flu-like symptoms: fever, chills, muscle aches, joint pain, and headaches, nausea, aversion to certain foods, unexplained weight loss, psychological disorders including depression, tenderness in the abdomen, and jaundice.

"Liver function" refers to a normal function of the liver, including, but not limited to, a synthetic function including synthesis of proteins such as serum proteins (e.g., albumin, clotting factors, alkaline phosphatase, aminotransferases (e.g., alanine transaminase, aspartate transaminase), 5'-nucleosidase, y glutaminyltranspeptidase, etc.), synthesis of bilirubin, synthesis of cholesterol, and synthesis of bile acids; a liver metabolic function, including carbohydrate metabolism, amino acid and ammonia metabolism, hormone metabolism, and lipid metabolism; detoxification of exogenous drugs; and a hemodynamic function, including splanchnic and portal hemodynamics.

An effective amount of a combination described herein will also provide a sufficient concentration of the active agents in the concentration when administered to a patient. A sufficient concentration of an active agent is a concentration of the agent in the patient's body necessary to prevent or combat the infection. Such an amount may be ascertained experimentally, for example by assaying blood concentration of the agent, or theoretically, by calculating bioavailability. The amount of an active agent sufficient to inhibit viral infection in vitro may be determined with a conventional assay for viral infectivity such as a replicon based assay, which has been described in the literature.

Frequency of dosage may also vary depending on the compound used and the particular disease treated. However, for treatment of most infectious disorders, a dosage regimen of 4 times daily or less is preferred and a dosage regimen of 1 or 2 times daily is particularly preferred. Dosage levels of each active agent of from about 0.1 mg to about 140 mg per kilogram of body weight per day are useful in the treatment of the above-indicated conditions (about 0.5 mg to about 7 g per patient per day). The amount of active agent that may be combined with the carrier materials to produce a single dosage form will vary depending upon the patient treated and the particular mode of administration. Dosage unit forms will generally contain between from about 1 mg to about 500 mg of each active agent. In certain embodiments 25 mg to 500 mg, or 25 mg to 200 mg of a compound of the invention are provided daily to a patient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Combination Methods

The invention includes methods of treatment in which a compound or salt of the invention is provided together with one or more additional active agents.

The invention also includes using pharmaceutical combinations comprising a compound of the invention and at least one additional active agent in prophylactic therapies. In the context of prophylactic or preventative treatment an effective amount of a compound of the invention is an amount sufficient to significantly decrease the patient's risk of contracting a hepatitis C infection.

In certain embodiments method of treatment includes providing a patient with a compound of Formula I and an interferon such as a pegylated interferon or interferon gamma. The interferon may be the only compound provided with the compound of the invention or may be provided with an additional active agent that is not an interferon. Patients receiving hepatitis C medications are typically given interferon together with another active agent. Thus methods of treatment and pharmaceutical combinations in which a compound of the invention is provided together with an interferon, such as pegylated interferon alfa 2a, as the additional active agents are included as embodiments. Similarly methods and pharmaceutical combinations in which ribavirin is an additional active agent are provided herein.

In certain embodiments the additional active agent (or agents) used with the compound of the invention is an HCV protease inhibitor or a nucleoside or non-nucleoside HCV polymerase inhibitor. HCV protease inhibitors include NS3 protease inhibitors. For example the combination may include an NS3 protease inhibitors such as telaprevir (VX-950) or the combination may include a polymerase inhibitor such as valopicitabine, or NM 107, the active agent which valopicitabine is converted into in vivo. Additional NS3 protease inhibitors that may be used together with a compound of the invention include TMC435350 (Tibotec), MK 7009 (Merck), and ITMN-191 (Intermune). Other suitable NS3 protease inhibitors include the protease inhibitors discussed in U.S. Ser. No. 11/777,745, filed Jul. 13, 2007, which is hereby incorporated by reference at pages 51-67 for its teachings regarding protease inhibitors that act at NS3. NS3 inhibitors discussed in the '745 application include (2S,4R)-1-((S)-2-tert-butyl-4-oxo-4-(piperidin-1-yl)butanoyl)-N-(1-(cyclopropylsulfonylcarbamoyl)-2-vinylcyclopropyl)-4-(7-methoxy-2-phenylquinolin-4-yloxy)pyrrolidine-2-carboxamide; (2R,6R,13aS,14aR,16aS,Z)-N-(cyclopropylsulfonyl)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16a-hexadecahydrocyclopropa[e]pyrrolo[1,2-a][1,4]diazacyclopentadecine-14a-carboxamide; (2R,6R,13aR,14aS,16aS,Z)-N-(cyclopropylsulfonyl)-2-(7-methoxy-2-phenylquinolin-4-yloxy)-5,16-dioxo-6-(2-oxo-2-(piperidin-1-yl)ethyl)-1,2,3,5,6,7,8,9,10,11,13a,14,14a,15,16,16ahexadecahydrocyclopropa[e]pyrrolo[1,2-a][1,4]diazacyclopentadecine-14a-carboxamide; and (2S,4R)-1-((S)-2-tert-butyl-4-oxo-4-(piperidin-1-yl)butanoyl)-N-((1R,2S)-1-(cyclopropylsulfonylcarbamoyl)-2-vinylcyclopropyl)-4-(7-methoxy-2-phenylquinolin-4-yloxy)pyrrolidine-2-carboxamide.

Other suitable active agents that may be used in combination with a compound of the invention include ciluprevir, SCH 503034 (boceprevir), and teleprevir (Vertex/Janssen/Mitsubishi Tanabe).

Nucleoside and non-nucleoside polymerase inhibitors that may be used in combination with a compound of the invention include R-7128 (Roche-Pharmasset) and R-1616 (Roche).

Another active agent that may be used in combination with compounds of the invention is the anti-protozoal compound nitazoxamide (ALINIA).

According to the methods of the invention, the compound of the invention and an additional active agent may be: (1) co-formulated and administered or delivered simultaneously in a combined formulation; (2) delivered by alternation or in parallel as separate formulations; or (3) by any other combination therapy regimen known in the art. When delivered in alternation therapy, the methods of the invention may comprise administering or delivering the compound of The invention and an additional active agent sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

The invention methods of treatment and pharmaceutical combinations including compounds of the invention any one or combination of the following compounds and substances as an additional active agent:

Caspase inhibitors: IDN 6556 (Idun Pharmaceuticals)

Cyclophilin Inhibitors: NIM811 (Novartis) and DEBIO-025 (Debiopharm)

Cytochrome P450 monooxygenase inhibitors: ritonavir (WO 94/14436), ketoconazole, troleandomycin, 4-methylpyrazole, cyclosporin, clomethiazole, cimetidine, itraconazole, fluconazole, miconazole, fluvoxamine, fluoxetine, nefazodone, sertraline, indinavir, nelfmavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole Glucocorticoids: hydrocortisone, cortisone, prednisone, prednisolone, methylprednisolone, triamcinolone, paramethasone, betamethasone, and dexamethasone Hematopoietins: hematopoietin-1 and hematopoietin-2. Other members of the hematopoietin superfamily such as the various colony stimulating factors (e.g. (e.g. G-CSF, GM-CSF, M-CSF), Epo, and SCF (stem cell factor)

Homeopathic Therapies: Milk Thistle, silymarin, ginseng, glycyrrhizin, licorice root, schisandra, vitamin C, vitamin E, beta carotene, and selenium Immunomodulatory compounds: thalidomide, IL-2, hematopoietins, IMPDH inhibitors, for example Merimepodib (Vertex Pharmaceuticals Inc.), interferon, including natural interferon (such as OMNIFERON, Viragen and SUMIFERON, Sumitomo, a blend of natural interferons), natural interferon alpha (ALFERON, Hemispherx Biopharma, Inc.), interferon alpha nl from lymphblastoid cells (WELLFERON, Glaxo Wellcome), oral alpha interferon, Peg-interferon, Peg-interferon alfa 2a (PEGASYS, Roche), recombinant interferon alfa 2a (ROFERON, Roche), inhaled interferon alpha 2b (AERX, Aradigm), Peg-interferon alpha 2b (ALBUFERON, Human Genome Sciences/Novartis, PEGINTRON, Schering), recombinant interferon alfa 2b (INTRON A, Schering), pegylated interferon alfa 2b (PEG-INTRON, Schering, VIRAFERONPEG, Schering), interferon beta-1a (REBIF, Serono, Inc. and Pfizer), consensus interferon alpha (INFERGEN, Valeant Pharmaceutical), interferon gamma-1b (ACTIMMUNE, Intermune, Inc.), un-pegylated interferon alpha, alpha interferon, and its analogs, and synthetic thymosin alpha 1 (ZADAXIN, SciClone Pharmaceuticals Inc.)

Immunosupressants: sirolimus (RAPAMUNE, Wyeth)

Interleukins: (IL-1, IL-3, IL-4, IL-5, IL-6, IL-10, IL-11, IL-12), LIF, TGF-beta, TNF-alpha) and other low molecular weight factors (e.g. AcSDKP, pEEDCK, thymic hormones, and minicytokines)

Interferon Enhancers: EMZ702 (Transition Therapeutics)

IRES inhibitors: VGX-410C (VGX Pharma)

Monoclonal and Polyclonal antibodies: XTL-6865 (XTL), HuMax-HepC (Genmab), Hepatitis C Immune Globin (human) (CIVACIR, Nabi Biopharmaceuticals)

Natural products: Silymarin and silibin (silybin)

Nucleoside analogues: Lamivudine (EPIVIR, 3TC, GlaxoSmithKline), MK-0608 (Merck), zalcitabine (HIVID, Roche US Pharmaceuticals), ribavirin (including COPEGUS (Roche), REBETOL (Schering), VILONA (ICN Pharmaceuticals, and VIRAZOLE (ICN Pharmaceuticals), viramidine (Valeant Pharmaceuticals), an amidine prodrug of ribavirin, R-7128 (Roche-Pharmasset), and R-1626 (Roche). Combinations of nucleoside analogues may also be employed.

Non-nucleoside inhibitors: PSI-6130 (Roche/Pharmasset), delaviridine (RESCRIPTOR, Pfizer), and HCV-796 (Viropharm)

P7 protein inhibitor: amantadine (SYMMETREL, Endo Pharmaceuticals, Inc.)

Polymerase inhibitors: NM283 (valopicitabine) (Idenix) and NM 107 (Idenix).

Protease inhibitors: BILN-2061 (Boehringer Ingelheim), GW-433908 (prodrug of Amprenavir, Glaxo/Vertex), indinavir (CRIXIVAN, Merck), ITMN-191 (Intermune/Array Biopharma), VX950 (Vertex), MK-7009, ITMN-191, TMC435350, and combinations comprising one or more of the foregoing protease inhibitors RNA interference: SIRNA-034 RNAi (Sirna Therapeutics)

Therapeutic Vaccines: IC41 (Intercell), IMN-0101 (Imnogenetics), GI 5005 (Globeimmune), Chronvac-C (Tripep/Inovio), ED-002 (Imnogenetics), Hepavaxx C (ViRex Medical)

TNF agonists: adalimumab (HUMIRA, Abbott), entanercept (ENBREL, Amgen and Wyeth), infliximab (REMICADE, Centocor, Inc.)

Tubulin inhibitors: Colchicine

Sphingosine-1-phosphate receptor modulators: FTY720 (Novartis)

TLR agonists: ANA-975 (Anadys Pharmaceuticals), TLR7 agonist (Anadys Pharmaceuticals), CPG10101 (Coley), and TLR9 agonists including CPG 7909 (Coley)

Cyclophilin Inhibitors: NIM811 (Novartis) and DEBIO-025 (Debiopharm)

Methods of treatment include providing certain dosage amounts of a compound of the invention and at least one additional active agent to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the patient treated and the particular mode of administration. Dosage unit forms will generally contain between from about 1 mg to about 500 mg of each active agent. In certain embodiments 25 mg to 500 mg, or 25 mg to 200 mg of a compound of the invention are provided daily to a patient. When the additional active agent is NM 283 (valopicitabine), 100 mg to 1000 mg/day, or 200 mg to 800 mg/day, or 200 to 400 mg/day of either of those agents are typically provided to the patient. When the additional active agent is VX-950, 1000 mg to 3750 mg/day, or 1200 mg to 1800 mg/day are administered to the patient. Treatment regiments in which VX-950 is an additional active agent and about 350 to about 450 mg or about 700 to about 800 mg of VX-950 are administered to a patient three times per day or about 350 to about 450 mg or about 700 to about 800 mg is administered every 12 hours are particularly included in the invention.

EXAMPLES

General Methods

All nonaqueous reactions are performed under an atmosphere of dry argon gas (99.99%). NMR spectra are recorded at ambient temperature using a Bruker Avance 300 spectrometer ($^1$H at 300.1 MHz and $^{13}$C at 75.5 MHz). The chemical shifts for $^1$H and $^{13}$C are reported in parts per million (δ) relative to external tetramethylsilane and are referenced to signals of residual protons in the deuterated solvent. Analytical HPLC is performed using a Waters X-bridge C18 150×4.6 mm 3.5 μm column with a 20-min linear gradient elution of increasing concentrations of acetonitrile in water (5 to 95%) containing 0.1% trifluoroacetic acid with a flow rate of 1.0 mL/min and UV detection at 254 nm. Low-resolution mass spectra are recorded on a Thermo Finnigan Surveyor MSQ instrument (operating in APCI mode) equipped with a Gilson liquid chromatograph. Unless noted otherwise, the quasi-molecular ions, [M+H]$^+$, observed in the low-resolution mass spectra are the base peaks.

This invention is further illustrated by the following examples that should not be construed as limiting.

Abbreviations

The following chemical abbreviations are used in Examples 1 to 3. Additional abbreviations used in these examples will be familiar to those of skill in the art of organic chemical synthesis.

| | |
|---|---|
| DCM | dichloromethane |
| DMF | dimethyl formamide |
| DMAP | dimethylamine pyridine |
| Et$_3$N | triethylamine |
| EtOH | Ethanol |
| TCDI | thiocarbonyl diimidazole |
| THF | tetrahydrofuran |
| TMSCHN$_2$ | trimethylsilyl diazomethane |

Example 1

Synthesis of N-(4-(Pentyloxy)-3-(Trifluoromethyl) Phenyl)-4-(Pyridin-3-Yl)Thiazol-2-Amine Step 1. Preparation of 2-bromo-1-(pyridin-3-yl)ethanone Bromine (17.2 g, 0.11 mol) is added dropwise to a cooled solution (0° C.) of 3-acetylpyridine (12.1 g, 0.1 mol) in acetic acid containing 33% HBr with vigorous stirring. The stirring mixture is allowed to warm to 40° C. and maintained at this temperature for 2 hrs and then heated to 75° C. After 2 hrs, the mixture is cooled and diluted with ether (400 ml) to precipitate the product, which is collected by filtration and washed with ether and acetone to give 4 HBr salt as white crystals, which can be used for next step reaction without further purification.

Step 2. Preparation of N-(4-(pentyloxy)-3-(trifluoromethyl) phenyl)-4-(pyridin-3-yl)thiazol-2-amine The reaction mixture of 4 HBr salt (2.87 g, 10 mmol) and thiourea 2 (3.07 g, 10 mmol) in ethyl acetate (20 ml) is heated to 70° C. and stirred overnight. The reaction mixture is cooled to ambient temperature, and precipitates form. The product is collected by filtration, washed with ether, dried in air to give the product 5 as light yellow crystals.

NMR (CDCl$_3$, δppm): 10.69 (1H, s), 9.30 (1H, d, J=1.8 Hz), 8.95 (1H, dt, J=1.5, 8.4 Hz), 8.86 (1H, d, J=8.4 Hz), 8.14 (2H, m), 7.93 (1H, s), 7.91 (1H, dd, J=2.7, 7.5 Hz), 7.21 (1H, d, J=7.5 Hz), 4.06 (2H, t, J=6.2 Hz), 1.70 (2H, m), 1.37 (4H, m), 0.88 (3H, t, J=6.9 Hz).

Example 2

Synthesis of 4-(6-((Dimethylamino)Methyl)Pyridin-3-Yl)-N-(4-(Pentyloxy)-3-(Trifluoromethyl)Phenyl) Thiazol-2-Amine

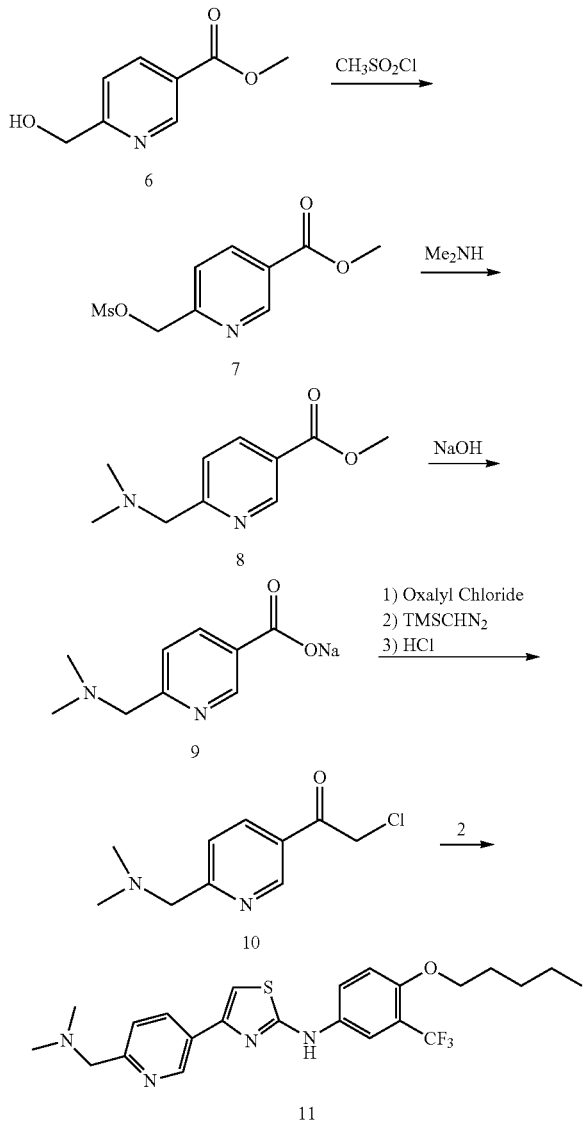

Step 1. Preparation of methyl 6-((methylsulfonyloxy)methyl) nicotinate

A Catalytic amount of DMAP (dimethylamine pyridine), triethylamine (2.0 g, 19.7 mmol) in 20 mL CH$_2$Cl$_2$, and methanesulfonyl chloride (1.95 g, 17.0 mmol) are added dropwise to a solution of 6-hydroxymethyl-nicotinic methyl ester 6 (2.2 g, 13.1 mmol), at −78° C. under argon. The mixture is stirred for 5 hours at −78° C. and then quenched with 30 mL saturated aqueous sodium bicarbonate. The organic layer is collected and the water phase extracted with $CH_2Cl_2$ (2×30 mL). The organic phases are combined and washed with water. The $CH_2Cl_2$ solution is dried over $MgSO_4$ and concentrated to give compound 7, which is used without further purification.

Step 2. Preparation of 6-dimethylaminomethyl-nicotinic methyl ester

Compound 7 is treated with dimethylamine (2M) in methanol at 0° C. for 30 minutes. The reaction mixture is then raised to room temperature and stirred for 5 hours. The solvent is removed and the residue passed through silical gel (flashed with ethyl acetate-methanol 95:5) to afford 6-dimethylaminomethyl-nicotinic methyl ester 8.

1HNMR ($CDCl_3$, ppm) δ 9.13 (1H), 8.24 (1H), 7.48 (1H), 3.93 (3H), 3.66 (2H), 2.28 (6H).

Step 3. Preparation of 6-dimethylaminomethyl-nicotinic Na Salt 6-dimethylaminomethyl-nicotinic methyl ester 8 (1.75 g, 9.0 mmol) is dissolved in 15 mL methanol; 5 mL 2 N sodium hydroxide is added. The mixture is heated at 90° C. for 1.5 hours and then quickly cooled to room temperature. The solvent is removed under vacuum and the remaining residue is dried by co-evaporated toluene. The solid is used without further purification. A small portion of sample is prepared for analytical use by acidification with 1N HCl, removal of water and drying.

$^1$HNMR ($D_2O$, ppm) δ 8.86 (1H), 8.16 (1H), 7.46 (1H), 4.05 (2H), 2.53 (6H).

Step 4. Preparation of chloroacetyl pyridine 6-dimethylaminomethyl-nicotinic Na salt 9 (202 mg, 1 mmol) is suspended in 8 mL $CH_2Cl_2$ and 2 drops of DMF is added. The mixture is treated with oxalyl chloride (1.2 mmol) at 0° C. and then warmed to room temperature and allowed to remain at this temperature 1.5 hours. The solvent is removed and the residue suspended in 10 mL THF. $Et_3N$ (2.2 mmol) is added, followed by $TMSCHN_2$ (2.5 mmol, 2M solution in ether) which is added at 0° C. The mixture is warmed to room temperature and stirred overnight. The mixture is then cooled to 0° C. and HCl (4.0 mmol, 2M in ether) is added. The mixture is stirred for 2 hrs at 0° C. and then the solvent is removed. The residue is diluted with $CH_2Cl_2$ (30 mL), neutralized with 10% aqueous $NaHCO_3$. The organic phase is collected and washed with water. The solvent is dried over $MgSO_4$ and concentrated to give chloroacetyl pyridine 10, which is used directly in the next step.

Step 5. Preparation of 4-(6-((dimethylamino)methyl)pyridin-3-yl)-N-(4-(pentyloxy)-3-(trifluoromethyl)phenyl)thiazol-2-amine The mixture of 10 with thiourea 2 (0.3 mmol) in 10 mL ethyl alcohol is refluxed for 2 hours and cooled to room temperature. The solvent is removed and the residue purified by HPLC to give the title compound 11.

$^1$HNMR ($CDCl_3$, ppm) δ 8.96 (1H), 8.03 (1H, dd, J=2.2, 8.1 Hz), 7.64 (1H), 7.55 (1H, dd, J=2.7, 8.9 Hz), 7.38 (1H, d, J=8.1 Hz), 7.16 (1H), 6.94 (1H, d, J=8.8 Hz), 6.84 (1H), 3.97 (2H, t, J=6.4 Hz), 3.66 (2H), 2.33 (6H), 1.76 (2H, m), 1.37 (m, 4H), 0.87 (3H, t, J=7.1 Hz).

Example 3

Synthesis OF 5-Fluoro-N-(4-Octyl-3-(Trifluoromethyl)Phenyl)-4-(Pyridin-3-Yl)Thiazol-2-Amine

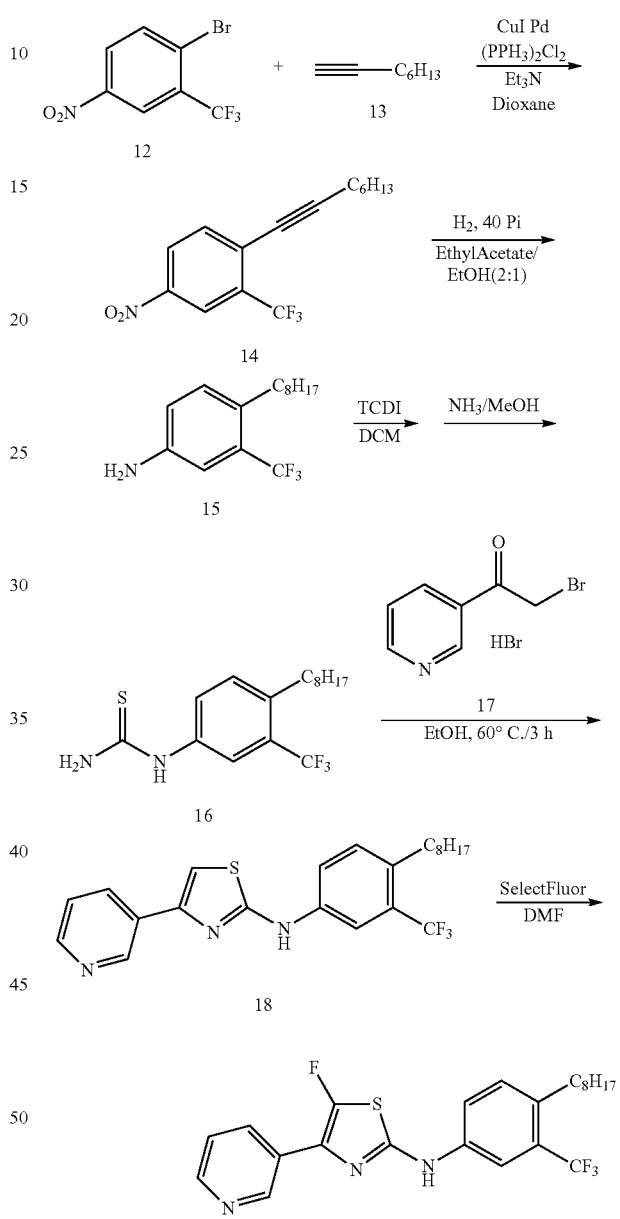

Step 1. Preparation of 4-nitro-1-(oct-1-ynyl)-2-(trifluoromethyl)benzene

A mixture of 12 (1-Bromo-4-nitro-2-trifluoromethyl-benzene, 10.8 g, 40 mmol), 13 (Oct-1-yne, 6.6 g, 60 mmol), CuI (1.52 g, 8 mmol), Pd(PPh$_3$)$_2$Cl$_2$ (1.8 g), Et$_3$N (22 ml, 160 mmol), and dioxane (22 ml) in a sealed tube under Ar is heated at 100° C. for 16 h. After cooling to rt, the mixture is filtered through celite, and washed with ethyl acetate. The filtrate is concentrated and purified by silica gel column chromatography (Ethyl acetate:Hexane=1:7) to give crude 14 as an oil.

Step 2: Preparation of 4-octyl-3-(trifluoromethyl)aniline

The crude 14 is dissolved in a mixed solvents of ethyl acetate and ethanol (40 ml/20 ml), and 10% Pd/C (1 g) is added, the mixture is hydrogenated under 40 psi at rt for 16 h. The mixture is then filtered through celite and washed with ethyl acetate. The filtrate is concentrated to give crude 15 (10.6 g).

Step 3: Preparation of 1-(4-octyl-3-(trifluoromethyl)phenyl)thiourea

A solution of crude 15 (10.6 g) in anhydrous $CH_2Cl_2$ (50 ml) at 0° C. is added dropwise to a solution of TCDI (14 g, 78 mmol) in anhydrous $CH_2Cl_2$ (250 ml). After addition, the mixture is warmed to rt and stirred for 3 h. The mixture is cooled to 0° C., ammonia (7N in MeOH, 50 ml) is added dropwise. After addition, the mixture is warmed to rt and stirred for 16 h. After concentration, water 300 ml is added and stirred for 1 h, the solid is filtered and washed by water. The desired product 16 is dried in vacuum to give a white solid (11 g).

Step 4. Preparation of N-(4-octyl-3-(trifluoromethyl)phenyl)-4-(pyridin-3-yl)thiazol-2-amine A mixture of 16 (13.3 g, 40 mmol) and 17 (prepared as described below) (12.36 g, 44 mmol) in ethanol (200 ml) is heated at 60° C. for 3 h, the mixture is adjusted to pH=7~8, with concentrated ammonium hydroxide followed by addition of water (200 ml), the solid is collected by filtration and recrystallized by ethanol to give 13.3 of 18.

Step 5: Synthesis of 5-fluoro-N-(4-octyl-3-(trifluoromethyl)phenyl)-4-(pyridin-3-yl)thiazol-2-amine SelectFlour (5.32 g, 15 mmol) is added in one portion to a solution of 18 (6.5, 15 mmol) in anhydrous DMF (60 ml) at 0° C. and the mixture is slowly warmed to rt in 2 h and stirred for additional 24 h. A $NH_3$/MeOH-solution and $H_2O$ was added while rapidly stirring and stirring continued for 48 hours. After water (60 ml) was added, the solid is filtered off and dried, purified by silica gel column chromatography (Ethyl acetate/Hexane=1:1) to give the desired product as a white solid: 5.2 g. (75% yield)

Preparation of Compound 17.

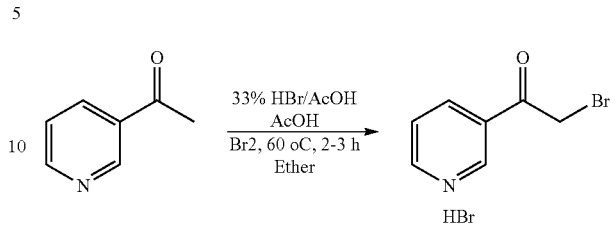

Acetylpyridine (120 g) is added to 33% HBr/AcOH (600 ml) with stirring (If the salt precipitated you can add more AcOH, 800 ml). Bromine (176 g) is added and the reaction mixture is heated to 60° C. for 2-3 h. The solution is cooled and ether (1400 ml) is added. The solid is filtered, washed with ether and dried to give the bromo compound, 17, in quantitative yield.

Example 4

Additional Exemplified Compounds

The compounds shown in Table I (TABLE OF COMPOUNDS) are prepared by the methods given in Examples 1 to 3. Variations to these methods may be necessary to obtain certain compounds shown in Table I. Such variations are routine in the art of synthetic organic chemistry and are readily apparent to those of skill in the art. In Table I +++ indicates inhibition of HCV replicon replication of less than 1 micromolar, ++ indicates inhibition of less than 10 micromolar to 1 micromolar, and + indicates inhibition greater than 10 micromolar.

TABLE I
TABLE OF COMPOUNDS

| Cmp # | Structure | Name | Activity | rt | M + 1 |
|---|---|---|---|---|---|
| 20 | 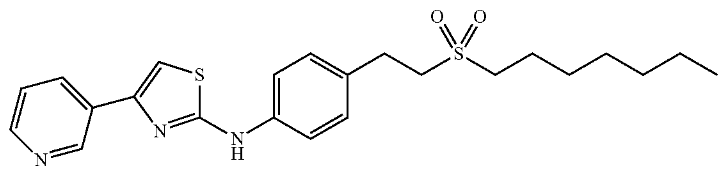 | N-(4-(2-(heptylsulfonyl)ethyl)phenyl)-4-(pyridin-3-yl)thiazol-2-amine | ++ | | |
| 21 | 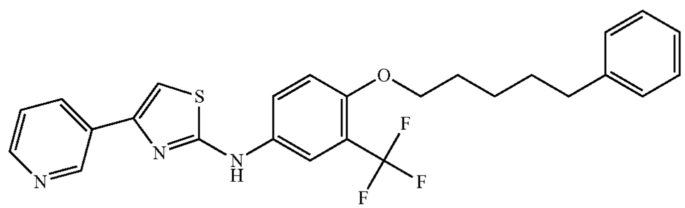 | N-(4-(5-phenylpentyloxy)-3-trifluoromethyl)phenyl)-4-(pyridin-3-yl)thiazol-2-amine | +++ | | |
| 22 | 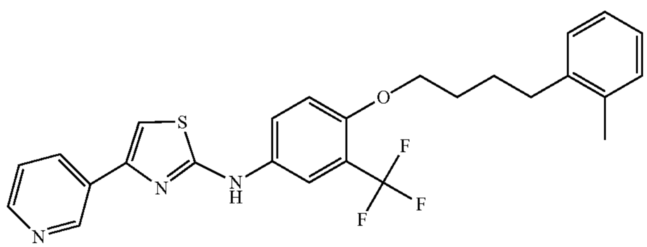 | 4-(pyridin-3-yl)-N-(4-(4-o-tolylbutoxy)-3-(trifluoromethyl)phenyl)thiazol-2-amine | +++ | | |
| 23 | 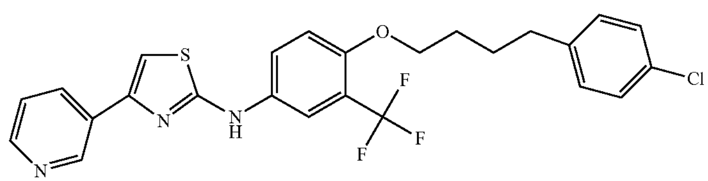 | N-(4-(4-(4-chlorophenyl)butoxy)-3-(trifluoromethyl)phenyl)-4-(pyridin-3-yl)thiazol-2-amine | +++ | | |

TABLE I-continued

TABLE OF COMPOUNDS

| Cmp # | Structure | Name | Activity | rt | M + 1 |
|---|---|---|---|---|---|
| 24 | 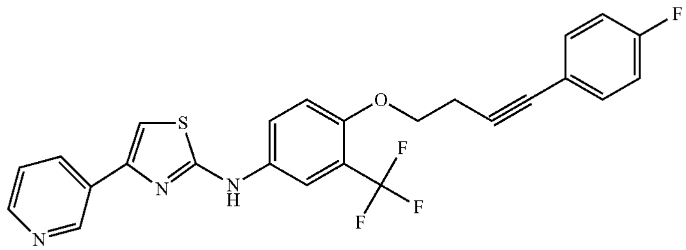 | N-(4-(4-(4-fluorophenyl)but-3-ynyloxy)-3-(trifluoromethyl)phenyl)-4-(pyridin-3-yl)thiazol-2-amine | +++ | | |
| 25 | 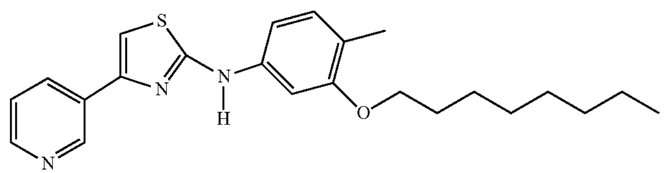 | N-(4-methyl-3-(octyloxy)phenyl)-4-(pyridin-3-yl)thiazol-2-amine | +++ | | |
| 26 | 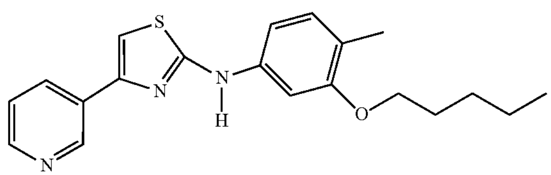 | N-(4-methyl-3-(pentyloxy)phenyl)-4-(pyridin-3-yl)thiazol-2-amine | +++ | | |
| 27 | 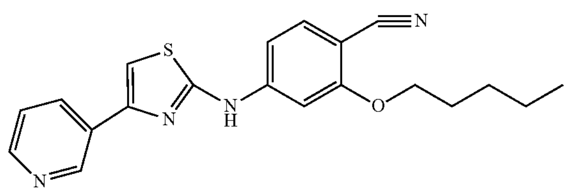 | 2-(pentyloxy)-4-(4-(pyridin-3-yl)thiazol-2-ylamino)benzonitrile | +++ | | |
| 28 | 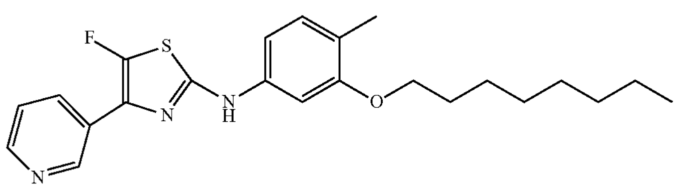 | 5-fluoro-N-(4-methyl-3-(octyloxy)phenyl)-4-(pyridin-3-yl)thiazol-2-amine | +++ | 2.11 | 414 |

TABLE 1-continued

TABLE OF COMPOUNDS

| Cmp # | Structure | Name | Activity | rt | M + 1 |
|---|---|---|---|---|---|
| 29 | 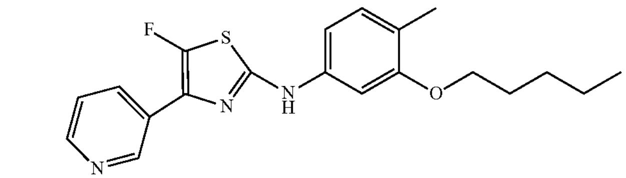 | 5-fluoro-N-(4-methyl-3-pentyloxyphenyl)-4-pyridin-3-yl)thiazol-2-amine | +++ | 1.64 | 372 |
| 30 | 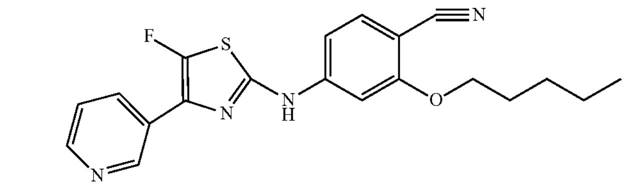 | -(5-fluoro-4-(pyridin-3-yl)thiazol-2-ylamino)-2-(pentyloxy)benzonitrile | +++ | 1.39 | 383 |
| 31 | 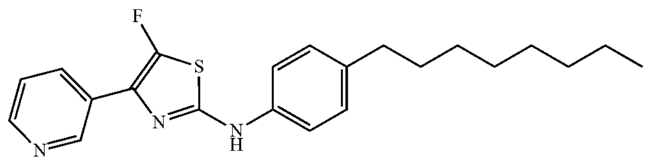 | 5-fluoro-N-(4-octylphenyl)-4-(pyridin-3-yl)thiazol-2-amine | +++ | 2.05 | 384 |
| 32 | 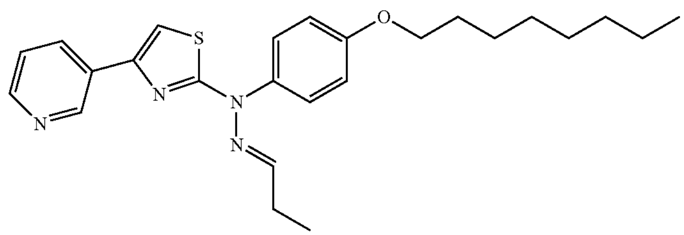 | (E)-2-(1-(4-(octyloxy)phenyl)-2-propylidenehydrazinyl)-4-(pyridin-3-yl)thiazole | +++ | 2.10 | 437 |
| 33 | 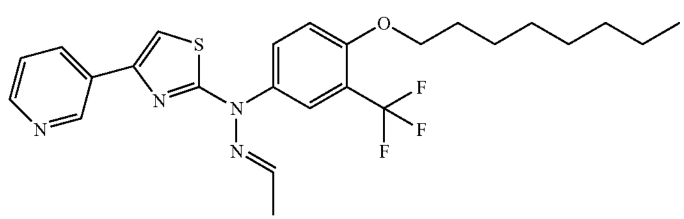 | (E)-2-(2-ethylidene-1-(4-(octyloxy)-3-(trifluoromethyl)phenyl)hydrazinyl)-4-(pyridin-3-yl)thiazole | +++ | 2.03 | 491 |

TABLE 1-continued

TABLE OF COMPOUNDS

| Cmp # | Structure | Name | Activity | rt | M + 1 |
|---|---|---|---|---|---|
| 34 | 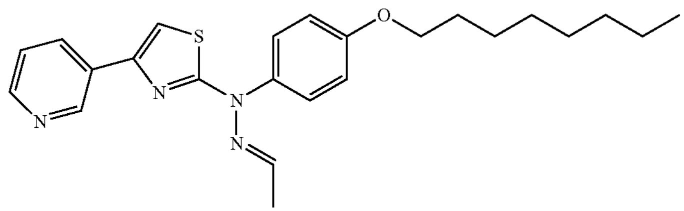 | (E)-2-(2-ethylidene-1-(4-(octyloxy)phenyl)hydrazinyl)-4-(pyridin-3-yl)thiazole | +++ | 2.03 | 423 |
| 35 | 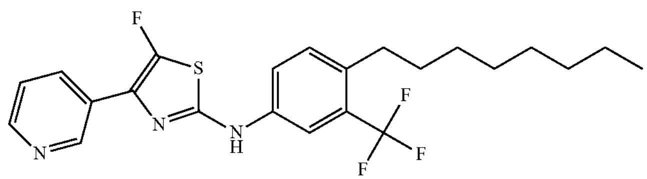 | 5-fluoro-N-(4-octyl-3-(trifluoromethyl)phenyl)-4-(pyridin-3-yl)thiazol-2-amine | +++ | 2.15 | 452 |
| 36 | 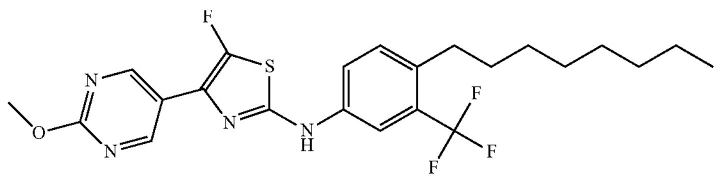 | 5-fluoro-4-(2-methoxypyrimidin-5-yl)-N-(4-octyl-3-(trifluoromethyl)phenyl)thiazol-2-amine | +++ | 3.89 | 483 |
| 37 | 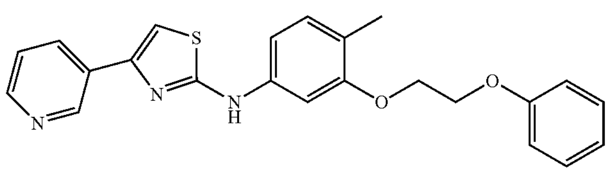 | N-(4-methyl-3-(2-phenoxyethoxy)phenyl)-4-(pyridin-3-yl)thiazol-2-amine | +++ | 1.46 | 404 |
| 38 | 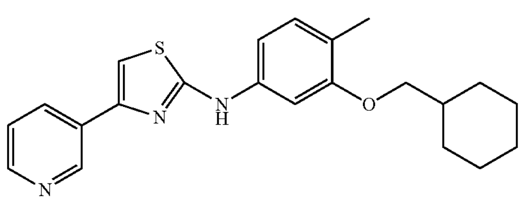 | N-(3-(cyclohexylmethoxy)-4-methylphenyl)-4-(pyridin-3-yl)thiazol-2-amine | +++ | 1.74 | 380 |

TABLE I-continued
TABLE OF COMPOUNDS
| Cmp # | Structure | Name | Activity | rt | M + 1 |
|---|---|---|---|---|---|
| 39 | 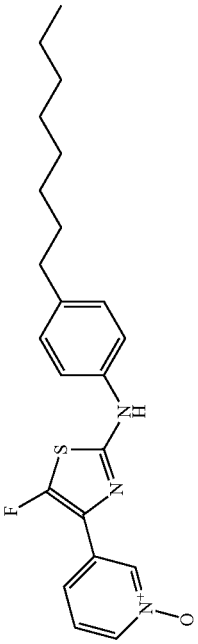 | 5-fluoro-N-(4-octylphenyl)-4-(pyridine-1-oxide-3-yl)thiazol-2-amine | +++ | 2.66 | 400 |
| 40 | 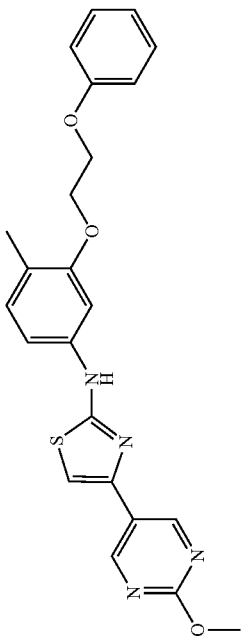 | 4-(2-methoxypyrimidin-5-yl)-N-(4-methyl-3-(2-phenoxyethoxy)phenyl)thiazol-2-amine | +++ | 2.24 | 435 |
| 41 | 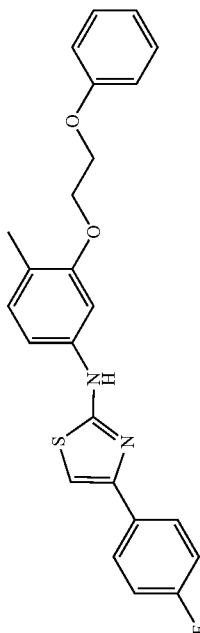 | 4-(4-fluorophenyl)-N-(4-methyl-3-2-phenoxyethoxy)phenyl)thiazol-2-amine | +++ | 2.50 | 421 |
| 42 | 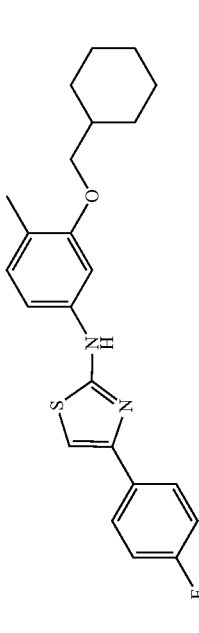 | N-(3-(cyclohexylmethoxy)-4-methylphenyl)-4-(4-fluorophenyl)thiazol-2-amine | +++ | 3.24 | 397 |

TABLE 1-continued

TABLE OF COMPOUNDS

| Cmp # | Structure | Name | Activity | rt | M + 1 |
|---|---|---|---|---|---|
| 43 | 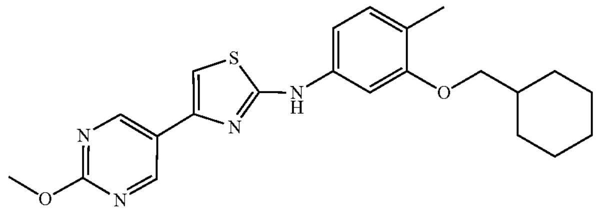 | N-(3-(cyclohexylmethoxy)-4-methylphenyl)-4-(2-methoxypyrimidin-5-yl)thiazol-2-amine | +++ | 2.89 | 411 |
| 44 | 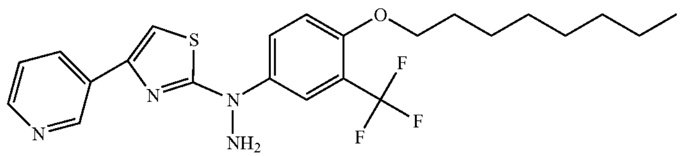 | 2-(1-(4-(octyloxy)-3-(trifluoromethyl)phenyl)hydrazinyl)-4-(pyridin-3-yl)thiazolo | +++ | 2.12 | 465 |
| 45 | 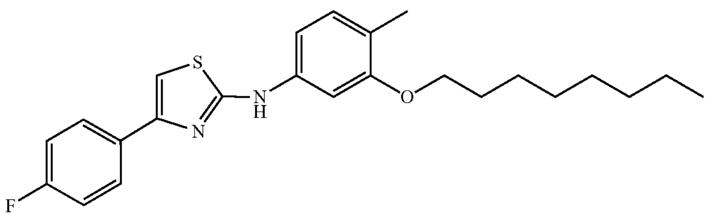 | 4-(4-fluorophenyl)-N-(4-methyl-3-(octyloxy)phenyl)thiazol-2-amine | +++ | 3.61 | 413 |
| 46 | 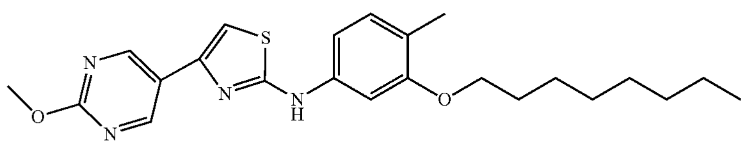 | 4-(2-methoxypyrimidin-5-yl)-N-(4-methyl-3-(octyloxy)phenyl)thiazol-2-amine | +++ | 3.27 | 427 |
| 47 | 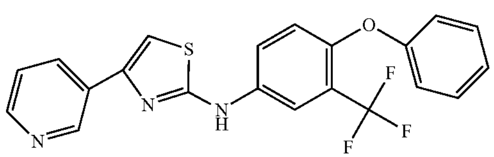 | N-(4-phenoxy-3-(trifluoromethyl)phenyl)-4-(pyridin-3-yl)thiazol-2-amine | +++ | 1.43 | 414 |

TABLE 1-continued

TABLE OF COMPOUNDS

| Cmp # | Structure | Name | Activity | rt | M + 1 |
|---|---|---|---|---|---|
| 48 | 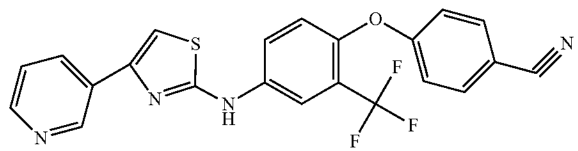 | 4-(4-(pyridin-3-yl)thiazol-2-ylamino)-2-(trifluoromethyl)phenoxy)benzonitrile | +++ | 1.32 | 439 |
| 49 | 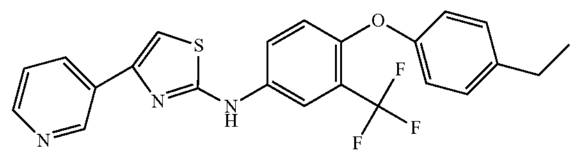 | N-(4-(4-ethylphenoxy)-3-(trifluoromethyl)phenyl)-4-(pyridin-3-yl)thiazol-2-amine | +++ | 1.64 | 442 |
| 50 | 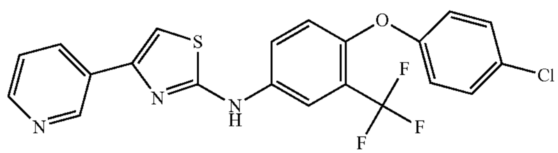 | N-(4-(4-chlorophenoxy)-3-(trifluoromethyl)phenyl)-4-(pyridin-3-yl)thiazol-2-amine | +++ | 1.54 | 448 |
| 51 | 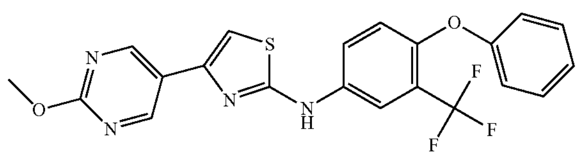 | 4-(2-methoxypyrimidin-5-yl)-N-(4-phenoxy-3-(trifluoromethyl)phenyl)thiazol-2-amine | +++ | 2.30 | 445 |
| 52 | 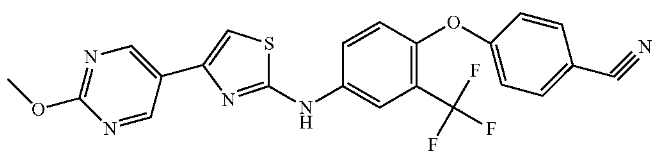 | 4-(4-(2-methoxypyrimidin-5-yl)thiazol-2-ylamino)-2-(trifluoromethyl)phenoxy)benzonitrile | +++ | 2.14 | 470 |
| 53 | 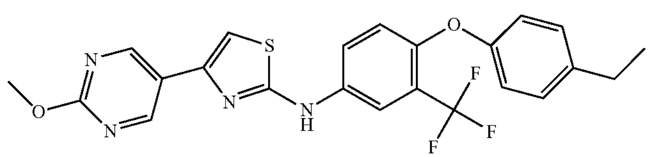 | N-(4-(4-ethylphenoxy)-3-(trifluoromethyl)phenyl)-4-(2-methoxypyrimidin-5-yl)thiazol-2-amine | +++ | 2.56 | 473 |

TABLE I-continued

TABLE OF COMPOUNDS

| Cmp # | Structure | Name | Activity | rt | M + 1 |
|---|---|---|---|---|---|
| 54 | 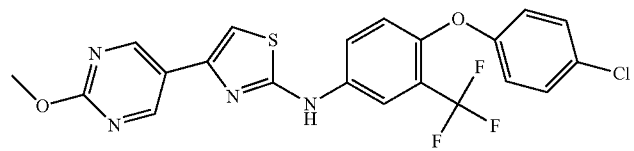 | N-(4-(4-chlorophenoxy)-3-(trifluoromethyl)phenyl)-4-(2-methoxypyrimidin-5-yl)thiazol-2-amine | +++ | 2.49 | 479 |
| 55 | 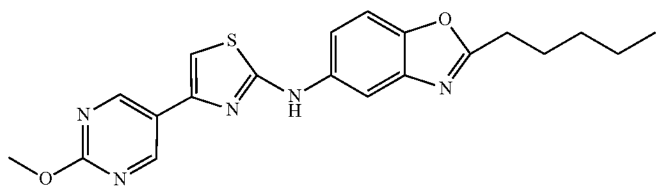 | N-(4-(2-methoxypyrimidin-5-yl)thiazol-2-yl)-2-pentylbenzo[d]oxazol-5-amine | +++ | 2.21 | 396 |
| 56 | 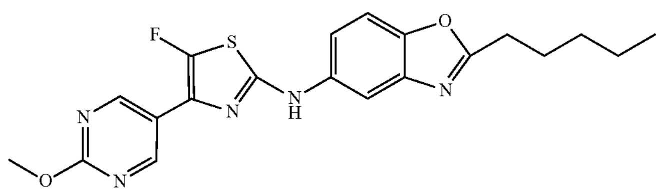 | N-(5-fluoro-4-(2-methoxypyrimidin-5-yl)thiazol-2-yl)-2-pentylbenzo[d]oxazol-5-amine | +++ | 2.36 | 414 |
| 57 | 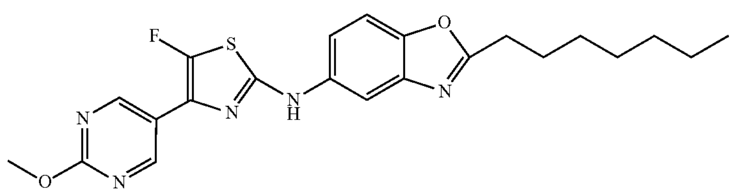 | N-(5-fluoro-4-(2-methoxypyrimidin-5-yl)thiazol-2-yl)-2-heptylbenzo[d]oxazol-5-amine | +++ | 2.75 | 442 |
| 58 | 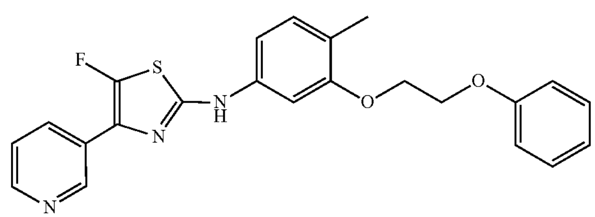 | 5-fluoro-N-(4-methyl-3-(2-phenoxyethoxy)phenyl)-4-(pyridin-3-yl)thiazol-2-amine | +++ | 1.51 | 422 |

TABLE 1-continued

TABLE OF COMPOUNDS

| Cmp # | Structure | Name | Activity | rt | M + 1 |
|---|---|---|---|---|---|
| 59 | 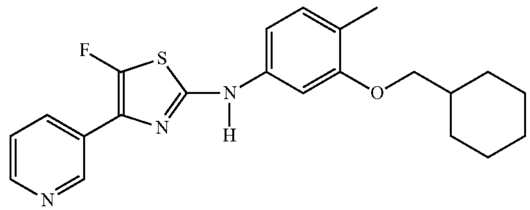 | N-(3-(cyclohexylmethoxy)-4-methylphenyl)-5-fluoro-4-(pyridin-3-yl)thiazol-2-amine | +++ | 1.88 | 398 |
| 60 | 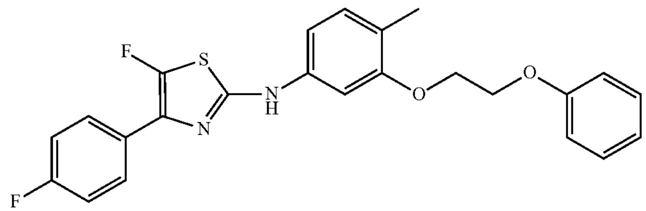 | 5-fluoro-4-(4-fluorophenyl)-N-(4-methyl-3-(2-phenoxyethoxy)phenyl)thiazol-2-amine | +++ | 2.97 | 439 |
| 61 | 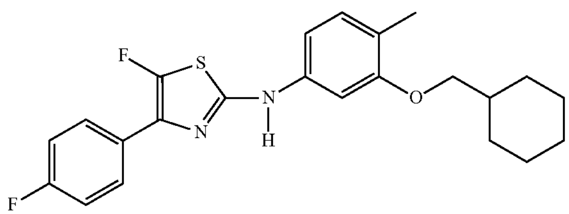 | N-(3-(cyclohexylmethoxy)-4-methylphenyl)-5-fluoro-4-(4-fluorophenyl)thiazol-2-amine | +++ | 3.95 | 415 |
| 62 | 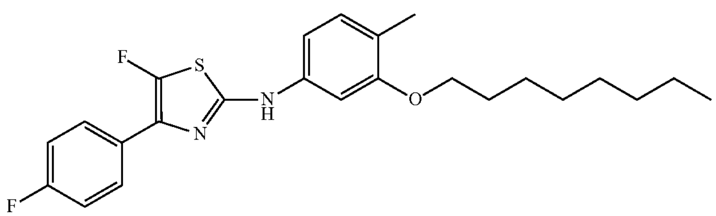 | 5-fluoro-4-(4-fluorophenyl)-N-(4-methyl-3-(octyloxy)phenyl)thiazol-2-amine | +++ | 4.32 | 431 |

TABLE I-continued

TABLE OF COMPOUNDS

| Cmp # | Structure | Name | Activity | rt | M + 1 |
|---|---|---|---|---|---|
| 63 | 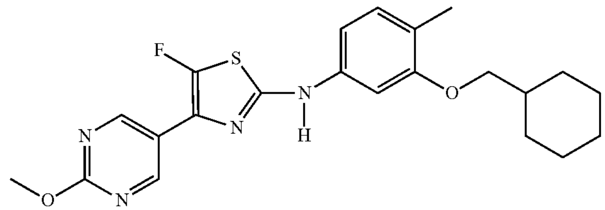 | N-(3-(cyclohexylmethoxy)-4-methylphenyl)-5-fluoro-4-(2-methoxypyrimidin-5-yl)thiazol-2-amine | +++ | 3.31 | 429 |
| 64 | 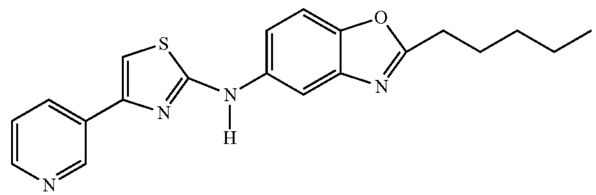 | 2-pentyl-N-(4-pyridin-3-yl)thiazol-2-yl)benzo[d]oxazol-5-amine | +++ | 1.42 | 365 |
| 65 | 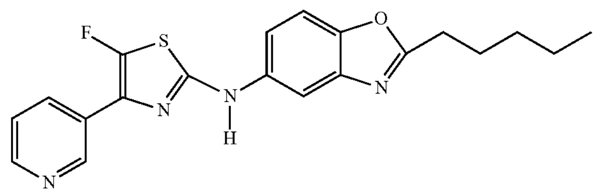 | N-(5-fluoro-4-(pyridin-3-yl)thiazol-2-yl)-2-pentylbenzo[d]oxazol-5-amine | +++ | 1.30 | 383 |
| 66 | 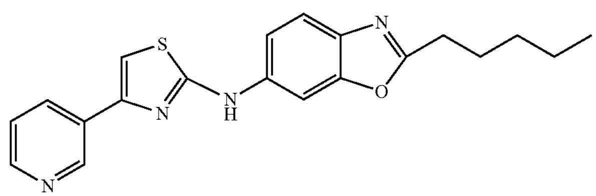 | 2-pentyl-N-(4-(pyridin-3-yl)thiazol-2-yl)benzo[d]oxazol-6-amine | +++ | 1.15 | 365 |
| 67 | 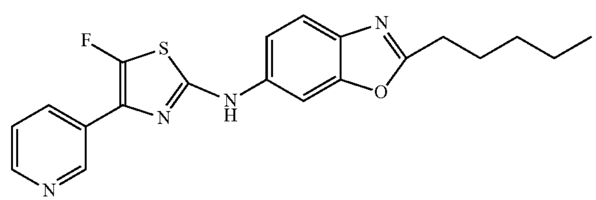 | N-(5-fluoro-4-(pyridin-3-yl)thiazol-2-yl)-2-pentylbenzo[d]oxazol-6-amine | +++ | 1.26 | 383 |

TABLE I-continued

TABLE OF COMPOUNDS

| Cmp # | Structure | Name | Activity | rt | M + 1 |
|---|---|---|---|---|---|
| 68 | 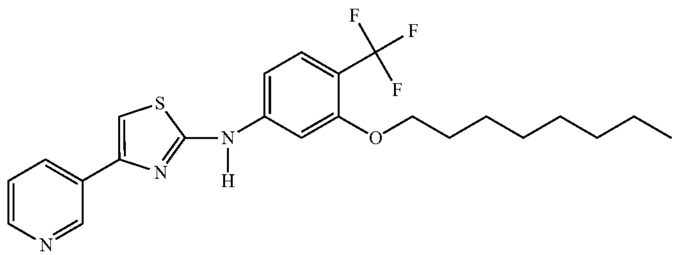 | N-(3-(octyloxy)-4-(trifluoromethyl)phenyl)-4-(pyridin-3-yl)thiazol-2-amine | +++ | 1.95 | 450 |
| 69 | 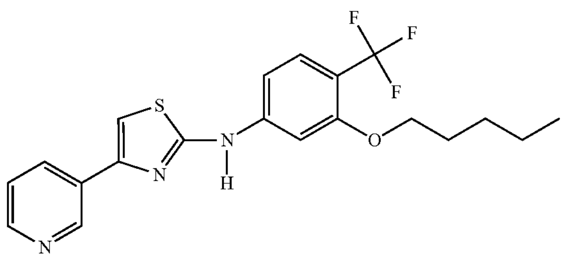 | N-(3-(pentyloxy)-4-(trifluoromethyl)phenyl)-4-(pyridin-3-yl)thiazol-2-amine | +++ | 1.56 | 408 |
| 70 | 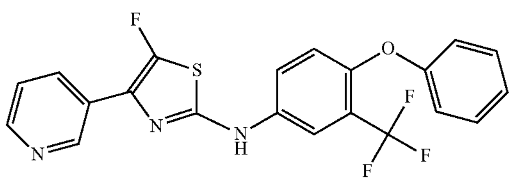 | 5-fluoro-N-(4-phenoxy-3-(trifluoromethyl)phenyl)-4-(pyridin-3-yl)thiazol-2-amine | +++ | 1.43 | 432 |
| 71 | 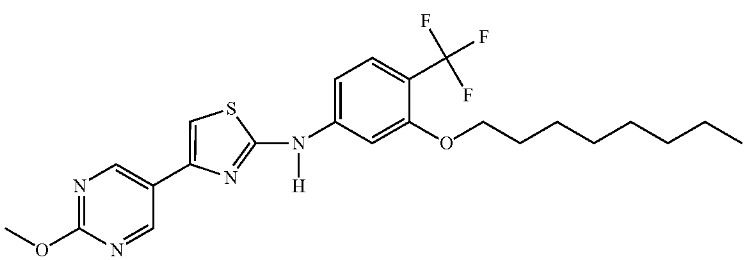 | 4-(2-methoxypyrimidin-5-yl)-N-(3-(octyloxy)-4-(trifluoromethyl)phenyl)thiazol-2-amine | +++ | 3.18 | 481 |

TABLE I-continued

TABLE OF COMPOUNDS

| Cmp # | Structure | Name | Activity | rt | M + 1 |
|---|---|---|---|---|---|
| 72 | 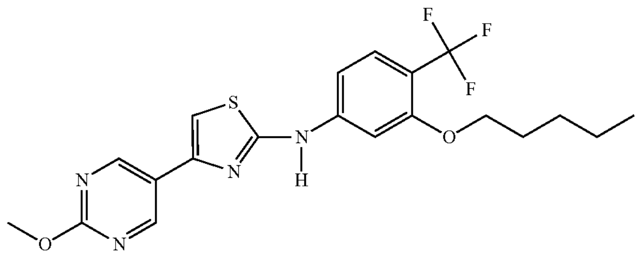 | 4-(2-methoxypyrimidin-5-yl)-N-(3-(pentyloxy)-4-(trifluoromethyl)phenyl)thiazol-2-amine | +++ | 2.52 | 439 |
| 73 | 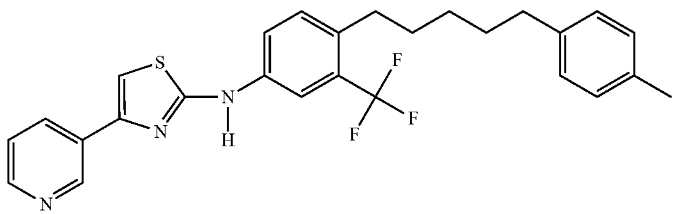 | 4-(pyridin-3-yl)-N-(4-(5-p-tolylpentyl)-3-(trifluoromethyl)phenyl)thiazol-2-amine | +++ | 2.01 | 482 |
| 74 | 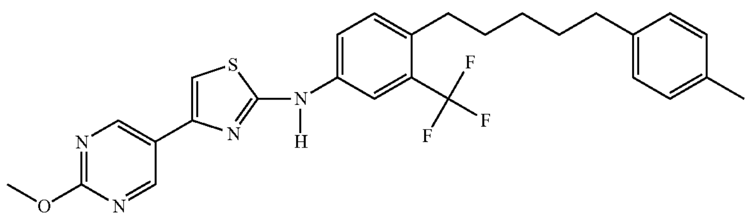 | 4-(2-methoxypyrimidin-5-yl)-N-(4-(5-p-tolylpentyl)-3-(trifluoromethyl)phenyl)thiazol-2-amine | +++ | 3.45 | 513 |
| 75 | 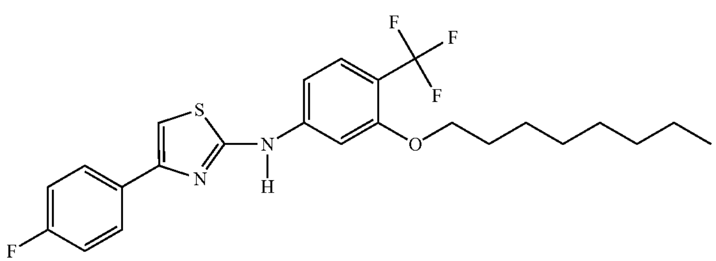 | 4-(4-fluorophenyl)-N-(3-(octyloxy)-4-(trifluoromethyl)phenyl)thiazol-2-amine | +++ | 4.15 | 467 |

TABLE 1-continued
TABLE OF COMPOUNDS
| Cmp # | Structure | Name | Activity | rt | M + 1 |
|---|---|---|---|---|---|
| 76 | 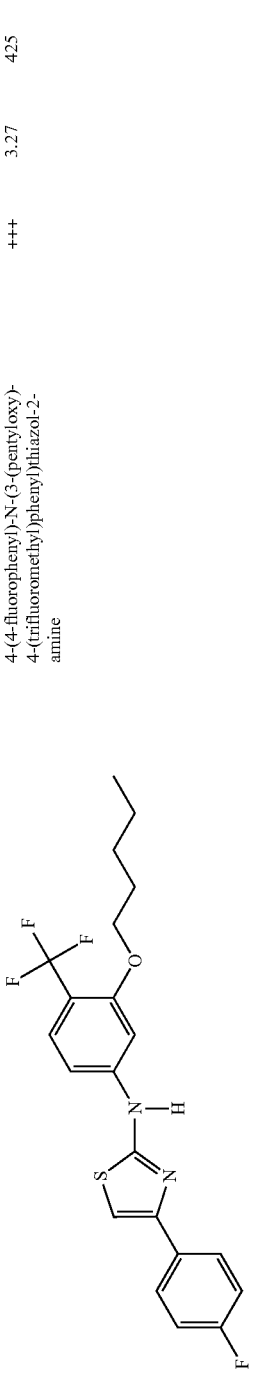 | 4-(4-fluorophenyl)-N-(3-(pentyloxy)-4-(trifluoromethyl)phenyl)thiazol-2-amine | +++ | 3.27 | 425 |
| 77 | 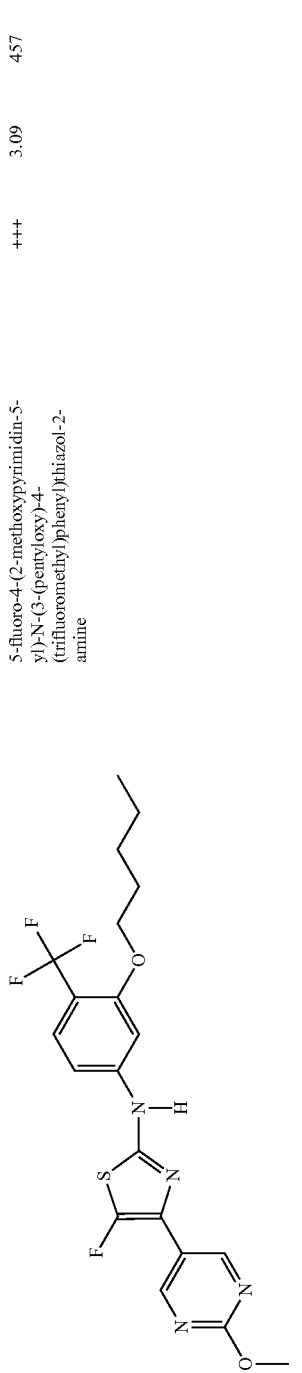 | 5-fluoro-4-(2-methoxypyrimidin-5-yl)-N-(3-(pentyloxy)-4-(trifluoromethyl)phenyl)thiazol-2-amine | +++ | 3.09 | 457 |
| 78 | 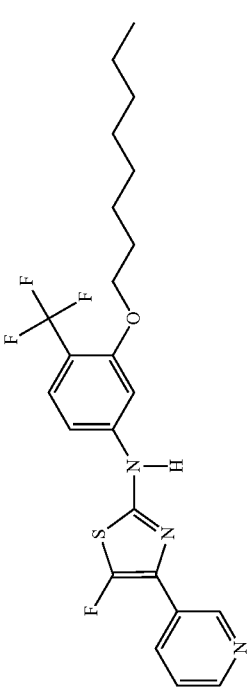 | 5-fluoro-N-(3-(octyloxy)-4-(trifluoromethyl)phenyl)-4-(pyridin-3-yl)thiazol-2-amine | +++ | 2.16 | 468 |

TABLE 1-continued
TABLE OF COMPOUNDS
| Cmp # | Structure | Name | Activity | rt | M + 1 |
|---|---|---|---|---|---|
| 79 | 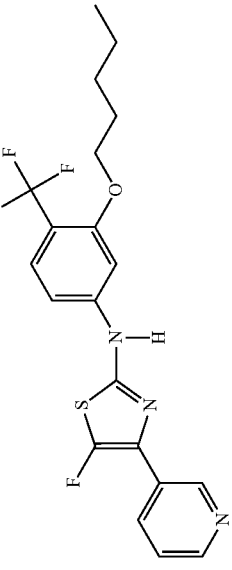 | 5-fluoro-N-(3-(pentyloxy)-4-(trifluoromethyl)phenyl)-4-(pyridin-3-yl)thiazol-2-amine | ++ | 1.71 | 426 |
| 80 | 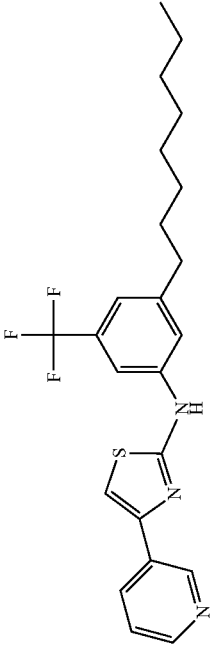 | N-(3-octyl-5-(trifluoromethyl)phenyl)-4-(pyridin-3-yl)thiazol-2-amine | +++ | 2.27 | 434 |
| 81 | 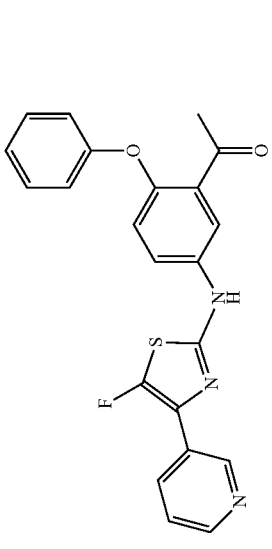 | 1-(5-(5-fluoro-4-(pyridin-3-yl)thiazol-2-ylamino)-2-phenoxyphenyl)ethanone | +++ | 1.39 | 406 |

TABLE I-continued

TABLE OF COMPOUNDS

| Cmp # | Structure | Name | Activity | rt | M + 1 |
|---|---|---|---|---|---|
| 82 | 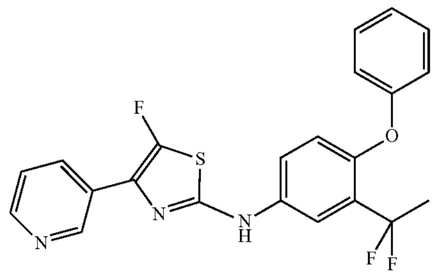 | N-(3-(1,1-difluoroethyl)-4-phenoxyphenyl)-5-fluoro-4-(pyridin-3-yl)thiazol-2-amine | +++ | 1.26 | 428.4 |
| 83 | 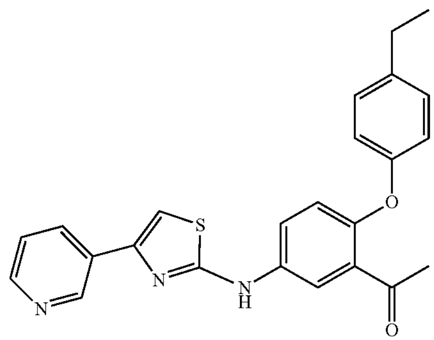 | 1-(2-(4-chlorophenoxy)-5-(4-(pyridin-3-yl)thiazol-2-ylamino)phenyl)ethanone | +++ | 1.57 | 416 |
| 84 | 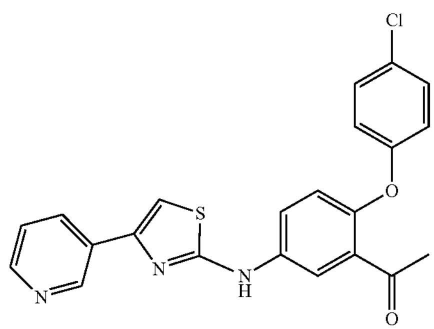 | 1-(2-(4-chlorophenoxy)-5-(4-(pyridin-3-yl)thiazol-2-ylamino)phenyl)ethanone | +++ | 1.47 | 422 |

TABLE 1-continued

TABLE OF COMPOUNDS

| Cmp # | Structure | Name | Activity | rt | M + 1 |
|---|---|---|---|---|---|
| 85 | 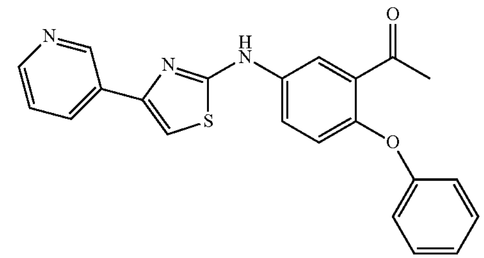 | 1-(2-phenoxy-5-(4-(pyridin-3-yl)thiazol-2-ylamino)phenyl)ethanone | +++ | 1.35 | 388 |
| 86 | 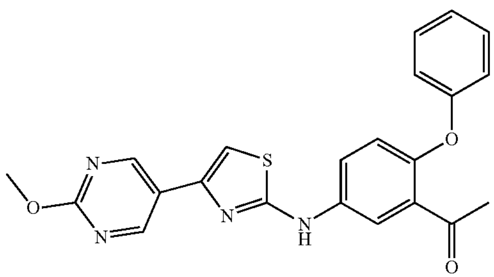 | 1-(5-(4-(2-methoxypyrimidin-5-yl)thiazol-2-ylamino)-2-phenoxyphenyl)ethanone | +++ | 2.11 | 419 |
| 87 | 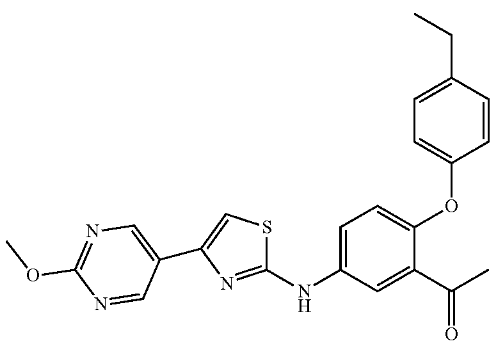 | 1-(2-(4-ethylphenoxy)-5-(4-(2-methoxypyrimidin-5-yl)thiazol-2-ylamino)phenyl)ethanone | +++ | 2.42 | 447 |

TABLE 1-continued

TABLE OF COMPOUNDS

| Cmp # | Structure | Name | Activity | rt | M + 1 |
|---|---|---|---|---|---|
| 88 | 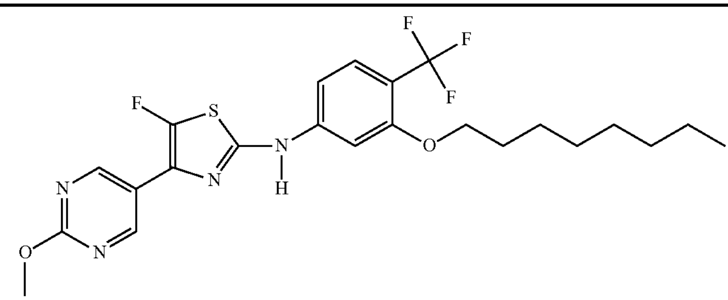 | 5-fluoro-4-(2-methoxypyrimidin-5-yl)-N-(3-(octyloxy)-4-(trifluoromethyl)phenyl)thiazol-2-amine | +++ | 3.93 | 499 |
| 89 | 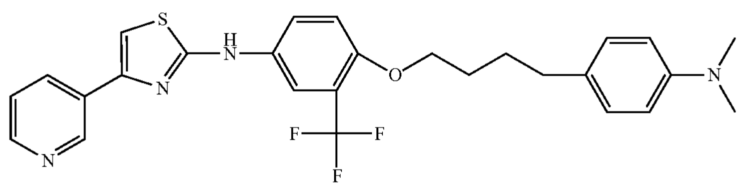 | N-(4-(4-(dimethylamino)phenyl)butoxy)-3-(trifluoromethyl)phenyl)-4-(pyridin-3-yl)thiazol-2-amine | +++ | 2.19 | 500 |
| 90 | 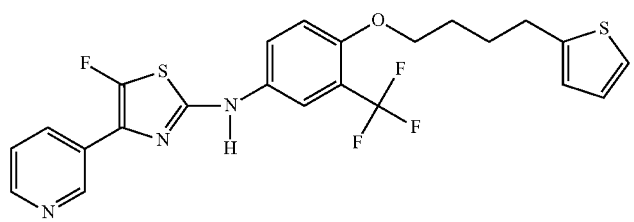 | 5-fluoro-4-(pyridin-3-yl)-N-(4-(4-(thiophen-2-yl)butoxy)-3-(trifluoromethyl)phenyl)thiazol-2-amine | +++ | 1.75 | 494 |
| 91 | 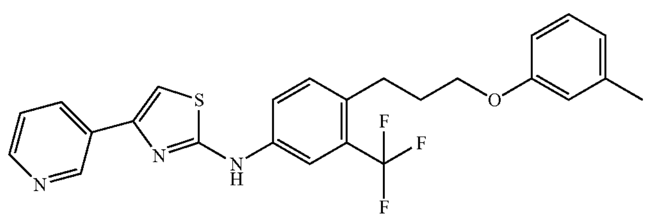 | 4-(pyridin-3-yl)-N-(4-(3-(m-tolyloxy)propyl)-3-(trifluoromethyl)phenyl)thiazol-2-amine | +++ | 1.82 | 470 |

TABLE I-continued

TABLE OF COMPOUNDS

| Cmp # | Structure | Name | Activity | rt | M + 1 |
|---|---|---|---|---|---|
| 92 | 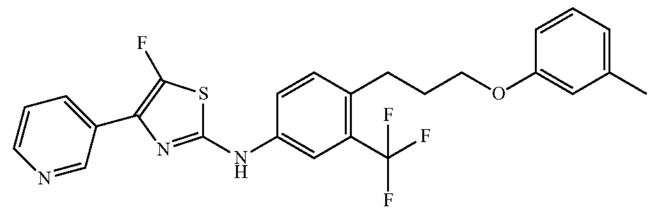 | 5-fluoro-4-(pyridin-3-yl)-N-(4-(3-(m-tolyloxy)propyl)-3-(trifluoromethyl)phenyl)thiazol-2-amine | +++ | 1.88 | 488 |
| 93 | 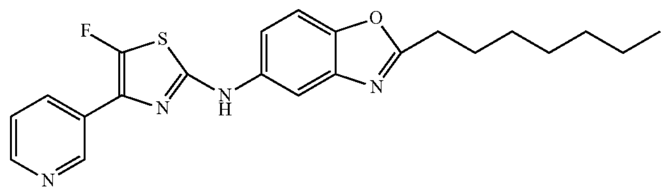 | N-(5-fluoro-4-(pyridin-3-yl)thiazol-2-yl)-2-heptylbenzo[d]oxazol-5-amine | +++ | 1.62 | 411.6 |
| 94 | 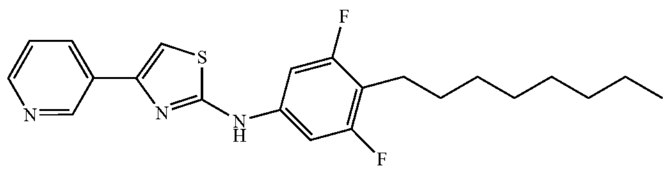 | N-(3,5-difluoro-4-octylphenyl)-4-(pyridin-3-yl)thiazol-2-amine | +++ | 1.95 | 402 |
| 95 | 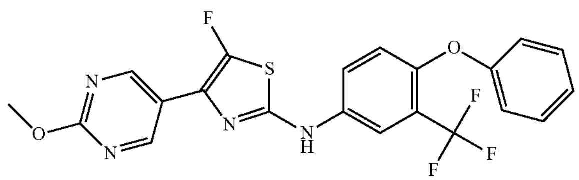 | 5-fluoro-4-(2-methoxypyrimidin-5-yl)-N-(4-phenoxy-3-(trifluoromethyl)phenyl)thiazol-2-amine | ++ | 2.59 | 463 |

TABLE 1-continued

TABLE OF COMPOUNDS

| Cmp # | Structure | Name | Activity | rt | M + 1 |
|---|---|---|---|---|---|
| 96 | 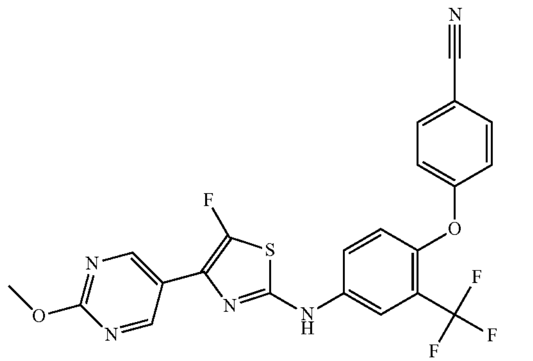 | 4-(4-(5-fluoro-4-(2-methoxypyrimidin-5-yl)thiazol-2-ylamino)-2-(trifluoromethyl)phenoxy)benzonitrile | +++ | 2.41 | 488 |
| 97 | 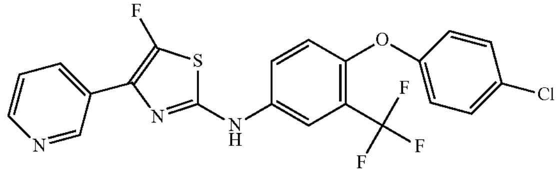 | N-(4-(4-chlorophenoxy)-3-(trifluoromethyl)phenyl)-5-fluoro-4-(pyridin-3-yl)thiazol-2-amine | +++ | 1.75 | 466 |
| 98 | 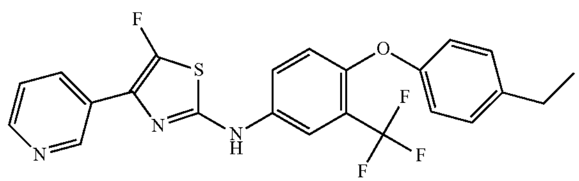 | N-(4-(4-ethylphenoxy)-3-(trifluoromethyl)phenyl)-5-fluoro-4-(pyridin-3-yl)thiazol-2-amine | +++ | 1.78 | 460 |
| 99 | 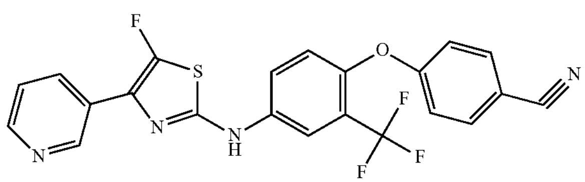 | 4-(4-(5-fluoro-4-(pyridin-3-yl)thiazol-2-ylamino)-2-(trifluoromethyl)phenoxy)benzonitrile | +++ | 1.49 | 457 |

TABLE I-continued

TABLE OF COMPOUNDS

| Cmp # | Structure | Name | Activity | rt | M + 1 |
|---|---|---|---|---|---|
| 100 | 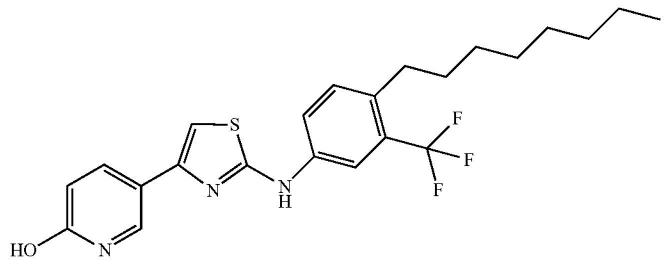 | 5-(2-(4-octyl-3-(trifluoromethyl)phenylamino)thiazol-4-yl)pyridin-2-ol | +++ | 2.76 | 450 |
| 101 | 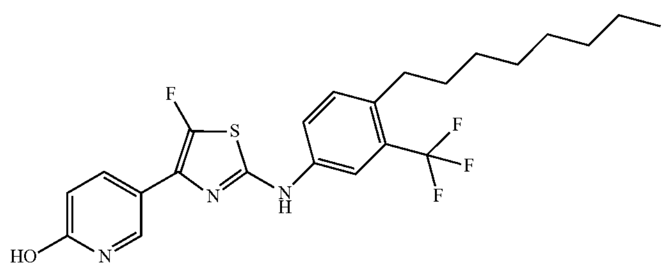 | 5-(5-fluoro-2-(4-octyl-3-(trifluoromethyl)phenylamino)thiazol-4-yl)pyridin-2-ol | +++ | 3.20 | 468 |
| 102 | 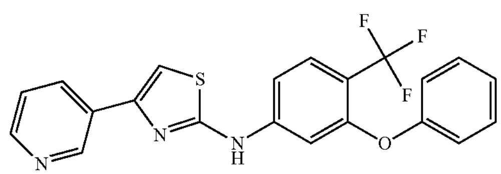 | N-(3-phenoxy-4-trifluoromethyl)phenyl)-4-(pyridin-3-yl)thiazol-2-amine | ++ | 1.43 | 414 |
| 103 | 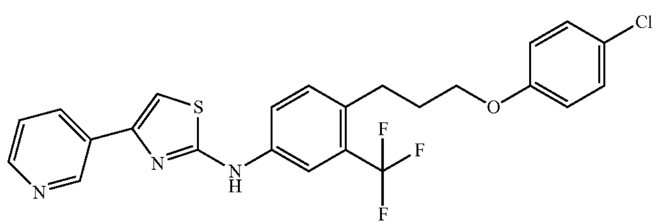 | N-(4-(3-(4-chlorophenoxy)propyl)-3-(trifluoromethyl)phenyl)-4-(pyridin-3-yl)thiazol-2-amine | +++ | 1.83 | 490 |

TABLE 1-continued

TABLE OF COMPOUNDS

| Cmp # | Structure | Name | Activity | rt | M + 1 |
|---|---|---|---|---|---|
| 104 | 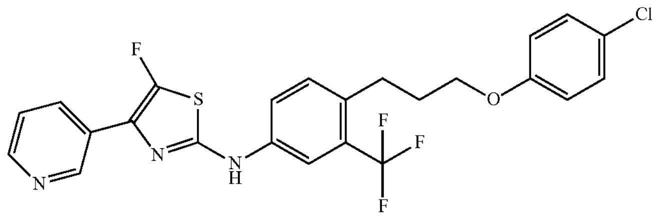 | N-(4-(3-(4-chlorophenoxy)propyl)-3-(trifluoromethyl)phenyl)-5-fluoro-4-(pyridin-3-yl)thiazol-2-amine | +++ | 1.96 | 508 |
| 105 | 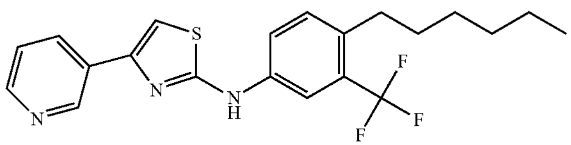 | N-(4-hexyl-3-(trifluoromethyl)phenyl)-4-(pyridin-3-yl)thiazol-2-amine | +++ | 1.89 | 406 |
| 106 | 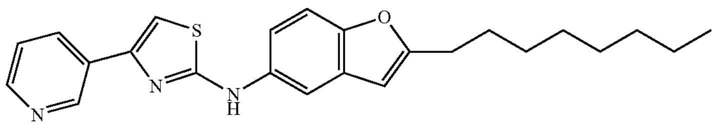 | N-(2-octylbenzofuran-5-yl)-4-(pyridin-3-yl)thiazol-2-amine | +++ | 2.08 | 406.6 |
| 107 | 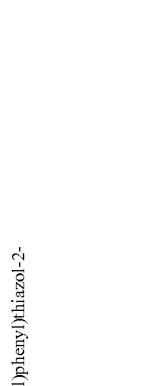 | 5-fluoro-4-(pyridin-3-yl)-N-(4-(4-p-tolylbutoxy)-3-(trifluoromethyl)phenyl)thiazol-2-amine | +++ | 1.90 | 502 |
| 108 | 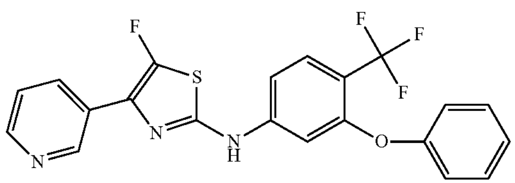 | 5-fluoro-N-(3-phenoxy-4-(trifluoromethyl)phenyl)-4-(pyridin-3-yl)thiazol-2-amine | +++ | 1.56 | 432 |

TABLE I-continued

TABLE OF COMPOUNDS

| Cmp # | Structure | Name | Activity | rt | M + 1 |
|---|---|---|---|---|---|
| 109 | 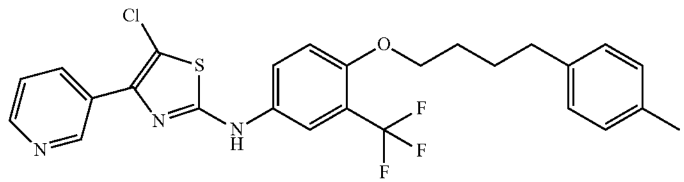 | 5-chloro-4-(pyridin-3-yl)-N-(4-(4-(p-tolyl)butoxy)-3-(trifluoromethyl)phenyl)thiazol-2-amine | +++ | 2.10 | 518 |
| 110 | 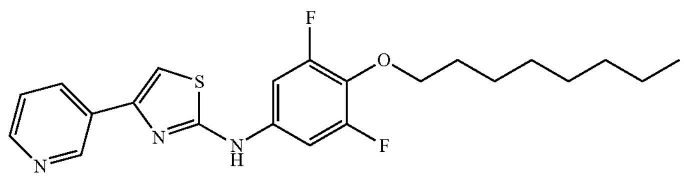 | N-(3,5-difluoro-4-(octyloxy)phenyl)-4-(pyridin-3-yl)thiazol-2-amine | +++ | 1.89 | 418 |
| 111 | 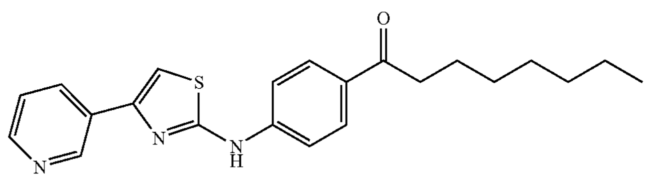 | 1-(4-(4-(pyridin-3-yl)thiazol-2-ylamino)phenyl)octan-1-one | +++ | 1.55 | 381 |
| 112 | 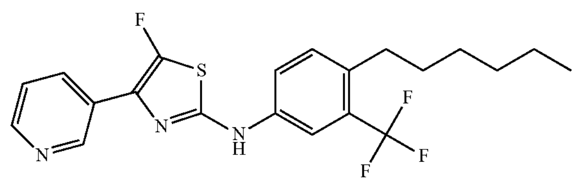 | 5-fluoro-N-(4-hexyl-3-(trifluoromethyl)phenyl)-4-(pyridin-3-yl)thiazol-2-amine | +++ | 2.02 | 424 |
| 113 | 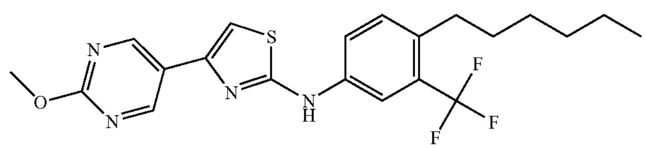 | N-(4-hexyl-3-(trifluoromethyl)phenyl)-4-(2-methoxypyrimidin-5-yl)thiazol-2-amine | +++ | 3.35 | 437 |

TABLE 1-continued

TABLE OF COMPOUNDS

| Cmp # | Structure | Name | Activity | rt | M + 1 |
|---|---|---|---|---|---|
| 114 | 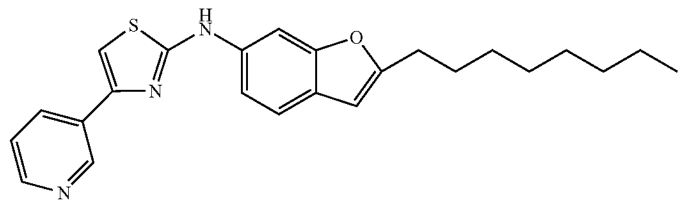 | N-(2-octylbenzofuran-6-yl)-4-(pyridin-3-yl)thiazol-2-amine | +++ | 2.08 | 406.6 |
| 115 | 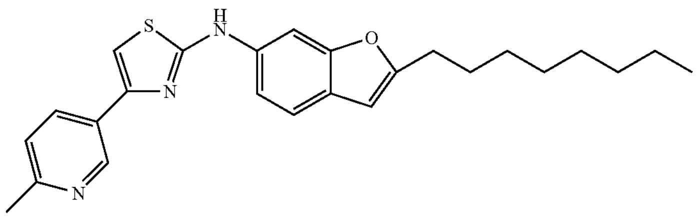 | 4-(6-methylpyridin-3-yl)-N-(2-octylbenzofuran-6-yl)thiazol-2-amine | +++ | 2.07 | 420 |
| 116 | 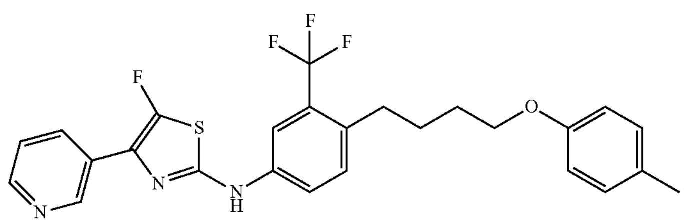 | 5-fluoro-4-(pyridin-3-yl)-N-(4-(4-(p-tolyloxy)butyl)-3-(trifluoromethyl)phenyl)thiazol-2-amine | +++ | 1.98 | 502 |
| 117 | 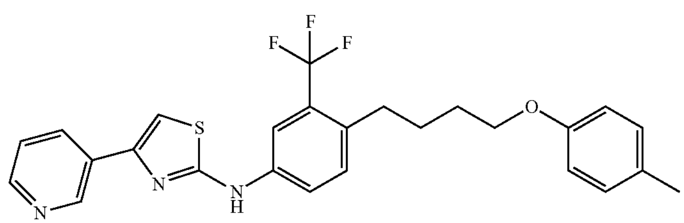 | 4-(pyridin-3-yl)-N-(4-(4-(p-tolyloxy)butyl)-3-(trifluoromethyl)phenyl)thiazol-2-amine | +++ | 1.92 | 484 |

TABLE I-continued

TABLE OF COMPOUNDS

| Cmp # | Structure | Name | Activity | rt | M + 1 |
|---|---|---|---|---|---|
| 118 | 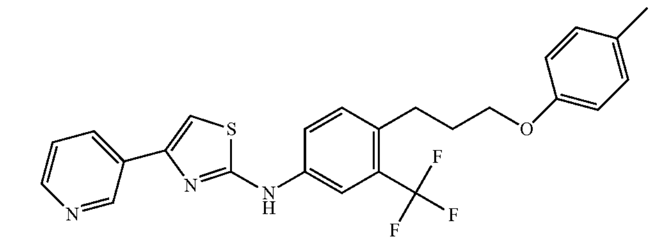 | 4-(pyridin-3-yl)-N-(4-(3-(p-tolyloxy)propyl)-3-(trifluoromethyl)phenyl)thiazol-2-amine | +++ | 1.78 | 470 |
| 119 | 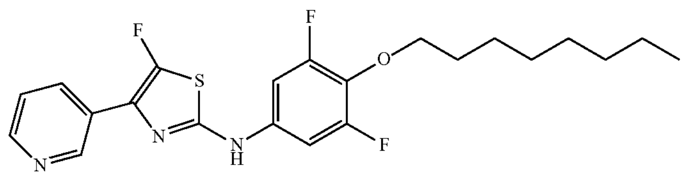 | N-(3,5-difluoro-4-(octyloxy)phenyl)-5-fluoro-4-(pyridin-3-yl)thiazol-2-amine | +++ | 1.98 | 436 |
| 120 | 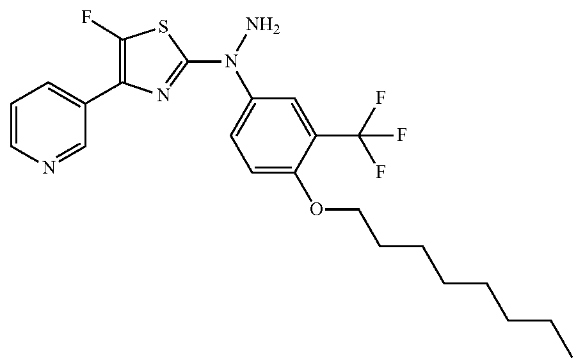 | 5-fluoro-2-(1-(4-(octyloxy)-3-(trifluoromethyl)phenyl)hydrazinyl)-4-(pyridin-3-yl)thiazole | +++ | 2.09 | 482 |

TABLE 1-continued

TABLE OF COMPOUNDS

| Cmp # | Structure | Name | Activity | rt | M + 1 |
|---|---|---|---|---|---|
| 121 | 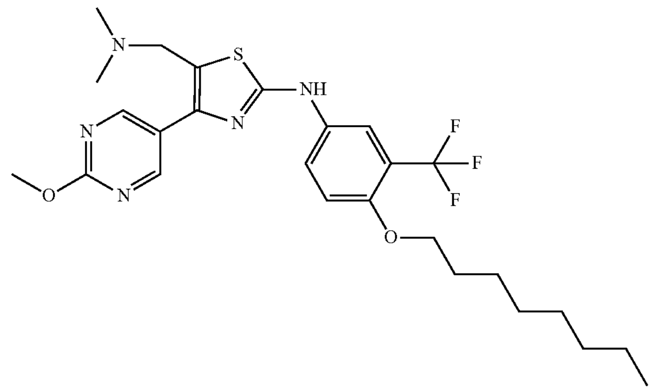 | 5-((dimethylamino)methyl)-4-(2-methoxypyrimidin-5-yl)-N-(4-(octyloxy)-3-(trifluoromethyl)phenyl)thiazol-2-amine | ++ | | |
| 122 | 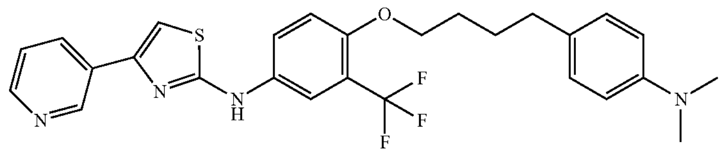 | N-(4-(4-(dimethylamino)phenyl)butoxy)-3-(trifluoromethyl)phenyl)-4-(pyridin-3-yl)thiazol-2-amine | +++ | 0.55 | 514 |
| 123 | 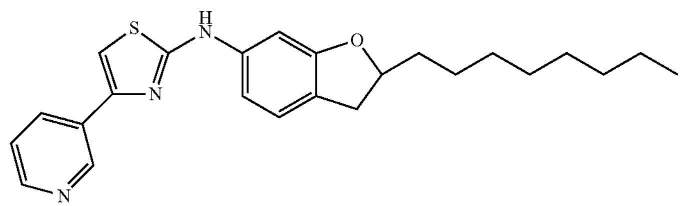 | N-(2-octyl-2,3-dihydrobenzofuran-6-yl)-4-(pyridin-3-yl)thiazol-2-amine | +++ | 1.96 | 408 |
| 124 | 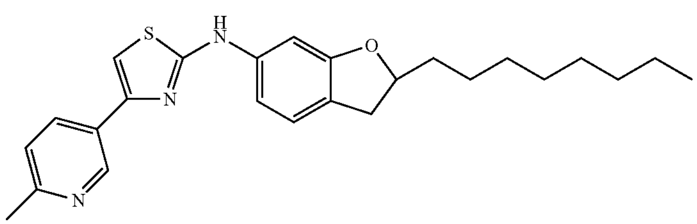 | 4-(6-methylpyridin-3-yl)-N-(2-octyl-2,3-dihydrobenzofuran-6-yl)thiazol-2-amine | +++ | 1.99 | 422 |

TABLE 1-continued

TABLE OF COMPOUNDS

| Cmp # | Structure | Name | Activity | rt | M + 1 |
|---|---|---|---|---|---|
| 125 | 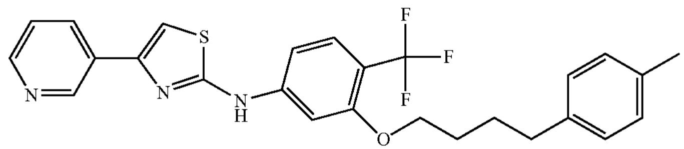 | 4-(pyridin-3-yl)-N-(3-(4-(p-tolyloxy)-4-(trifluoromethyl)phenyl)thiazol-2-amine | +++ | 1.79 | 484 |
| 126 | 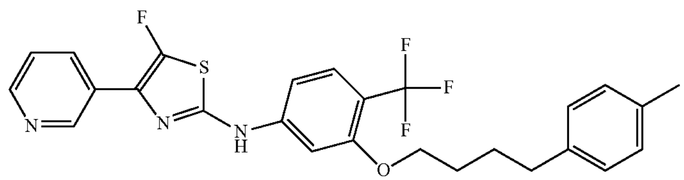 | 5-fluoro-4-pyridin-3-yl)-N-(3-(4-(p-tolyloxy)-4-trifluoromethyl)phenyl)thiazol-2-amine | +++ | 1.95 | 502 |
| 127 | 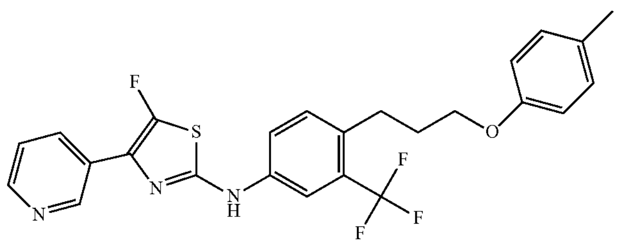 | 5-fluoro-4-(pyridin-3-yl)-N-(4-(3-(p-tolyloxy)propyl)-3-(trifluoromethyl)phenyl)thiazol-2-amine | +++ | 1.83 | 488 |
| 128 | 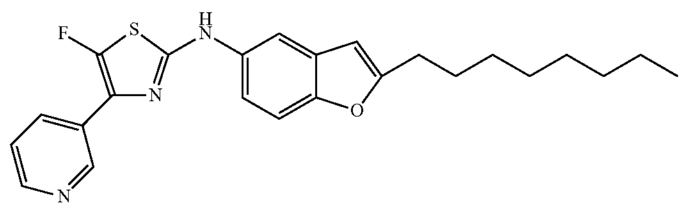 | 5-fluoro-N-(2-octylbenzofuran-5-yl)-4-(pyridin-3-yl)thiazol-2-amine | +++ | 2.15 | 424 |
| 129 | 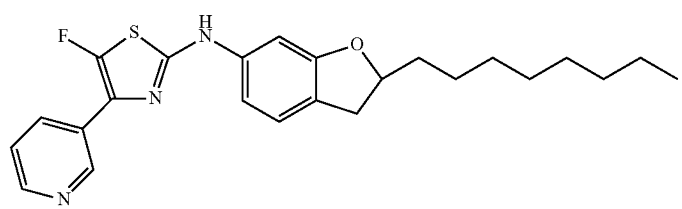 | 5-fluoro-N-(2-octyl-2,3-dihydrobenzofuran-6-yl)-4-(pyridin-3-yl)thiazol-2-amine | +++ | 2.08 | 426 |

TABLE 1-continued

TABLE OF COMPOUNDS

| Cmp # | Structure | Name | Activity | rt | M + 1 |
|---|---|---|---|---|---|
| 130 | 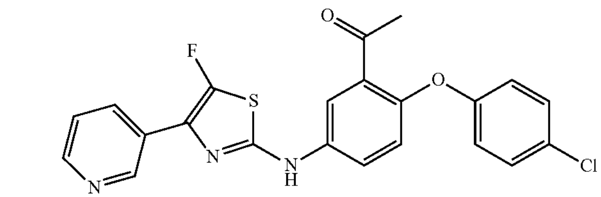 | 1-(2-(4-chlorophenoxy)-5-(5-fluoro-4-(pyridin-3-yl)thiazol-2-ylamino)phenyl)ethanone | +++ | 1.54 | 440 |
| 131 | 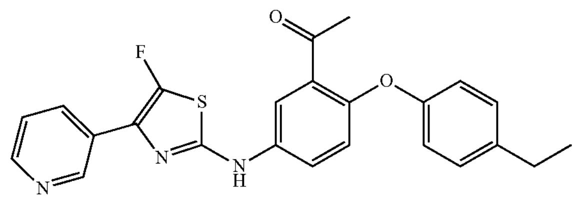 | 1-(2-(4-ethylphenoxy)-5-(5-fluoro-4-(pyridin-3-yl)thiazol-2-ylamino)phenyl)ethanone | +++ | 1.64 | 434 |
| 132 | 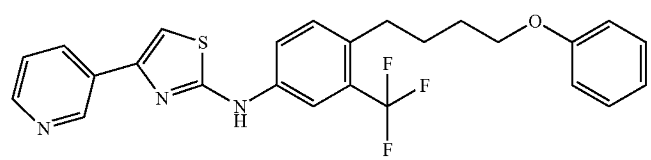 | N-(4-(4-phenoxybutyl)-3-trifluoromethyl)phenyl)-4-(pyridin-3-yl)thiazol-2-amine | +++ | 1.81 | 470 |
| 133 | 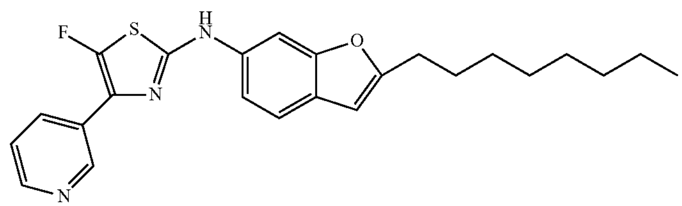 | 5-fluoro-N-(2-octylbenzofuran-6-yl)-4-(pyridin-3-yl)thiazol-2-amine | +++ | 2.14 | 424 |

TABLE 1-continued

TABLE OF COMPOUNDS

| Cmp # | Structure | Name | Activity | rt | M + 1 |
|---|---|---|---|---|---|
| 134 | 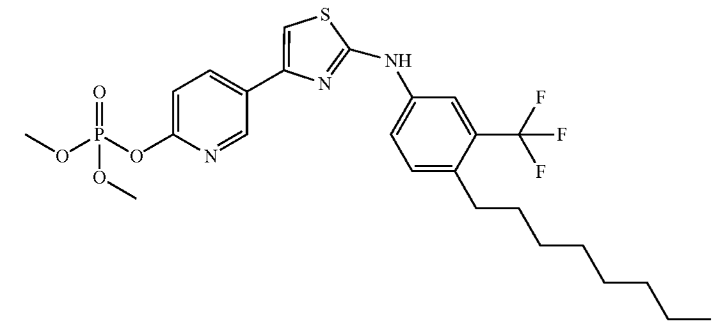 | dimethyl 5-(2-(4-octyl-3-(trifluoromethyl)phenylamino)thiazol-4-yl)pyridin-2-yl phosphate | +++ | 3.27 | 558 |
| 135 | 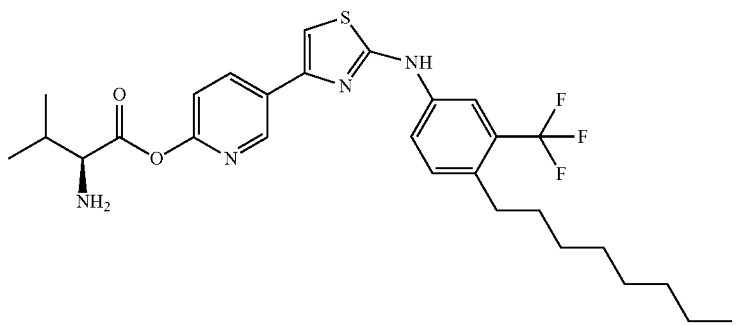 | (S)-5-(2-(4-octyl-3-(trifluoromethyl)phenylamino)thiazol-4-yl)pyridin-2-yl 2-amino-3-methylbutanoate | ++ | 2.54 | 663 |
| 136 | 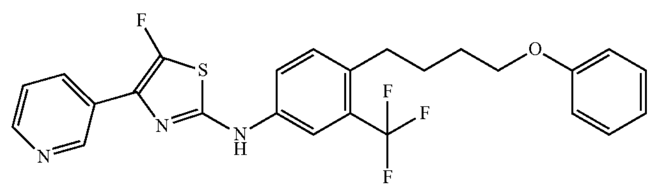 | 5-fluoro-N-(4-(4-phenoxybutyl)-3-(trifluoromethyl)phenyl)-4-(pyridin-3-yl)thiazol-2-amine | +++ | 1.87 | 488 |
| 137 | 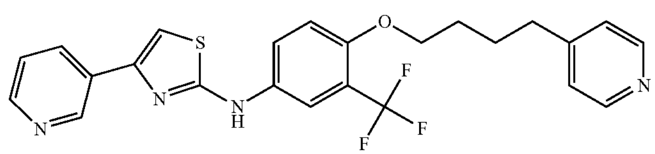 | 4-(pyridin-3-yl)-N-(4-(4-(pyridin-4-yl)butoxy)-3-(trifluoromethyl)phenyl)thiazol-2-amine | +++ | 0.70 | 471 |

TABLE 1-continued

TABLE OF COMPOUNDS

| Cmp # | Structure | Name | Activity | rt | M + 1 |
|---|---|---|---|---|---|
| 138 | 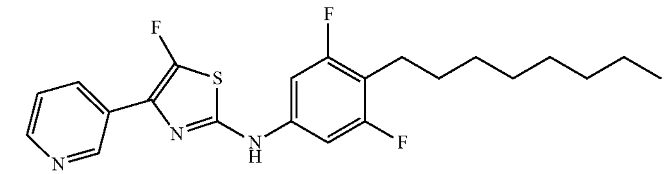 | N-(3,5-difluoro-4-octylphenyl)-5-fluoro-4-(pyridin-3-yl)thiazol-2-amine | +++ | 2.09 | 420 |
| 139 | 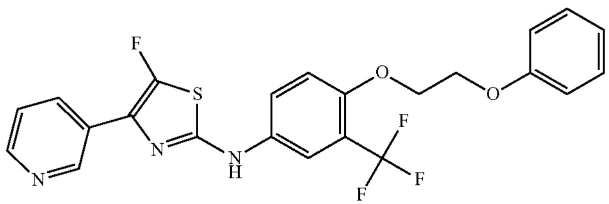 | 5-fluoro-N-(4-(2-phenoxyethoxy)-3-(trifluoromethyl)phenyl)-4-(pyridin-3-yl)thiazol-2-amine | +++ | 1.55 | 476 |
| 140 | 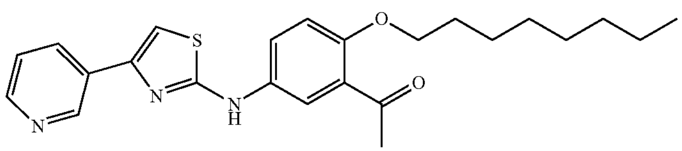 | 1-(2-(octyloxy)-5-(4-(pyridin-3-yl)thiazol-2-ylamino)phenyl)ethanone | +++ | 1.90 | 424 |
| 141 | 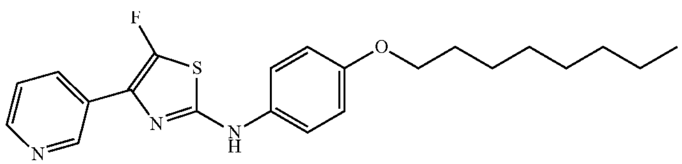 | 5-fluoro-N-(4-(octyloxy)phenyl)-4-(pyridin-3-yl)thiazol-2-amine | +++ | 1.93 | 400 |
| 142 | 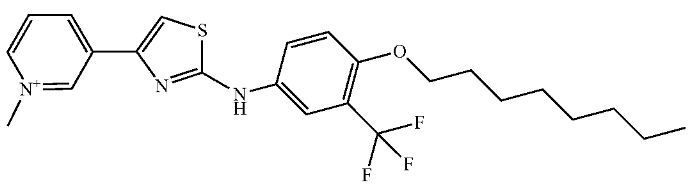 | 1-methyl-3-(2-(4-(octyloxy)-3-(trifluoromethyl)phenylamino)thiazol-4-yl)pyridinium | ++ | 1.92 | 464 |

TABLE 1-continued

TABLE OF COMPOUNDS

| Cmp # | Structure | Name | Activity | rt | M + 1 |
|---|---|---|---|---|---|
| 143 | 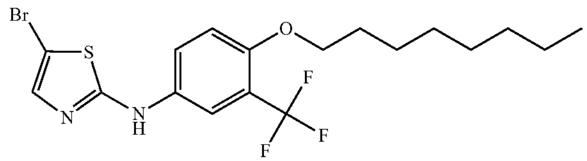 | 5-bromo-N-(4-(octyloxy)-3-(trifluoromethyl)phenyl)thiazol-2-amine | +++ | 3.50 | 453 |
| 144 | 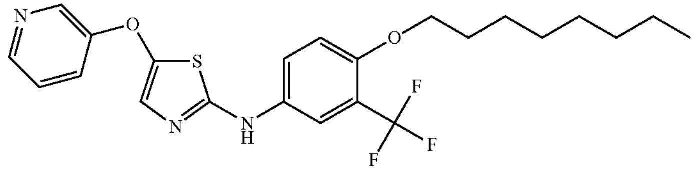 | N-(4-(octyloxy)-3-(trifluoromethyl)phenyl)-5-(pyridin-3-yloxy)thiazol-2-amine | +++ | 2.30 | 466 |
| 145 | 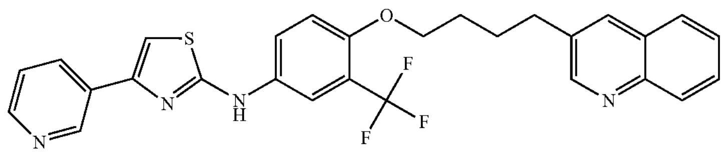 | 4-(pyridin-3-yl)-N-(4-(4-(quinolin-3-yl)butoxy)-3-(trifluoromethyl)phenyl)thiazol-2-amine | +++ | 1.55 | 521 |
| 146 | 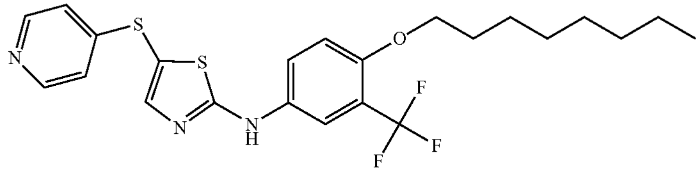 | N-(4-(octyloxy)-3-(trifluoromethyl)phenyl)-5-(pyridin-4-ylthio)thiazol-2-amine | ++ | 2.14 | 482 |
| 147 | 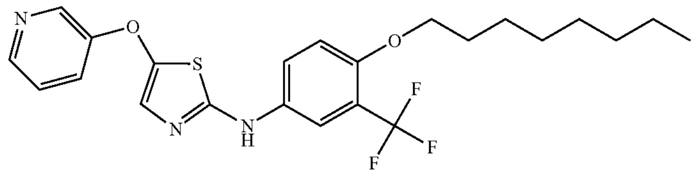 | N-(4-(octyloxy)-3-(trifluoromethyl)phenyl)-5-(pyridin-3-yloxy)thiazol-2-amine | +++ | 2.05 | 466 |

TABLE 1-continued

TABLE OF COMPOUNDS

| Cmp # | Structure | Name | Activity | rt | M + 1 |
|---|---|---|---|---|---|
| 148 | 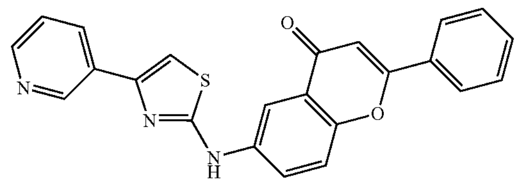 | 2-phenyl-6-(4-(pyridin-3-yl)thiazol-2-ylamino)-4H-chromen-4-one | + | 1.14 | 398 |
| 149 | 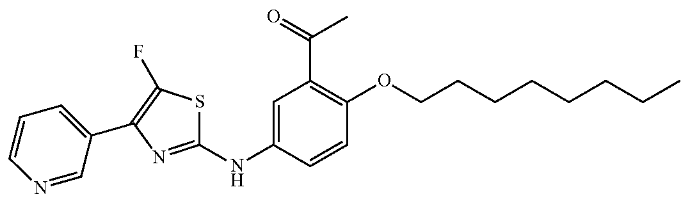 | 1-(5-fluoro-4-(pyridin-3-yl)thiazol-2-ylamino)-2-(octyloxy)phenyl)ethanone | +++ | 1.26 | 442 |
| 150 | 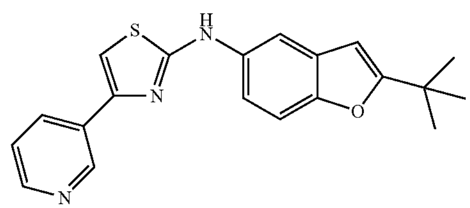 | N-(2-tert-butylbenzofuran-5-yl)-4-(pyridin-3-yl)thiazol-2-amine | +++ | 1.35 | 350 |
| 151 | 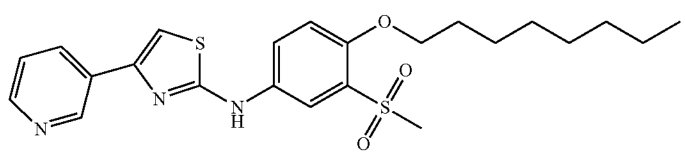 | N-(3-(methylsulfonyl)-4-(octyloxy)phenyl)-4-(pyridin-3-yl)thiazol-2-amine | +++ | 1.62 | 460 |
| 152 | 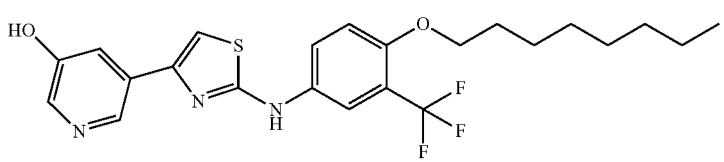 | 5-(2-(4-(octyloxy)-3-(trifluoromethyl)phenylamino)thiazol-4-yl)pyridin-3-ol | +++ | 2.00 | 466 |

TABLE 1-continued

TABLE OF COMPOUNDS

| Cmp # | Structure | Name | Activity | rt | M + 1 |
|---|---|---|---|---|---|
| 153 | 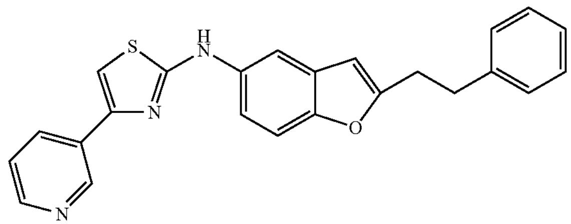 | N-(2-phenethylbenzofuran-5-yl)-4-(pyridin-3-yl)thiazol-2-amine | +++ | 1.32 | 398 |
| 154 | 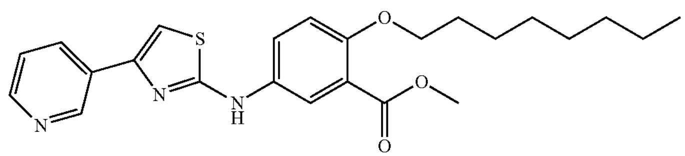 | methyl 2-(octyloxy)-5-(4-(pyridin-3-yl)thiazol-2-ylamino)benzoate | +++ | 1.83 | 440 |
| 155 | 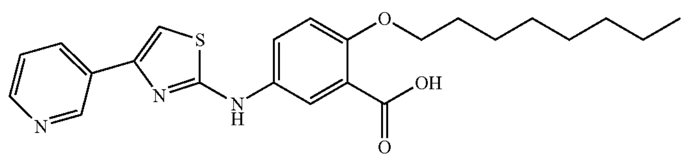 | 2-(octyloxy)-5-(4-(pyridin-3-yl)thiazol-2-ylamino)benzoic acid | + | 1.45 | 426 |
| 156 | 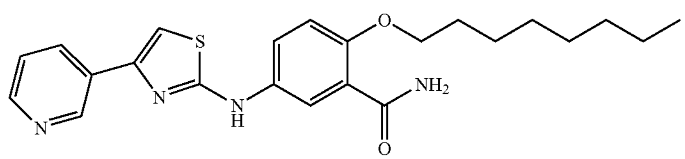 | 2-(octyloxy)-5-(4-(pyridin-3-yl)thiazol-2-ylamino)benzamide | +++ | 1.37 | 425 |
| 157 | 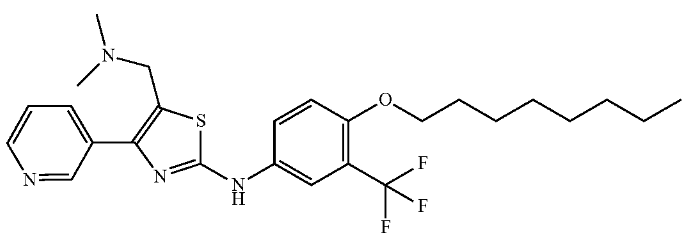 | 5-((dimethylamino)methyl)-N-(4-(octyloxy)-3-(trifluoromethyl)phenyl)-4-(pyridin-3-yl)thiazol-2-amine | ++ | 1.35 | 462 |

TABLE 1-continued

TABLE OF COMPOUNDS

| Cmp # | Structure | Name | Activity | rt | M + 1 |
|---|---|---|---|---|---|
| 158 | 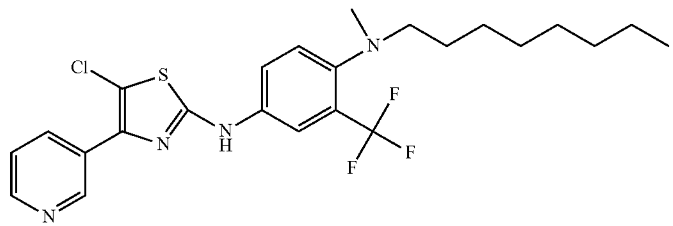 | N4-(5-chloro-4-(pyridin-3-yl)thiazol-2-yl)-N1-methyl-N1-octyl-2-(trifluoromethyl)benzene-1,4-diamine | +++ | 2.08 | 497 |
| 159 | 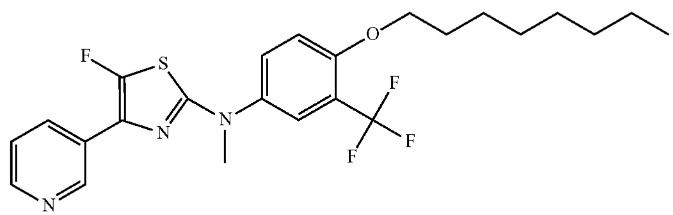 | 5-fluoro-N-methyl-N-(4-(octyloxy)-3-(trifluoromethyl)phenyl)-4-(pyridin-3-yl)thiazol-2-amine | +++ | 1.93 | 481 |
| 160 | 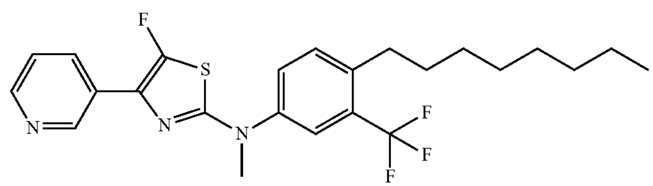 | 5-fluoro-N-methyl-N-(4-octyl-3-(trifluoromethyl)phenyl)-4-(pyridin-3-yl)thiazol-2-amine | ++ | 2.51 | 465 |
| 161 | 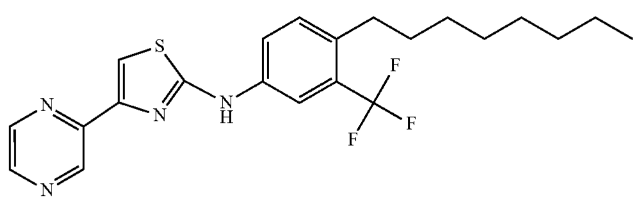 | N-(4-octyl-3-(trifluoromethyl)phenyl)-4-(pyrazin-2-yl)thiazol-2-amine | +++ | 3.94 | 435 |

TABLE 1-continued

TABLE OF COMPOUNDS

| Cmp # | Structure | Name | Activity | rt | M + 1 |
|---|---|---|---|---|---|
| 162 | 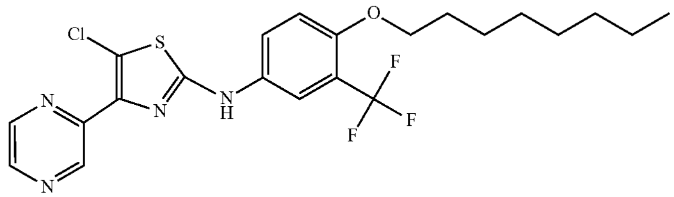 | 5-chloro-N-(4-(octyloxy)-3-(trifluoromethyl)phenyl)-4-(pyrazin-2-yl)thiazol-2-amine | +++ | 3.6 | 485 |
| 163 | 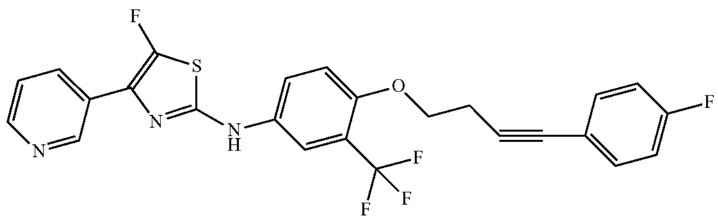 | 5-fluoro-N-(4-(4-fluorophenyl)but-3-ynyloxy)-3-(trifluoromethyl)phenyl)-4-(pyridin-3-yl)thiazol-2-amine | +++ | 1.80 | 502 |
| 164 | 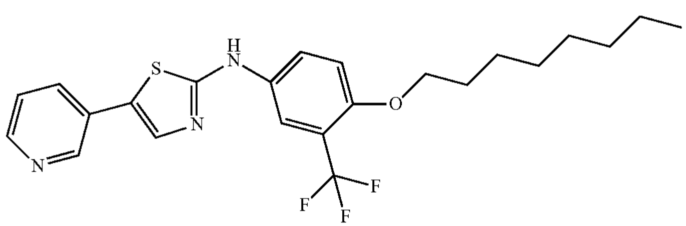 | N-(4-(octyloxy)-3-(trifluoromethyl)phenyl)-5-(pyridin-3-yl)thiazol-2-amine | +++ | 2.02 | 450 |
| 165 | 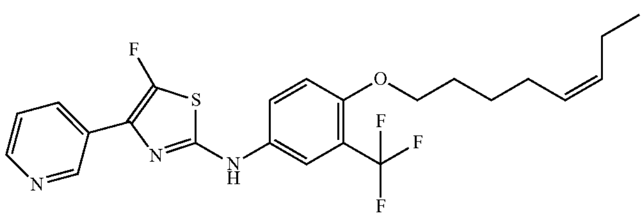 | (Z)-5-fluoro-N-(4-(oct-5-enyloxy)-3-(trifluoromethyl)phenyl)-4-(pyridin-3-yl)thiazol-2-amine | +++ | 2.12 | 466 |

TABLE I-continued

TABLE OF COMPOUNDS

| Cmp # | Structure | Name | Activity | rt | M + 1 |
|---|---|---|---|---|---|
| 166 | 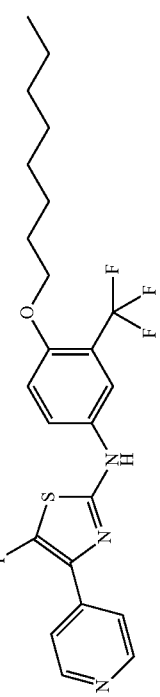 | 5-fluoro-N-(4-(octyloxy)-3-(trifluoromethyl)phenyl)-4-(pyridin-4-yl)thiazol-2-amine | +++ | 2.35 | 468 |
| 167 | 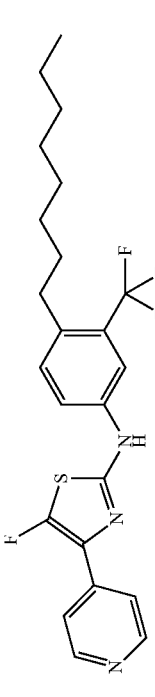 | 5-fluoro-N-(4-octyl-3-(trifluoromethyl)phenyl)-4-(pyridin-4-yl)thiazol-2-amine | +++ | 2.44 | 452 |
| 168 | 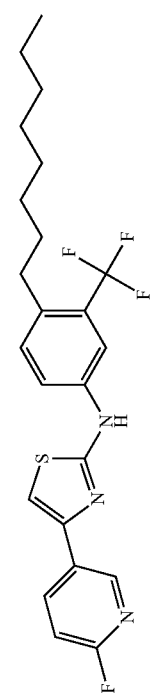 | 4-(6-fluoropyridin-3-yl)-N-(4-octyl-3-(trifluoromethyl)phenyl)thiazol-2-amine | +++ | 4.13 | 452 |
| 169 | 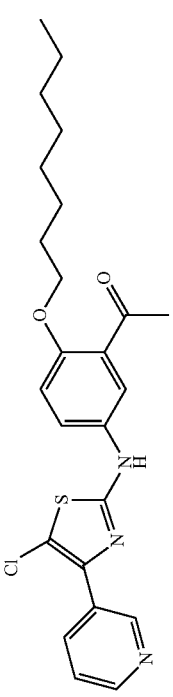 | 1-(5-chloro-4-(pyridin-3-yl)thiazol-2-ylamino)-2-(octyloxy)phenyl)ethanone | +++ | 2.05 | 458 |
| 170 | 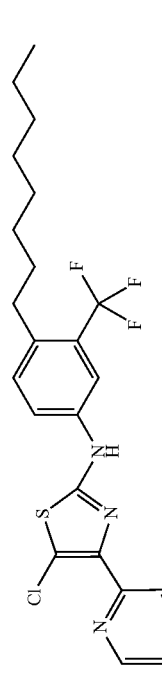 | 5-chloro-N-(4-octyl-3-(trifluoromethyl)phenyl)-4-(pyrazin-2-yl)thiazol-2-amine | +++ | 4.0 | 469 |

TABLE I-continued

TABLE OF COMPOUNDS

| Cmp # | Structure | Name | Activity | rt | M + 1 |
|---|---|---|---|---|---|
| 171 | 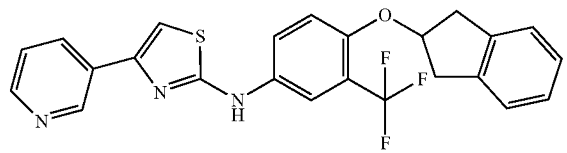 | N-(4-(2,3-dihydro-1H-inden-2-yloxy)-3-(trifluoromethyl)phenyl)-4-(pyridin-3-yl)thiazol-2-amine | +++ | 1.64 | 454 |
| 172 | 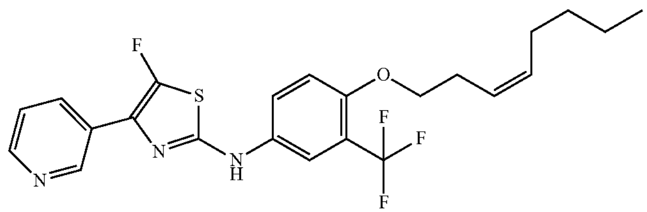 | (Z)-5-fluoro-N-(4-(oct-3-enyloxy)-3-(trifluoromethyl)phenyl)-4-(pyridin-3-yl)thiazol-2-amine | +++ | 1.77 | 466 |
| 173 | 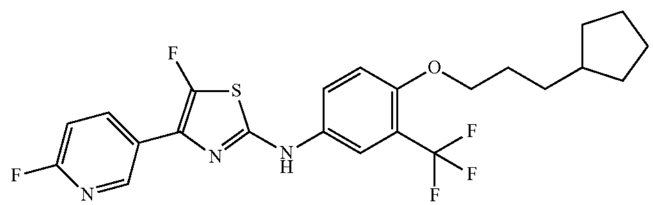 | N-(4-(3-cyclopentylpropoxy)-3-(trifluoromethyl)phenyl)-5-fluoro-4-(6-fluoropyridin-3-yl)thiazol-2-amine | +++ | 3.48 | 485 |
| 174 | 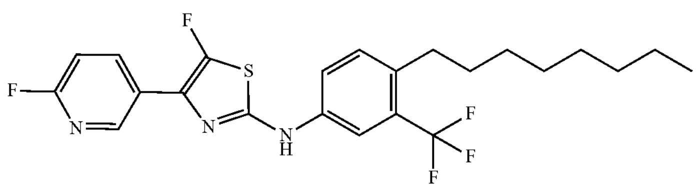 | 5-fluoro-4-(6-fluoropyridin-3-yl)-N-(4-octyl-3-(trifluoromethyl)phenyl)thiazol-2-amine | +++ | 4.28 | 471 |
| 175 | 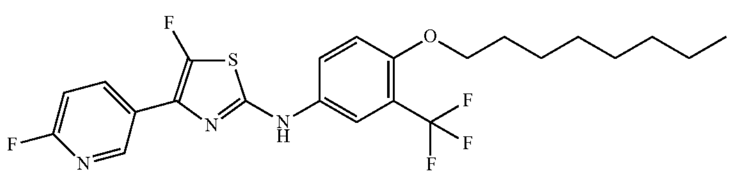 | 5-fluoro-4-(6-fluoropyridin-3-yl)-N-(4-(octyloxy)-3-(trifluoromethyl)phenyl)thiazol-2-amine | +++ | 3.77 | 487 |

TABLE 1-continued

TABLE OF COMPOUNDS

| Cmp # | Structure | Name | Activity | rt | M + 1 |
|---|---|---|---|---|---|
| 176 | 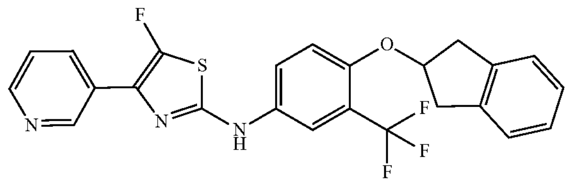 | N-(4-(2,3-dihydro-1H-inden-2-yloxy)-3-(trifluoromethyl)phenyl)-5-fluoro-4-(pyridin-3-yl)thiazol-2-amine | +++ | 1.6 | 472 |
| 177 | 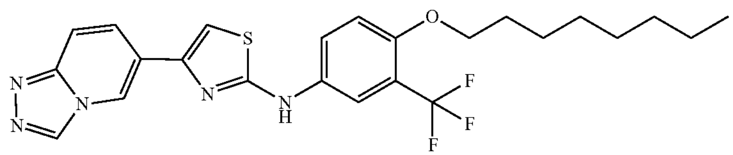 | 4-([1,2,4]triazolo[4,3-a]pyridin-6-yl)-N-(4-(octyloxy)-3-(trifluoromethyl)phenyl)thiazol-2-amine | +++ | 2.01 | 489 |
| 178 | 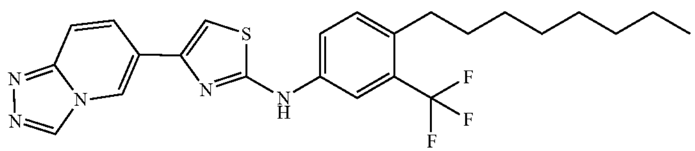 | 4-([1,2,4]triazolo[4,3-a]pyridin-6-yl)-N-(4-octyl-3-(trifluoromethyl)phenyl)thiazol-2-amine | +++ | 2.29 | 473 |
| 179 | 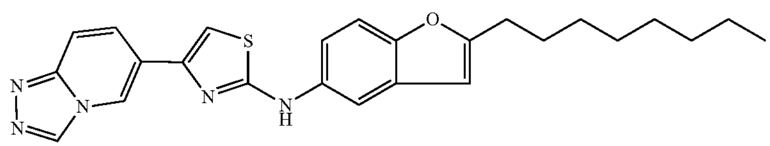 | 4-([1,2,4]triazolo[4,3-a]pyridin-6-yl)-N-(2-octylbenzofuran-5-yl)thiazol-2-amine | +++ | 2.16 | 445 |
| 180 | 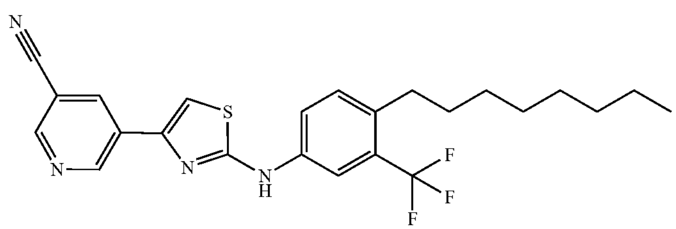 | 5-(2-(4-octyl-3-(trifluoromethyl)phenylamino)thiazol-4-yl)nicotinonitrile | +++ | 3.57 | 458 |

TABLE I-continued

TABLE OF COMPOUNDS

| Cmp # | Structure | Name | Activity | rt | M + 1 |
|---|---|---|---|---|---|
| 181 | 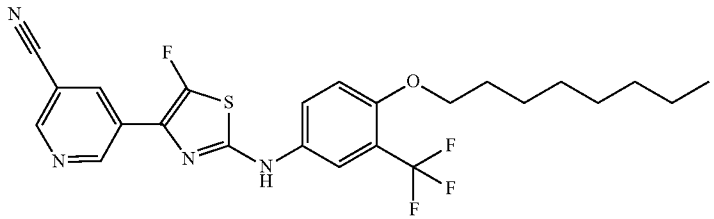 | 5-(5-fluoro-2-(4-(octyloxy)-3-(trifluoromethyl)phenylamino)thiazol-4-yl)nicotinonitrile | +++ | 3.40 | 492 |
| 182 | 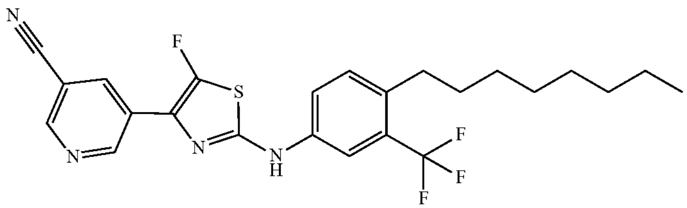 | 5-(5-fluoro-2-(4-octyl-3-(trifluoromethyl)phenylamino)thiazol-4-yl)nicotinonitrile | +++ | 3.94 | 476 |
| 183 | 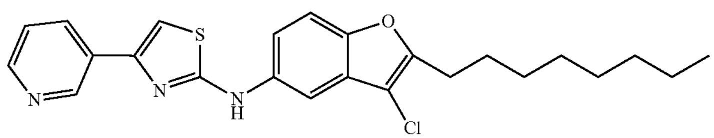 | N-(3-chloro-2-octylbenzofuran-5-yl)-4-(pyridin-3-yl)thiazol-2-amine | +++ | 2.23 | 440 |
| 184 | 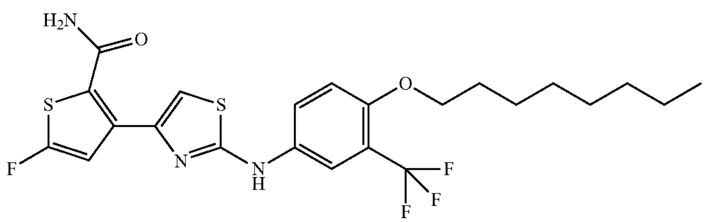 | 5-fluoro-3-(2-(4-(octyloxy)-3-(trifluoromethyl)phenylamino)thiazol-4-yl)thiophene-2-carboxamide | +++ | 2.47 | 516 |

TABLE 1-continued

TABLE OF COMPOUNDS

| Cmp # | Structure | Name | Activity | rt | M + 1 |
|---|---|---|---|---|---|
| 185 | 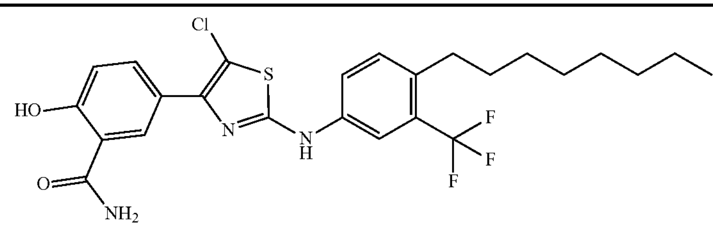 | 5-(5-chloro-2-(4-octyl-3-(trifluoromethyl)phenylamino)thiazol-4-yl)-2-hydroxybenzamide | +++ | 3.83 | 527 |
| 186 | 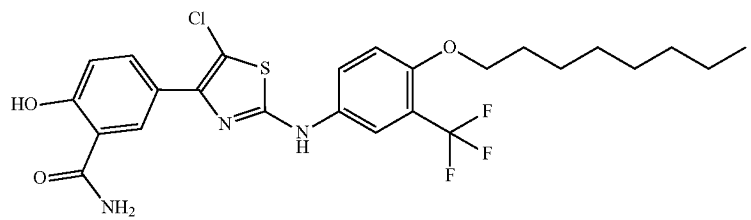 | 5-(5-chloro-2-(4-(octyloxy)-3-(trifluoromethyl)phenylamino)thiazol-4-yl)-2-hydroxybenzamide | +++ | 3.45 | 543 |
| 187 | 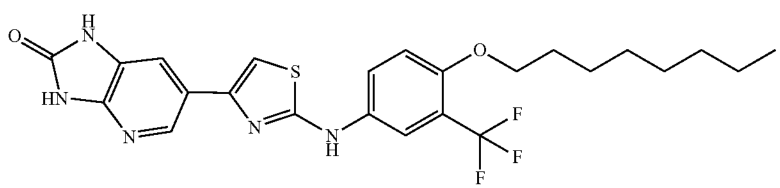 | 6-(2-(4-(octyloxy)-3-(trifluoromethyl)phenylamino)thiazol-4-yl)-1H-imidazo[4,5-b]pyridin-2(3H)-one | +++ | 2.41 | 506 |
| 188 | 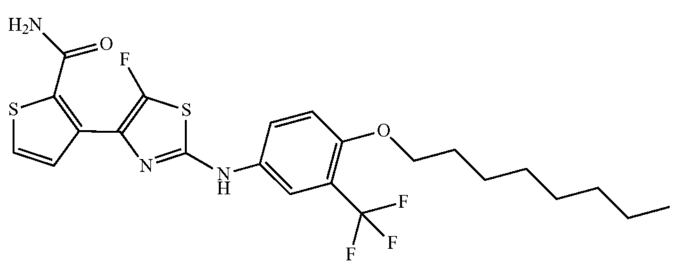 | 3-(5-fluoro-2-(4-(octyloxy)-3-(trifluoromethyl)phenylamino)thiazol-4-yl)thiophene-2-carboxamide | +++ | 3.09 | 516 |

TABLE 1-continued

TABLE OF COMPOUNDS

| Cmp # | Structure | Name | Activity | rt | M + 1 |
|---|---|---|---|---|---|
| 189 | 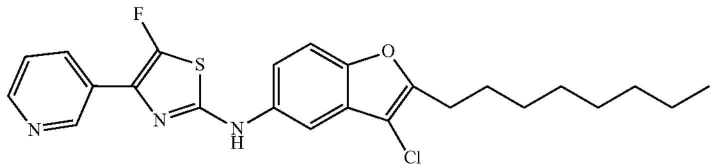 | N-(3-chloro-2-octylbenzofuran-5-yl)-5-fluoro-4-(pyridin-3-yl)thiazol-2-amine | +++ | 2.50 | 458 |
| 190 | 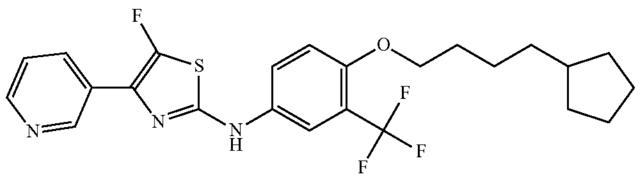 | N-(4-(4-cyclopentylbutoxy)-3-(trifluoromethyl)phenyl)-5-fluoro-4-(pyridin-3-yl)thiazol-2-amine | +++ | 2.19 | 480 |
| 191 | 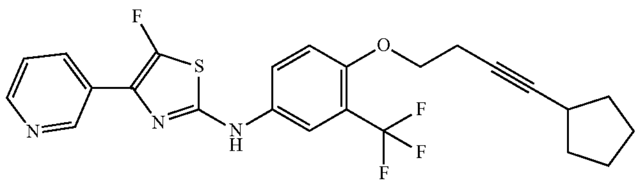 | N-(4-(4-cyclopentylbut-3-ynyloxy)-3-(trifluoromethyl)phenyl)-5-fluoro-4-(pyridin-3-yl)thiazol-2-amine | +++ | 1.88 | 476 |
| 192 | 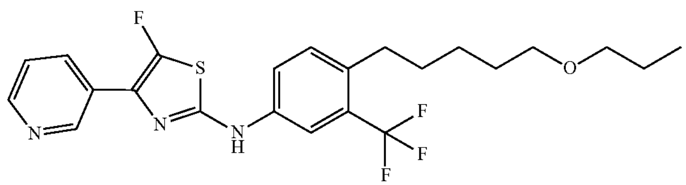 | 5-fluoro-N-(4-(5-propoxypentyl)-3-(trifluoromethyl)phenyl)-4-(pyridin-3-yl)thiazol-2-amine | +++ | 2.52 | 468 |
| 193 | 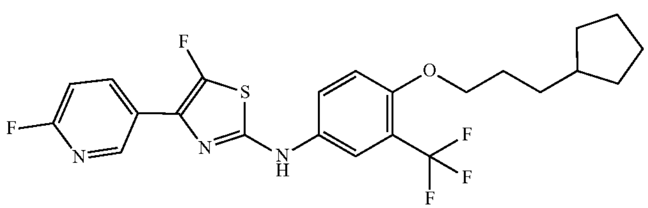 | N-(4-(3-cyclopentylpropoxy)-3-(trifluoromethyl)phenyl)-5-fluoro-4-(6-fluoropyridin-3-yl)thiazol-2-amine | +++ | | |

TABLE I-continued

TABLE OF COMPOUNDS

| Cmp # | Structure | Name | Activity | rt | M + 1 |
|---|---|---|---|---|---|
| 194 | 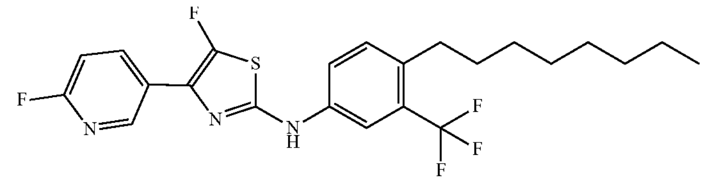 | 5-fluoro-4-(6-fluoropyridin-3-yl)-N-(4-octyl-3-(trifluoromethyl)phenyl)thiazol-2-amine | +++ | | |
| 195 | 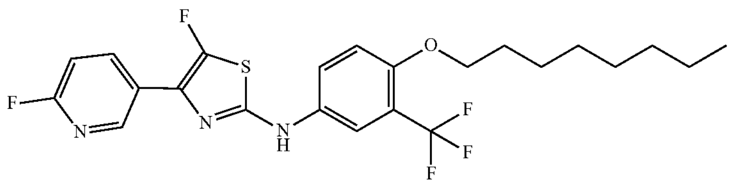 | 5-fluoro-4-(6-fluoropyridin-3-yl)-N-(4-(octyloxy)-3-(trifluoromethyl)phenyl)thiazol-2-amine | +++ | | |
| 196 | 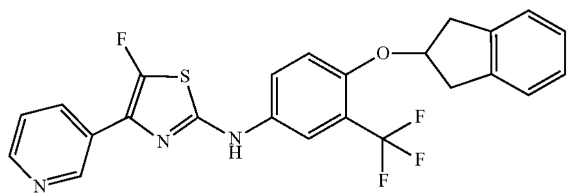 | N-(4-(2,3-dihydro-1H-inden-2-yloxy)-3-(trifluoromethyl)phenyl)-5-fluoro-4-(pyridin-3-yl)thiazol-2-amine | +++ | | |
| 197 | 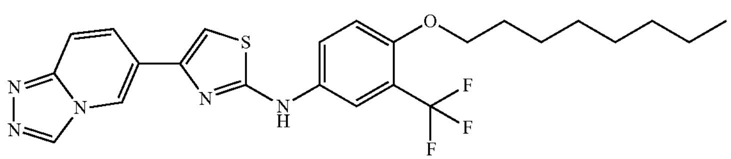 | 4-([1,2,4]triazolo[4,3-a]pyridin-6-yl)-N-(4-(octyloxy)-3-(trifluoromethyl)phenyl)thiazol-2-amine | +++ | | |
| 198 | 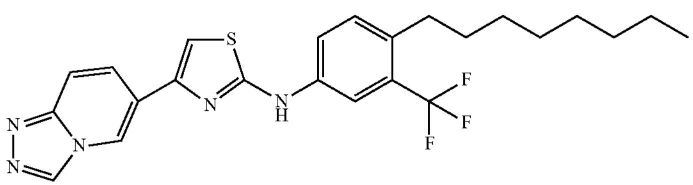 | 4-([1,2,4]triazolo[4,3-a]pyridin-6-yl)-N-(4-octyl-3-(trifluoromethyl)phenyl)thiazol-2-amine | +++ | | |

TABLE 1-continued

TABLE OF COMPOUNDS

| Cmp # | Structure | Name | Activity | rt | M + 1 |
|---|---|---|---|---|---|
| 199 | 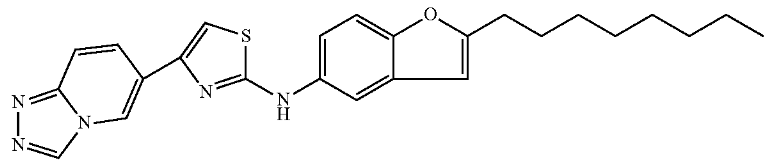 | 4-([1,2,4]triazolo[4,3-a]pyridin-6-yl)-N-(2-octylbenzofuran-5-yl)thiazol-2-amine | +++ | | |
| 200 | 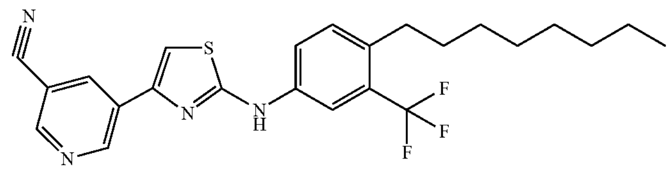 | 5-(2-(4-octyl-3-(trifluoromethyl)phenylamino)thiazol-4-yl)nicotinonitrile | +++ | | |
| 201 | 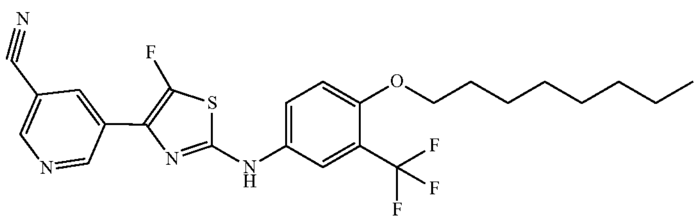 | 5-(5-fluoro-2-(4-(octyloxy)-3-(trifluoromethyl)phenylamino)thiazol-4-yl)nicotinonitrile | +++ | | |
| 202 | 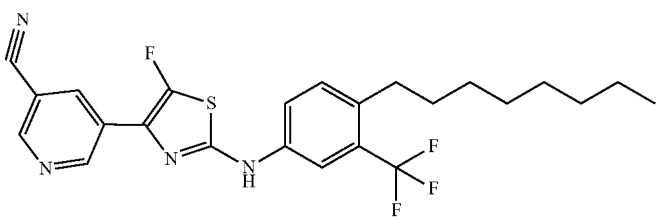 | 5-(5-fluoro-2-(4-octyl-3-(trifluoromethyl)phenylamino)thiazol-4-yl)nicotinonitrile | +++ | | |
| 203 | 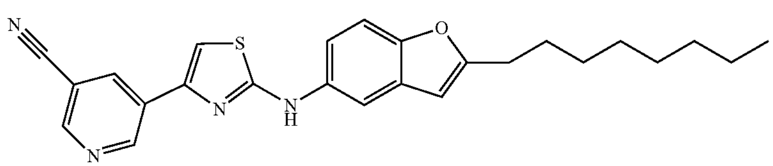 | 5-(2-(2-octylbenzofuran-5-ylamino)thiazol-4-yl)nicotinonitrile | +++ | | |

TABLE 1-continued

TABLE OF COMPOUNDS

| Cmp # | Structure | Name | Activity | rt | M + 1 |
|---|---|---|---|---|---|
| 204 | 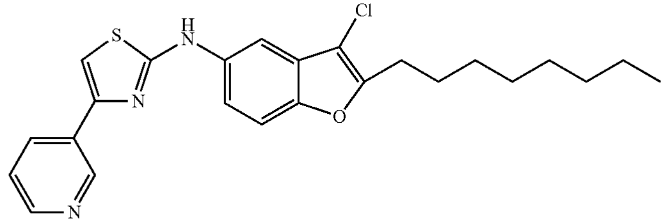 | N-(3-chloro-2-octylbenzofuran-5-yl)-4-(pyridin-3-yl)thiazol-2-amine | +++ | | |
| 205 | 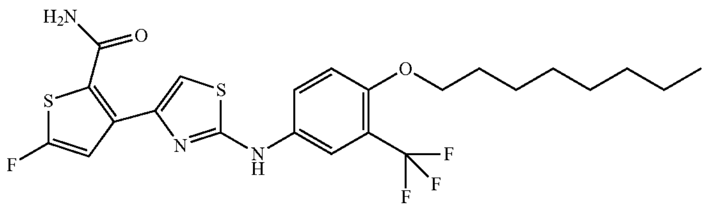 | 5-fluoro-3-(2-(4-(octyloxy)-3-(trifluoromethyl)phenylamino)thiazol-4-yl)thiophene-2-carboxamide | +++ | | |
| 206 | 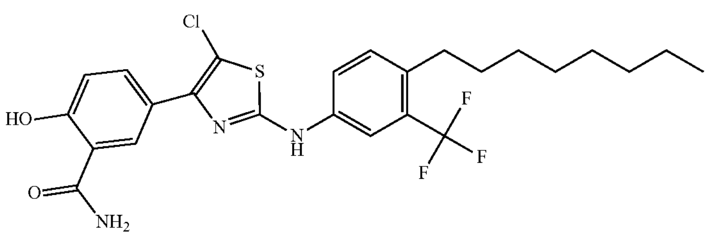 | 5-fluoro-3-(2-(4-(octyloxy)-3-(trifluoromethyl)phenylamino)thiazol-4-yl)thiophene-2-carboxamide | +++ | | |
| 207 | 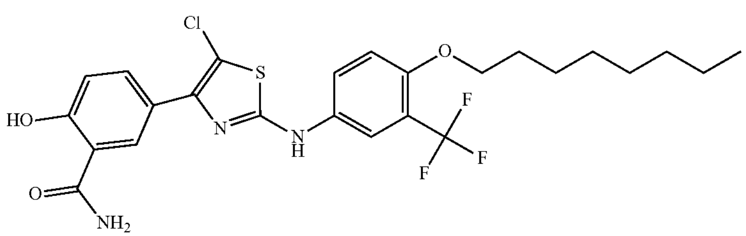 | 5-(5-chloro-2-(4-(octyloxy)-3-(trifluoromethyl)phenylamino)thiazol-4-yl)-2-hydroxybenzamide | +++ | | |

TABLE 1-continued

TABLE OF COMPOUNDS

| Cmp # | Structure | Name | Activity | rt | M + 1 |
|---|---|---|---|---|---|
| 208 | 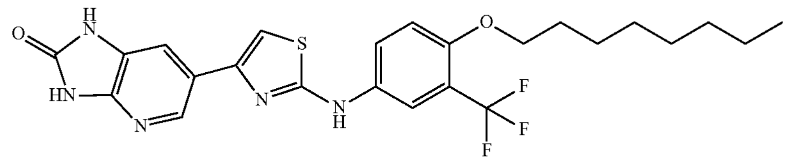 | 6-(2-(4-(octyloxy)-3-(trifluoromethyl)phenylamino)thiazol-4-yl)-1H-imidazo[4,5-b]pyridin-2(3H)-one | +++ | | |
| 209 | 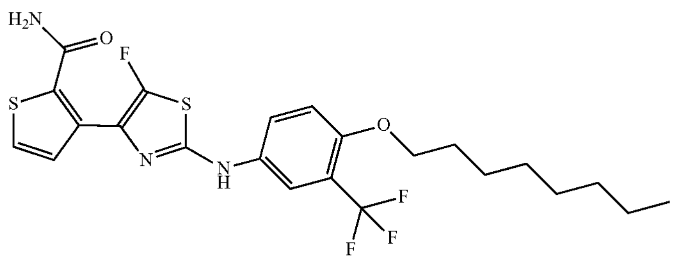 | 3-(5-fluoro-2-(4-(octyloxy)-3-(trifluoromethyl)phenylamino)thiazol-4-yl)thiophene-2-carboxamide | +++ | | |
| 210 | 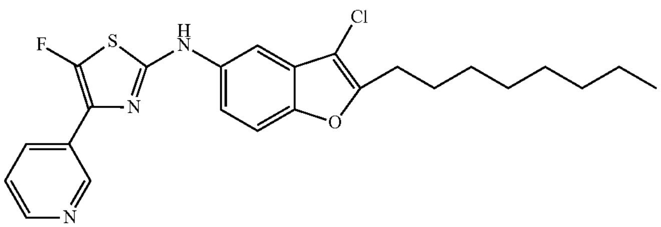 | N-(3-chloro-2-octylbenzofuran-5-yl)-5-fluoro-4-(pyridin-3-yl)thiazol-2-amine | +++ | | |
| 211 | 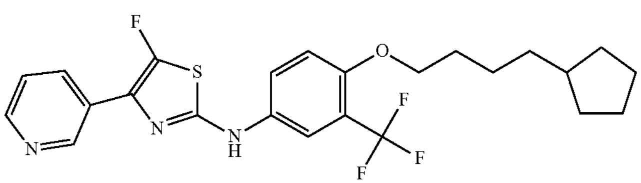 | N-(4-(4-cyclopentylbutoxy)-3-(trifluoromethyl)phenyl)-5-fluoro-4-(pyridin-3-yl)thiazol-2-amine | +++ | | |
| 212 | 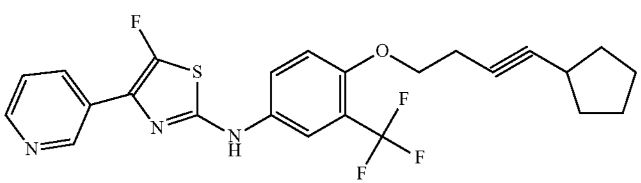 | N-(4-(4-cyclopentylbut-3-ynyloxy)-3-(trifluoromethyl)phenyl)-5-fluoro-4-(pyridin-3-yl)thiazol-2-amine | +++ | | |

TABLE 1-continued

TABLE OF COMPOUNDS

| Cmp # | Structure | Name | Activity | rt | M + 1 |
|---|---|---|---|---|---|
| 213 | 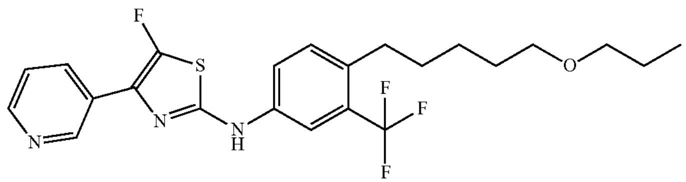 | 5-fluoro-N-(4-(5-propoxypentyl)-3-(trifluoromethyl)phenyl)-4-(pyridin-3-yl)thiazol-2-amine | +++ | | |
| 214 | 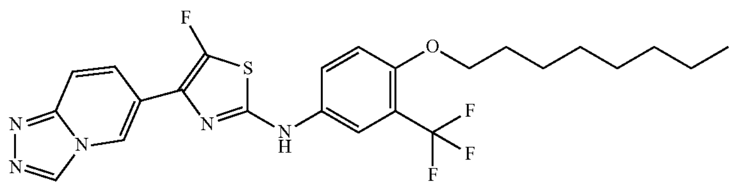 | 4-([1,2,4]triazolo[4,3-a]pyridin-6-yl)-5-fluoro-N-(4-(octyloxy)-3-(trifluoromethyl)phenyl)thiazol-2-amine | +++ | | |
| 215 | 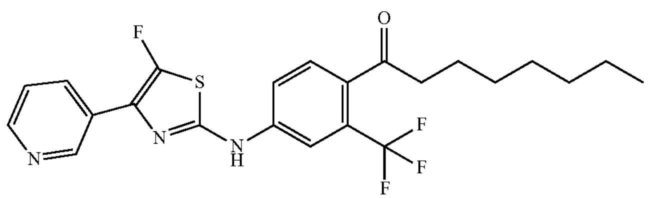 | 1-(4-(5-fluoro-4-(pyridin-3-yl)thiazol-2-ylamino)-2-(trifluoromethyl)phenyl)octan-1-one | +++ | | |
| 216 | 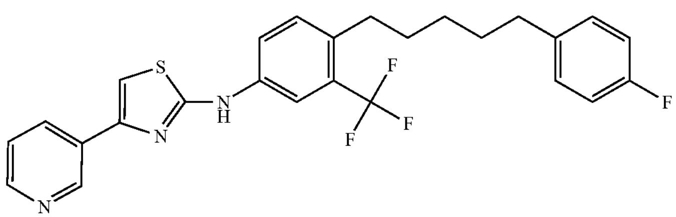 | N-(4-(5-(4-fluorophenyl)pentyl)-3-(trifluoromethyl)phenyl)-4-(pyridin-3-yl)thiazol-2-amine | +++ | | |

TABLE I-continued

TABLE OF COMPOUNDS

| Cmp # | Structure | Name | Activity | rt | M + 1 |
|---|---|---|---|---|---|
| 217 | 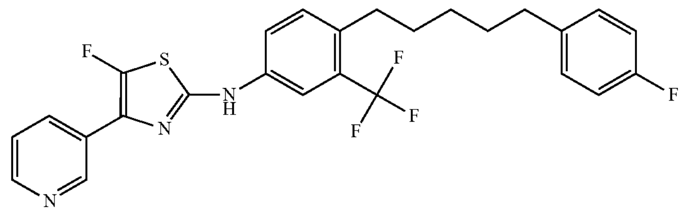 | 5-fluoro-N-(4-(5-(4-fluorophenyl)pentyl)-3-(trifluoromethyl)phenyl)-4-(pyridin-3-yl)thiazol-2-amine | +++ | | |
| 218 | 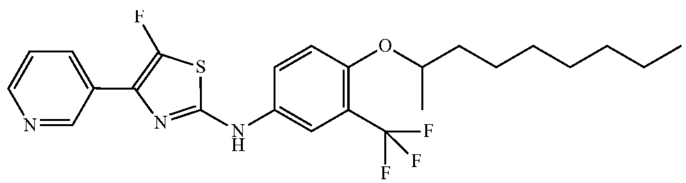 | 5-fluoro-N-(4-(nonan-2-yloxy)-3-(trifluoromethyl)phenyl)-4-(pyridin-3-yl)thiazol-2-amine | +++ | | |
| 219 | 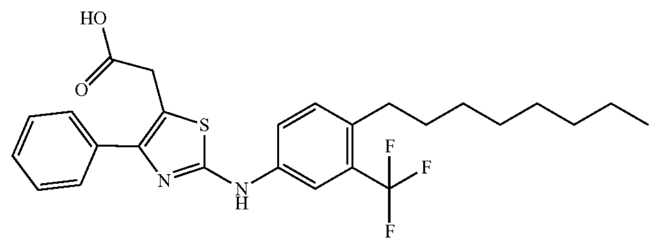 | 2-(2-(4-octyl-3-(trifluoromethyl)phenylamino)-4-phenylthiazol-5-yl)acetic acid | ++ | | |
| 220 | 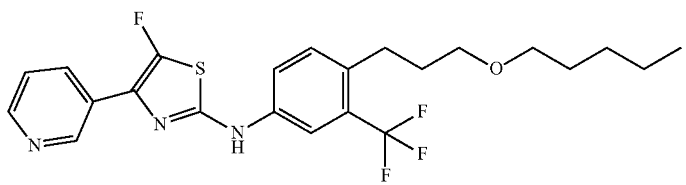 | 5-fluoro-N-(4-(3-(pentyloxy)propyl)-3-(trifluoromethyl)phenyl)-4-(pyridin-3-yl)thiazol-2-amine | +++ | | |
| 221 | 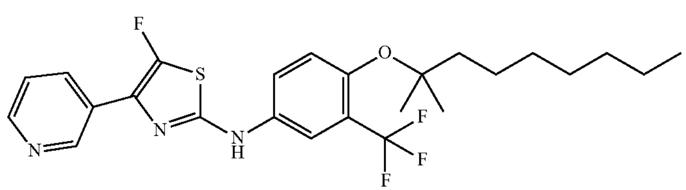 | 5-fluoro-N-(4-(2-methylnonan-2-yloxy)-3-(trifluoromethyl)phenyl)-4-(pyridin-3-yl)thiazol-2-amine | +++ | | |

TABLE 1-continued

TABLE OF COMPOUNDS

| Cmp # | Structure | Name | Activity | rt | M + 1 |
|---|---|---|---|---|---|
| 222 | 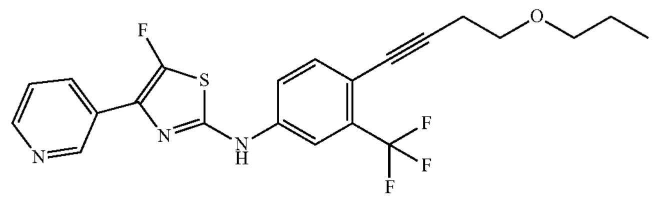 | 5-fluoro-N-(4-(4-propoxybut-1-ynyl)-3-(trifluoromethyl)phenyl)-4-(pyridin-3-yl)thiazol-2-amine | +++ | | |
| 223 | 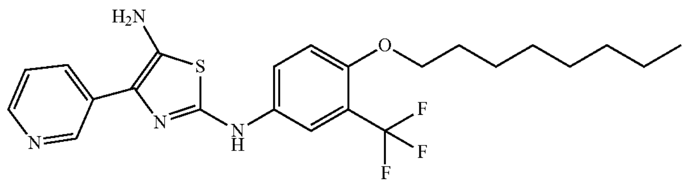 | N2-(4-(octyloxy)-3-(trifluoromethyl)phenyl)-4-(pyridin-3-yl)thiazole-2,5-diamine | | | |
| 224 | 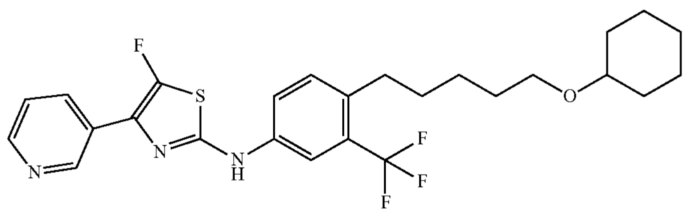 | N-(4-(5-(cyclohexyloxy)pentyl)-3-(trifluoromethyl)phenyl)-5-fluoro-4-(pyridin-3-yl)thiazol-2-amine | | | |
| 225 | 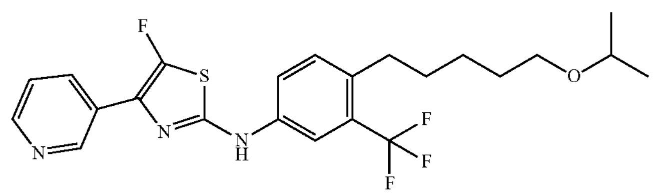 | 5-fluoro-N-(4-(5-isopropoxypentyl)-3-(trifluoromethyl)phenyl)-4-(pyridin-3-yl)thiazol-2-amine | | | |
| 226 | 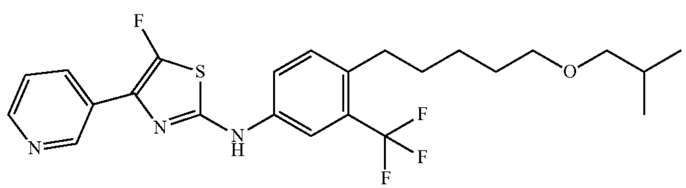 | 5-fluoro-N-(4-(5-isobutoxypentyl)-3-(trifluoromethyl)phenyl)-4-(pyridin-3-yl)thiazol-2-amine | | | |

TABLE 1-continued

TABLE OF COMPOUNDS

| Cmp # | Structure | Name | Activity | rt | M + 1 |
|---|---|---|---|---|---|
| 227 | 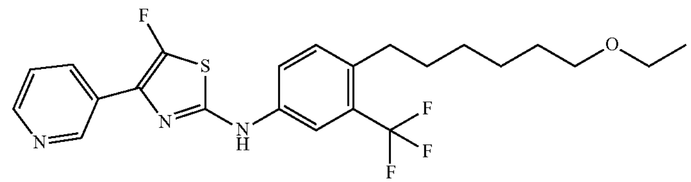 | N-(4-(6-ethoxyhexyl)-3-(trifluoromethyl)phenyl)-5-fluoro-4-(pyridin-3-yl)thiazol-2-amine | | | |
| 228 | 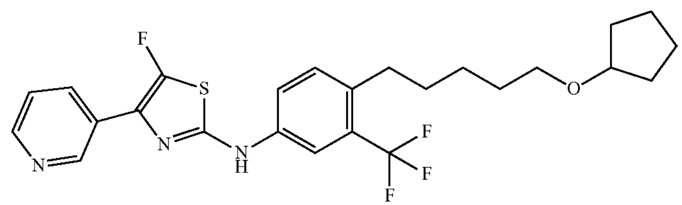 | N-(4-(5-(cyclopentyloxy)pentyl)-3-(trifluoromethyl)phenyl)-5-fluoro-4-(pyridin-3-yl)thiazol-2-amine | | | |
| 229 | 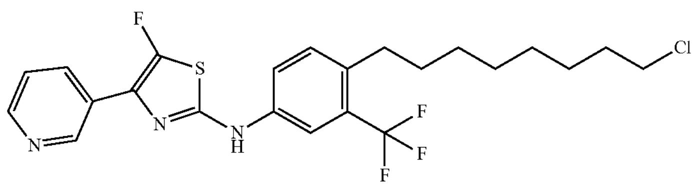 | N-(4-(8-chlorooctyl)-3-(trifluoromethyl)phenyl)-5-fluoro-4-(pyridin-3-yl)thiazol-2-amine | | | |
| 230 | 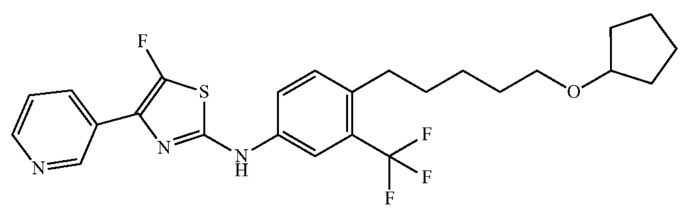 | N-(4-(5-(cyclopentyloxy)pentyl)-3-(trifluoromethyl)phenyl)-5-fluoro-4-(pyridin-3-yl)thiazol-2-amine | +++ | | |
| 231 | 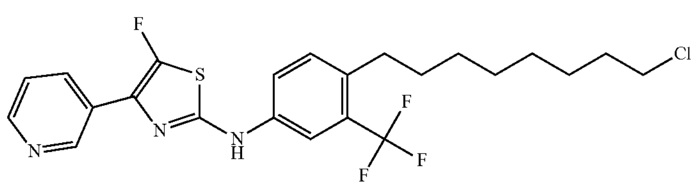 | N-(4-(8-chlorooctyl)-3-(trifluoromethyl)phenyl)-5-fluoro-4-(pyridin-3-yl)thiazol-2-amine | +++ | | |

TABLE 1-continued

TABLE OF COMPOUNDS

| Cmp # | Structure | Name | Activity | rt | M + 1 |
|---|---|---|---|---|---|
| 232 | 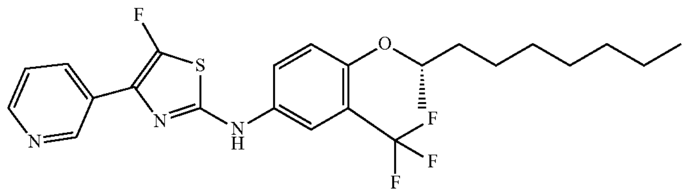 | (S)-5-fluoro-N-(4-(nonan-2-yloxy)-3-(trifluoromethyl)phenyl)-4-(pyridin-3-yl)thiazol-2-amine | +++ | | |
| 233 | 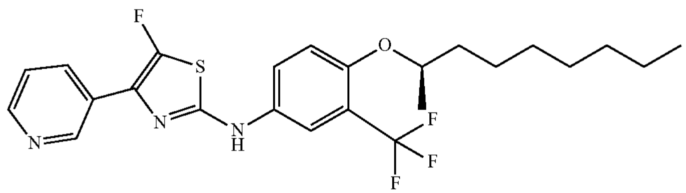 | (R)-5-fluoro-N-(4-(nonan-2-yloxy)-3-(trifluoromethyl)phenyl)-4-(pyridin-3-yl)thiazol-2-amine | +++ | | |
| 234 | 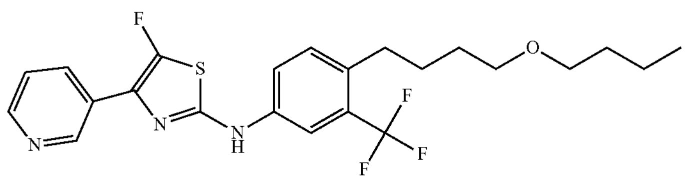 | N-(4-(4-butoxybutyl)-3-(trifluoromethyl)phenyl)-5-fluoro-4-(pyridin-3-yl)thiazol-2-amine | +++ | | |

Example 5

Assay for Identifying Compounds which Inhibit HCV Replication

Compounds claimed herein are tested for the ability to inhibit viral replication of the Hepatitis C replicon in cultured cells in which the HCV replicon construct has been incorporated. The HCV replicon system was described by Bartenschlager, et. al (Science, 285, pp. 110-113 (1999)). The replicon system is predictive of in vivo anti-HCV activity; compounds that are active in humans uniformly evidence activity in the replicon assay.

In this assay HCV replicon containing cells are treated with different concentrations of the test compound to ascertain the ability of the test compound to suppress replication of the HCV replicon. As a positive control, HCV replicon-containing cells are treated with different concentrations of interferon alpha, a known inhibitor of HCV replication. The replicon assay system includes Neomycin Phosphotransferase (NPT) as a component of the replicon itself in order to detect the transcription of replicon gene products in the host cell. Cells in which the HCV replicon is actively replicating have high levels of NPT; the level of NPT is proportional to HCV replication. Cells in which the HCV replicon is not replicating also have low levels of NPT and thus do not survive when treated with Neomycin. The NPT level of each sample is measured using a captured ELISA.

A protocol for testing compounds for the ability to inhibit viral replication of the Hepatitis C replicon cultured cells in which the replicon construct has been incorporated, follows.

5A. HCV Replicon and Replicon Expression

The HCV genome consists of a single ORF that encodes a 3000 amino acid polyprotein. The ORF is flanked on the 5' side by an untranslated region that serves as an internal ribosome entry site (IRES) and at the 3' side by a highly conserved sequence necessary for viral replication (3'-NTR). The structural proteins, necessary for viral infection, are located near the 5' end of the ORF. The non-structural proteins, designated NS2 to NS5B comprise the remainder of the ORF.

The HCV replicon contains, 5'-3', the HCV-IRES, the neomycin phosphotransferase (neo) gene, the IRES of encephalomyocarditis virus, which directs translation of HCV sequences NS3 to NS5B, and the 3'-NTR. The sequence of the HCV replicon has been deposited in GenBank (Accession no. AJ242652).

The replicon is transfected into Huh-7 cells using standard methods such as electroporation.

5B. Cell Maintenance

The equipment and materials include, but are not limited to, Huh-7 HCV replicon-containing cells, maintenance media (DMEM (Dulbecco's modified Eagle media) supplemented with 10% FBS, L-glutamine, non-essential amino acids, penicillin (100 units/ml), streptomycin (100 micrograms/ml), and 500 micrograms/ml of Geneticin (G418), screening media (DMEM supplemented with 10% FBS, L-glutamine, non-essential amino acids, penicillin (100 units/ml) and streptomycin (100 micrograms/ml)), 96 well tissue culture plates (flat bottom), 96 well plates (U bottom for drug dilution), Interferon alpha for positive control, fixation reagent (such as methanol: acetone), primary antibody (rabbit anti-NPTII), secondary antibody: Eu—N1 1, and enhancement solution.

HCV replicon-containing cells support high levels of viral RNA replicon replication when their density is suitable. Over-confluency causes decreased viral RNA replication. Therefore, cells must be kept growing in log phase in the presence of 500 micrograms/ml of G418. Generally, cells should be passed twice a week at 1: 4-6 dilution. Cell maintenance is conducted as follows:

HCV replicon-containing cells are examined under a microscope to ensure that cells growing well. Cells are rinsed once with PBS and 2 ml trypsin is added. The cell/trypsin mixture is incubated at 37° C. in a $CO_2$ incubator for 3-5 minutes. After incubation 10 ml of complete media is added to stop the trypsinization reaction. Cells are blown gently, put into a 15 ml tube, and spun at 1200 rpm for 4 minutes. The trypsin/medium solution is removed. Medium (5 ml) is added and the cells are mixed carefully. The cells are counted.

The cells are then seeded onto 96-well plates at a density of 6000-7500 cells/100 microliters/well (6-7.5×10$^5$ cells/10 ml/plate). The plates are then incubated at 37° C. in a 5% $CO_2$ incubator.

Cells are examined under a microscope approximated 24 hours after seeding and prior to adding drugs. If counting and dilution were performed correctly, cells are 60-70% confluent and nearly all cells should attach and spread evenly in the well.

5C. Treatment of HCV-replicon Containing Cells with Test Compound

HCV replicon-containing cells are rinsed with once PBS once; 2 mls of trypsin are then added. Cells are incubated at 37° C. in a 5% $CO_2$ incubator for 3-5 minutes. 10 mls of complete medium is added to stop the reaction. Cells are blown gently, put into a 15 ml tube, and spun at 1200 rpm for four minutes. The trypsin/medium solution is removed and 5 mls of medium (500 ml DMEM (high glucose)) from BRL catalog #12430-054; 50 mls 10% FBS, 5% Geneticin G418 (50 mg/ml, BRL catalog #10131-035), 5 ml MEM non-essential amino acids (100×BRL #11140-050) and 5 ml penstrep (BRL #15140-148) is added. The cells and media are mixed carefully Cells are plated with screening medium (500 ml DMEM (BRL #21063-029), 50 ml FBS (BRL #10082-147) and 5 ml MEM non-essential amino acid (BRL #11140-050) at 6000-7500 cells/100 µl/well of 96 well plate (6-7.5×10$^5$ cells/10 ml/plate). Plates are placed into 37° C. 5% $CO_2$ incubator overnight.

5D. Assay

The following morning, drugs (test compounds or interferon alpha) are diluted in 96 well U bottom plates with media or DMSO/media, depending on the final concentration chosen for screening. Generally for 6 concentrations of each test compounds ranging from 10 micromolar to 0.03 micromolar are applied. 100 µl of the test compound dilution is placed in wells of the 96 well plate containing the HCV replicon cells. Media without drug is added to some wells as a negative controls. DMSO is known to affect cell growth. Therefore, if drugs diluted in DMSO are used, all wells, including negative control (media only) and positive control (interferon alpha) wells, must contain the same concentration of DMSO, for single dose screening. The plates are incubated at 37° C. in a humidified 5% $CO_2$ environment for three days.

On day four, the NTPII assay is quantitated. The medium is poured from the plates and the plates are washed once in 200 µl of PBS. The PBS is then decanted and the plates tapped in a paper towel to remove any remaining PBS. Cells are fixed in situ with 100 µl/well of pre-cooled (−20° C.) methanol:acetone (1:1) and the plates are placed at −20° C. for 30 minutes.

The fixing solution is poured from the plates and the plates allowed to air-dry completely (approximately one hour). The appearance of the dried cell layer is recorded and the density of the cells in the toxic wells is scored with the naked eye. Alternatively cell viability may be assessed using the MTS assay described below.

The wells are blocked with 200 μl of blocking solution (10% FBS; 3% NGS in PBS) for 30 minutes at room temperature. The blocking solution is removed and 100 μl of rabbit anti-NPTII diluted 1:1000 in blocking solution is added to each well. The plates are then incubated 45-60 minutes at room temperature. After incubation, wells are washed six times with PBS-0.05% Tween-20 solution. 100 μl of 1:15,000 diluted Europium (EU)-conjugated goat anti-rabbit in blocking buffer is added to each well and incubated at room temperature for 30-45 minutes. The plates are washed again and 100 μl of enhancement solution (Perkin Elmer #4001-0010) is added to each well. Each plate is shaken (approx. 30 rpm) in a plate shaker for three minutes. 95 μl is transferred from each well to a black plate; the EU signal is quantitated in a Perkin-Elmer VICTOR plate reader (EU-Lance).

Test Results:
Compounds described in the "TABLE OF COMPOUNDS" is Example 4 have been tested in an HCV replication assay, essentially as described in this example. In that table +++ indicates inhibition of HCV replicon replication of less than 1 micromolar, ++ indicates inhibition of less than 10 micromolar to 1 micromolar, and + indicates inhibition greater than 10 micromolar.

Example 6

Cytotoxicity Assays

To insure that the decrease in replicon replication is due to compound activity against the HCV replicon rather than non-specific toxicity assays are used to quantitate compound cytotoxicity.

Example 6A

Cellular Protein Albumin Assay for Cytotoxicity

Cellular protein albumin measurements provide one marker of cytotoxicity. The protein levels obtained from cellular albumin assays may also be used to provide a normalization reference for antiviral activity of compounds. In the protein albumin assay HCV replicon-containing cells are treated for three days with different concentrations of helioxanthin; a compound that is known to be cytotoxic at high concentrations. The cells are lysed and the cell lysate used to bind plate-bound goat anti-albumin antibody at room temperature (25° C. to 28° C.) for 3 hours. The plate is then washed 6 times with 1×PBS. After washing away the unbound proteins, mouse monoclonal anti-human serum albumin is applied to bind the albumin on the plate. The complex is then detected using phosphatase-labeled anti-mouse IgG as a second antibody.

Example 6B

MTS Assay for Cytotoxicity

Cell viability may also be determined by CELLTITER 96 AQUEOUS ONE Solution Cell Proliferation Assay (Promega, Madison Wis.), a colorimetric assay for determining the number of viable cells. In this method, before fixing the cells, 10-20 μl MTS reagent is added to each well according to manufacturer's instructions, plates are incubated at 37° C. and read at OD 490 nm. During the incubation period living cells covert the MTS reagent to a formazan product which absorbs at 490 nm. Thus the 490 nm absorbance is directly proportional to the number of living cells in culture.

A direct comparison of the Cellular Album and MTS methods for determining cytotoxicity may be obtained as follows: Cells are treated with different concentrations of test compound or Helioxanthin for a three day-period. Prior to lysis for detection album as described above, the MTS reagent is added according to manufacturer's instruction to each well and incubate at 37° C. and read at OD 490 nm. The cellular album quantitation is then performed as described above.

What is claimed is:
1. A compound of Formula I or Formula II, or pharmaceutically acceptable salt, wherein:

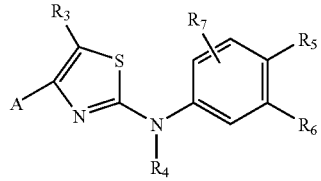

(Formula I)

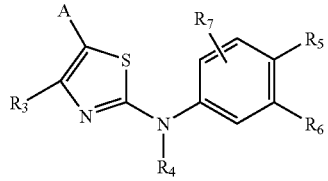

(Formula II)

A is a monocyclic or bicyclic group of the formula:

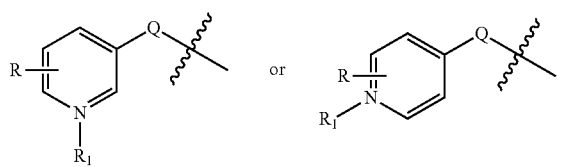

where Q is O, S, N, CH$_2$, or absent;
R represents 0 or 1 or more substituents independently chosen from
(a) hydroxyl, halogen, amino, cyano, —COOH, —CONH$_2$, —PO$_4$, C$_1$-C$_2$haloalkyl, and C$_1$-C$_2$haloalkoxy; and
(b) C$_1$-C$_4$alkyl, C$_1$-C$_4$alkoxy, mono- and di-C$_1$-C$_4$alkylamino, C$_2$-C$_4$alkanoyl, mono- and di-C$_1$-C$_4$alkylphosphate, and C$_1$-C$_4$alkylester, each of which is substituted with 0 or 1 or more substituents independently chosen from halogen, hydroxyl, amino, cyano, C$_1$-C$_2$alkoxy, and mono- and di- C$_1$-C$_2$alkylamino; or
any two R groups, covalently bound to adjacent atoms, may be joined to form a 5-membered heterocyclic group containing 1 or 2 additional heteroatoms independently chosen from N, O, and S, wherein the 5-membered heterocyclic group is optionally substituted with an oxo group;
R$_1$ is absent, oxygen, or C$_1$-C$_4$alkyl; or
R and R$_1$ may be joined to form a 5-membered heterocyclic group containing 1 or 2 additional heteroatoms independently chosen from N,O, and S, when R and R$_1$ are bound to adjacent atoms;

$R_3$ is hydrogen, halogen, hydroxyl, amino, cyano, $C_1$-$C_2$alkyl, or (mono- or di-$C_1$-$C_2$alkylamino)$C_0$-$C_2$alkyl;

$R_4$ is hydrogen, amino, $C_1$-$C_2$alkyl, or $C_2$-$C_4$alkenylamino;

$R_4$ is $C_1$-$C_6$alkyl, $C_2$-$C_6$alkenyl, mono- or di-$C_1$-$C_6$alkylamino, or $C_2$-$C_6$alkenylamino, each of which alkyl or alkenyl chain contains 0 or 1 to 4 oxygen atoms and each of which is substituted with 0 or 1 or more substituents independently chosen from amino, hydroxyl, —COOH, $C_1$-$C_4$alkoxy, mono- and di-$C_1$-$C_4$alkylamino, mono- and di-$C_1$-$C_4$alkylcarboxamide, and $C_1$-$C_4$alkylester;

$R_7$ is 0 or 1 or more substituents independently chosen from halogen, hydroxyl, amino, cyano, $C_1$-$C_2$alkyl, $C_1$-$C_2$alkoxy, $C_1$-$C_2$haloalkyl, and $C_1$-$C_2$haloalkoxy, and wherein one or more of the following conditions (i) to (vii) is met:

(i) $R_5$ is $C_6$-$C_{20}$carbohydryl, $C_6$-$C_{20}$carbohydryloxy, $C_2$-$C_{20}$alkanoyl, or $C_6$-$C_{20}$mono- or di-alkylamino, where the carbohydryl, carbohydryloxy, alkanoyl or mono- or di-alkylamino chain may be substituted with one or more halogen, hydroxyl, cyano, amino, $C_1$-$C_2$haloalkyl, $C_1$-$C_2$haloalkoxy, and oxo, and $R_6$ is halogen, hydroxyl, amino, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;

(ii) $R_6$ is $C_4$-$C_{20}$carbohydryl, $C_4$-$C_{20}$carbohydryloxy, or $C_2$-$C_{20}$alkanoyl, where the carbohydryl, carbohydryloxy, or alkanoyl chain may be substituted with one or more substituents independently chosen from halogen, hydroxyl, cyano, amino, $C_1$-$C_2$haloalkyl, $C_1$-$C_2$haloalkoxy, and oxo, and $R_5$ is halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;

(iii) one of $R_5$ and $R_6$ is $C_4$-$C_{20}$carbohydryl, $C_4$-$C_{20}$carbohydryloxy, or $C_2$-$C_{20}$alkanoyl, where the carbohydryl, carbohydryloxy, or alkanoyl chain contains one or more oxygen atoms, nitrogen atoms, sulfur atoms, or sulfonyl groups and may be substituted with one or more independently chosen halogen, hydroxyl, cyano, amino, $C_1$-$C_2$haloalkyl, $C_1$-$C_2$haloalkoxy, and oxo, and the other of $R_5$ and $R_6$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;

(iv) one of $R_5$ and $R_6$ is —O(CH$_2$)$_2$O—, or $C_4$-$C_{20}$carbohydryl, $C_4$-$C_{20}$carbohydryloxy, or $C_4$-$C_{10}$alkanoyl, where the carbohydryl, carbohydryloxy, or alkanoyl chain may contain one or more oxygen atoms, nitrogen atoms, sulfur atoms, or sulfonyl groups and may be substituted with one or more independently chosen halogen, hydroxyl, cyano, amino, $C_1$-$C_2$haloalkyl, $C_1$-$C_2$haloalkoxy, and oxo, and where the group of the formula —O(CH$_2$)$_2$O—, or the $C_4$-$C_{10}$carbohydryl, $C_4$-$C_{10}$carbohydryloxy, or $C_4$-$C_{10}$alkanoyl is substituted with one aryl, mono- or bicyclic heteroaryl, $C_3$-$C_7$cycloalkyl, or 5- to 7- membered heterocycloalkyl, each of which is substituted with 0 or 1 or more substituents independently chosen from halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy; and the other of $R_5$ and $R_6$ is hydrogen, halogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy;

(v) one of $R_5$ and $R_6$ is phenoxy, benzyloxy, or indanyloxy; each of which is substituted with 0 or 1 or more independently chosen halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy;

(vi) one of $R_5$ and $R_6$ is ($C_3$-$C_7$cycloalkyl)$C_0$-$C_2$alkyl or ($C_3$-$C_7$cycloalkyl)$C_0$-$C_2$alkoxy and the other of $R_5$ and $R_6$ is hydrogen, hydroxyl, amino, cyano, —COOH, —CONH$_2$, $C_1$-$C_4$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and (vii) $R_5$ and $R_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, hydroxyl, amino, cyano, $C_1$-$C_{10}$alkyl, $C_2$-$C_{10}$alkenyl, $C_1$-$C_{10}$alkoxy, and (phenyl)$C_0$-$C_4$alkyl;

wherein the compound is not:

N-(3-(trifluoromethyl)-4-(pentyloxy)phenyl)-4-(pyridin-3-yl)thiazol-2-amine;

4-(6-((dimethylamino)methyl)pyridin-3-yl)-N-(4-(pentyloxy)-3-(trifluoromethyl)phenyl)thiazol-2-amine;

N-(3-fluoro-4-(pentyloxy)phenyl)-4-(pyridin-3-yl)thiazol-2-amine;

N-(4-((piperidin-1-yl)methyl)phenyl)-4-(pyridin-3-yl)thiazol-2-amine;

N-(3-(2,3-dihydro-1H-inden-2-yloxy)phenyl)-4-(pyridin-3-yl)thiazol-2-amine;

N-(4-(cyclohexylmethoxy)-3-fluorophenyl)-4-(pyridin-3-yl)thiazol-2-amine;

5-(4-(pyridin-3-yl)thiazol-2-ylamino)-2-(heptyloxy)benzonitrile;

N-(3-methyl-4-(pentyloxy)phenyl)-4-(pyridin-3-yl)thiazol-2-amine;

N-(4-butoxy-3-(trifluoromethyl)phenyl)-4-(pyridin-3-yl)thiazol-2-amine;

N-(4-(pentyloxy)phenyl)-4-(pyridin-3-yl)thiazol-2-amine;

N-(4-pentylphenyl)-4-(pyridin-3-yl)thiazol-2-amine;

N-(3-(benzyloxy)phenyl)-4-(pyridin-3-yl)thiazol-2-amine;

N-(3-phenoxyphenyl)-4-(pyridin-3-yl)thiazol-2-amine;

N-(3-(phenethyloxy)phenyl)-4-(pyridin-3-yl)thiazol-2-amine;

N-(4-(hexyloxy)phenyl)-4-(pyridin-3-yl)thiazol-2-amine;

N-(4-butoxyphenyl)-4-(pyridin-3-yl)thiazol-2-amine;

N-(4-(heptyloxy)phenyl)-4-(pyridin-3-yl)thiazol-2-amine;

N-(4-(octyloxy)phenyl)-4-(pyridin-3-yl)thiazol-2-amine;

N-(4-hexylphenyl)-4-(pyridin-3-yl)thiazol-2-amine;

N-(4-octylphenyl)-4-(pyridin-3-yl)thiazol-2-amine;

N-(4-butylphenyl)-4-(pyridin-3-yl)thiazol-2-amine;

N-(3-benzylphenyl)-4-(pyridin-3-yl)thiazol-2-amine;

2-(4-(4-(pyridin-3-yl)thiazol-2-ylamino)phenyl)acetonitrile;

N1-isopropyl-N1-phenyl-N4-(4-(pyridin-3-yl)thiazol-2-yl)benzene-1,4-diamine;

butyl 4-(4-(pyridin-3-yl)thiazol-2-ylamino)benzoate;
ethyl 2-(4-(4-(pyridin-3-yl)thiazol-2-ylamino)phenyl)acetate;
N-(4-propylphenyl)-4-(pyridin-3-yl)thiazol-2-amine;
N-(4-phenoxyphenyl)-4-(pyridin-3-yl)thiazol-2-amine;
N-(3-(trifluoromethyl)-4-(pentyloxy)phenyl)-4-(6-methylpyridin-3-yl)thiazol-2-amine;
N-(3-(trifluoromethyl)-4-(pentyloxy)phenyl)-4-(pyrazin-2-yl)thiazol-2-amine; and
N-(3-(trifluoromethyl)-4-(pentyloxy)phenyl)-N-methyl-4-(pyridin-3-yl)thiazol-2-amine.

2. A compound or salt of claim 1, wherein
$R_5$ is $C_6$-$C_{10}$alkyl, $C_6$-$C_{10}$alkenyl, $C_6$-$C_{10}$alkoxy, $C_6$-$C_{10}$alkenyloxy, or $C_6$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and
$R_6$ is halogen, —COOH, —CONH$_2$, $C_1$-$C_2$alkyl, $C_1$-$C_2$alkoxy, methylester, methylsulfonyl, —CF$_2$CH$_3$, trifluormethyl, or trifluoromethoxy.

3. A compound or salt of claim 1, wherein $R_6$ is $C_4$-$C_{10}$alkyl, $C_4$-$C_{10}$alkenyl, $C_4$-$C_{10}$alkoxy, $C_4$-$C_{10}$alkenyloxy, or $C_4$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and
$R_5$ is hydrogen, halogen, cyano, —COOH, —CONH$_2$, $C_1$-$C_2$alkyl, $C_1$-$C_2$alkoxy, methylester, methylsulfonyl, —CF$_2$CH$_3$, trifluormethyl, or trifluoromethoxy.

4. A compound or salt of claim 1, wherein one of $R_5$ and $R_6$ is a group of the formula —O(CH$_2$)$_2$O—, $C_4$-$C_{10}$carbohydryl, $C_4$-$C_{10}$carbohydryloxy, or $C_4$-$C_{10}$alkanoyl, where the carbohydryl, carbohydryloxy, or alkanoyl chain may contain one or more oxygen atoms and may be substituted with one or more halogen, hydroxyl, cyano, amino, $C_1$-$C_2$haloalkyl, $C_1$-$C_2$haloalkoxy, and oxo, and where the group of the formula —O(CH$_2$)$_2$O—, $C_4$-$C_{10}$carbohydryl, $C_4$-$C_{10}$carbohydryloxy, or $C_4$-$C_{10}$alkanoyl is substituted with one phenyl, naphthyl, pyridyl, pyrimidinyl, pyrazinyl, thienyl, pyrrolyl, furanyl, pyrazoloyl, imidazolyl, pyrrolidinyl, piperidinyl, piperazinyl, morpholinyl, $C_3$-$C_7$cycloalkyl, or 5- to 7- membered heterocycloalkyl, each of which is substituted with 0 or 1 or more halogen, hydroxyl, cyano, $C_1$-$C_4$alkyl, $C_1$-$C_4$alkoxy, $C_2$-$C_4$alkanoyl, mono- or di-$C_1$-$C_4$alkylamino, $C_1$-$C_2$haloalkyl, or $C_1$-$C_2$haloalkoxy; and
the other of $R_5$ and $R_6$ is hydrogen, halogen, cyano,—COOH, —CONH$_2$, $C_1$-$C_2$alkyl, $C_1$-$C_2$alkoxy, methylester, methylsulfonyl, trifluormethyl, or trifluoromethoxy.

5. A compound or salt of claim 1, wherein
one of $R_5$ and $R_6$ is phenoxy, benzyloxy, or indanyloxy; each of which is substituted with 0, 1 or 2 substituents independently chosen from halogen, cyano, $C_1$-$C_2$alkyl, $C_1$-$C_2$alkoxy, mono- or di-$C_1$-$C_4$alkylamino, trifluoromethyl, or trifluoromethoxy;
the other of $R_5$ and $R_6$ is halogen, hydroxyl, amino, cyano, —COOH, —CONH$_2$, $C_1$-$C_2$alkyl, $C_1$-$C_2$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy.

6. A compound or salt of claim 1 wherein
one of $R_5$ and $R_6$ is (cyclohexyl)$C_1$-$C_2$alkyl or (cyclohexyl) $C_1$-$C_2$alkoxy and the other of $R_5$ and $R_6$ is hydrogen, —COOH, —CONH$_2$, $C_1$-$C_2$alkyl, $C_1$-$C_2$alkoxy, methylester, $C_1$-methylsulfonyl, trifluoromethyl, or trifluoromethoxy.

7. A compound or salt of claim 1, wherein
$R_5$ and $R_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, cyano, $C_1$-$C_8$alkyl, $C_1$-$C_8$alkoxy, and (phenyl)$C_1$-$C_4$alkyl.

8. A compound or salt of claim 1, wherein $R_1$ is hydrogen.

9. A compound or salt of claim 1, wherein
A is

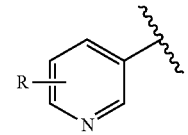

in which
R represents 0 or 1 or more substituents independently chosen from
(a) hydroxyl, halogen, amino, cyano, —COOH, —CONH$_2$, —PO$_4$, $C_1$-$C_2$haloalkyl, and $C_1$-$C_2$haloalkoxy; and
(b) $C_1$-$C_4$alkyl, $C_1$-$C_4$alkoxy, mono- and di-$C_1$-$C_4$alkylamino, $C_2$-$C_4$alkanoyl, mono- and di-$C_1$-$C_4$alkylphosphate, and $C_1$-$C_4$alkylester, each of which is substituted with 0 or 1 or more substituents independently chosen from halogen, hydroxyl, amino, cyano, $C_1$-$C_2$alkoxy, mono- and di- $C_1$-$C_2$alkylamino.

10. A compound or salt of claim 9, wherein:
R is absent or R is hydroxyl, halogen, cyano, —CONH$_2$, $C_1$-$C_2$alkyl, $C_1$-$C_2$alkoxy, or mono- or di-$C_1$-$C_2$alkylphosphate.

11. A compound or salt of claim 9, wherein:
A is 3-pyridyl and R is absent or hydroxyl, fluoro, chloro, cyano, —CONH$_2$, methyl, methoxy, or di-methyl phosphate.

12. A compound or salt of claim 1, wherein
A is

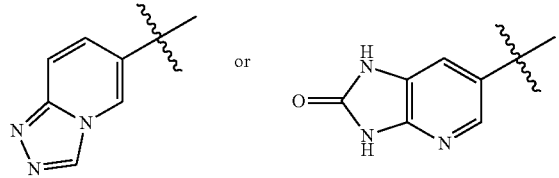

13. A compound or salt of claim 1, wherein $R_3$ is halogen.
14. A compound or salt of claim 1, wherein $R_4$ is hydrogen.
15. A compound or salt of claim 1, wherein
$R_5$ is halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and
$R_6$ is $C_4$-$C_{10}$alkyl, $C_4$-$C_{10}$alkenyl, $C_4$-$C_{10}$alkoxy, or $C_2$-$C_{10}$akanoyl, each of which may contain one or more oxygen atoms, nitrogen atoms, sulfur atoms or sulfonyl groups and may be substituted with one or more independently chosen halogen, hydroxyl, cyano, amino, $C_1$-$C_2$haloalkyl, $C_1$-$C_2$haloalkoxy, and oxo; or
$R_5$ is halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and $R_6$ is $C_6$-$C_{10}$alkyl, $C_6$-$C_{10}$alkenyl, $C_6$-$C_{10}$alkoxy, or $C_2$-$C_{10}$akanoyl, each of which may contain one or more oxygen atoms, nitrogen atoms, sulfur atoms or sulfonyl groups and may be substituted with one or more independently chosen halogen, hydroxyl, cyano, amino, $C_1$-$C_2$haloalkyl, $C_1$-$C_2$haloalkoxy, and oxo.

16. A compound or salt of claim 1, wherein
one of $R_5$ and $R_6$ is hydrogen, halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$alkylsulfonyl, $C_1$-$C_2$haloalkyl, or $C_1$-$C_2$haloalkoxy; and
is the other of $R_5$ and $R_6$ is $C_4$-$C_{10}$carbohydryl, $C_4$-$C_{10}$carbohydryloxy, or $C_2$-$C_8$alkanoyl,
where each carbohydryl, carbohydryloxy, or alkanoyl chain may contain one or more oxygen atoms, nitrogen atoms, sulfur atoms, or sulfonyl groups and may be substituted with one or more halogen, hydroxyl, cyano, amino, $C_1$-$C_2$haloalkyl, $C_1$-$C_2$haloalkoxy, and oxo, and each of which carbohydryl, carbohydryloxy, alkanoyl, or alkylamino chain is substituted with one aryl, mono- or bicyclic heteroaryl, $C_3$-$C_7$cycloalkyl, or 5- to 7-membered heterocycloalkyl, each of which is substituted with 0 or 1 or more substituents independently chosen from halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy; or
is the other of $R_5$ and $R_6$ is phenyloxy, indanyloxy, thienyloxy, or pyridyloxy, each of which is substituted with 0 or 1 or more substituents independently chosen from halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy.

17. A compound or salt of claim 16, wherein
one of $R_5$ and $R_6$ is hydrogen, halogen, hydroxyl, amino, cyano, —COOH, —CONH$_2$, —SO$_2$CH$_3$, $C_1$-$C_2$alkyl, $C_1$-$C_4$alkoxy, $C_2$-$C_4$alkanoyl, $C_1$-$C_2$alkylester, $C_1$-$C_2$haloalkyl, or $C_1$-$C_2$haloalkoxy; and
the other of $R_5$ and $R_6$ is $C_4$-$C_{10}$carbohydryl or $C_4$-$C_{10}$carbohydryloxy where each carbohydryl or carbohydryloxy chain may contain one or more oxygen atoms, and may be substituted with one or more independently chosen halogen, hydroxyl, cyano, amino, $C_1$-$C_2$haloalkyl, $C_1$-$C_2$haloalkoxy, and oxo, and each of which each carbohydryl or carbohydryloxy chain is substituted with one phenyl, naphthyl, pyridyl, thienyl, quinolinyl, isoquinolinyl, indolyl, $C_3$-$C_7$cycloalkyl, or 5- to 7- membered heterocycloalkyl, each of which is substituted with 0 or 1 or more substituents independently chosen halogen, hydroxyl, cyano, $C_1$-$C_4$alkyl, $C_1$-$C_4$alkoxy, $C_2$-$C_4$alkanoyl, mono- and di-$C_1$-$C_4$alkylamino, $C_1$-$C_2$haloalkyl, and $C_1$-$C_2$haloalkoxy; or
the other of $R_5$ and $R_6$ is phenyloxy, indanyloxy, or thienyloxy, each of which is substituted with 0 or 1 or more halogen, hydroxyl, cyano, $C_1$-$C_2$alkyl, $C_1$-$C_2$alkoxy, acetyl, mono- or di -$C_1$-$C_2$alkylamino, $C_1$-$C_2$haloalkyl, or $C_1$-$C_2$haloalkoxy; where one of $R_5$ and $R_6$ is L and the other is M.

18. A compound or salt of claim 1, wherein
$R_5$ and $R_6$ are taken together to form a 5- or 6-membered ring, which is saturated, partially unsaturated, or aromatic, contains 0, 1, or 2 heteroatoms chosen from N, O, and S, and is substituted with 0, 1, or 2 substituents independently chosen from halogen, hydroxyl, amino, cyano, $C_1$-$C_8$alkyl, $C_2$-$C_8$alkenyl, $C_1$-$C_8$alkoxy, oxo, and (phenyl)$C_0$-$C_4$alkyl.

19. A compound or salt of claim 1, wherein $R_7$ is hydrogen, halogen, or methyl.

20. A compound or salt of claim 1 of the Formula:

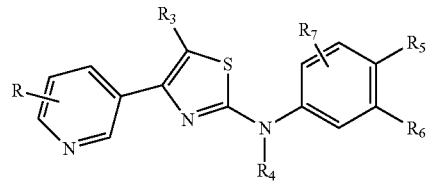

wherein:
R is absent or R is hydroxyl, halogen, cyano, —CONH$_2$, $C_1$-$C_2$alkyl, $C_1$-$C_2$alkoxy, or mono- or di-$C_1$-$C_2$alkylphosphate;
$R_3$ is hydrogen, halogen, amino, hydroxyl, methyl, dimethylamino, or dimethylaminomethyl;
$R_4$ is hydrogen;
$R_5$ and $R_6$ are taken together to form a 5-membered heteroaryl ring, containing 1 or 2 heteroatoms chosen from N and O, and substituted with 0, 1, or 2 substituents independently chosen from halogen, $C_1$-$C_8$alkyl, $C_1$-$C_8$alkoxy, and (phenyl)$C_0$-$C_4$alkyl; and
$R_7$ is hydrogen, halogen, or methyl.

21. A compound or salt of claim 1 of the Formula:

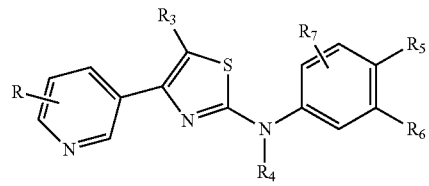

wherein:
R is absent or R is hydroxyl, halogen, cyano, —CONH$_2$, $C_1$-$C_2$alkyl, $C_1$-$C_2$alkoxy, or mono- or di-$C_1$-$C_2$alkylphosphate;
$R_3$ is hydrogen or halogen;
$R_4$ is hydrogen;
$R_5$ is $C_6$-$C_{10}$alkyl, $C_6$-$C_{10}$alkenyl, $C_6$-$C_{10}$alkoxy, $C_6$-$C_{10}$alkenyloxy, or $C_6$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and
$R_6$ is halogen, —COOH, —CONH$_2$, $C_1$-$C_2$alkyl, $C_1$-$C_2$alkoxy, methylester, methylsulfonyl, trifluormethyl, difluoroethyl, or trifluoromethoxy; OR
$R_6$ is $C_4$-$C_{10}$alkyl, $C_4$-$C_{10}$alkenyl, $C_4$-$C_{10}$alkoxy, $C_4$-$C_{10}$alkenyloxy, or $C_4$-$C_{10}$alkanoyl, where the alkyl, alkenyl, alkoxy, alkenyloxy, or alkanoyl chain may contain one or more oxygen atoms, nitrogen atoms, sulfur atoms, or sulfonyl groups, and
$R_5$ is halogen, —COOH, —CONH$_2$, $C_1$-$C_2$alkyl, $C_1$-$C_2$alkoxy, methylester, methylsulfonyl, trifluormethyl, difluoroethyl, or trifluoromethoxy; OR One of R$_5$ and R$_6$ is C$_4$-C$_{20}$carbohydryl, C$_4$-C$_{20}$carbohydryloxy, or C$_2$-C$_{20}$alkanoyl, where the carbohydryl, carbohydryloxy, or alkanoyl chain contains one or more oxygen atoms, nitrogen atoms, sulfur atoms, or sulfonyl groups and may be substituted with one or more independently chosen halogen, hydroxyl, cyano, amino, C$_1$-C$_2$haloalkyl, C$_1$-C$_2$haloalkoxy, and oxo, and the other of R$_5$ and R$_6$ is hydrogen, halogen, hydroxyl, amino, cyano, —COOH, —CONH$_2$, C$_1$-C$_4$alkyl, C$_1$-C$_4$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy; OR One of R$_5$ and R$_6$ is a group of the formula —O(CH$_2$)$_2$O—, or C$_4$-C$_{10}$carbohydryl, C$_4$-C$_{10}$carbohydryloxy, or C$_4$-C$_{10}$alkanoyl, where the carbohydryl, carbohydryloxy, or alkanoyl chain may contain one or more oxygen atoms and may be substituted with one or more halogen, hydroxyl, cyano, amino, C$_1$-C$_2$haloalkyl, C$_1$-C$_2$haloalkoxy, and oxo, and where the group of the formula —O(CH$_2$)$_2$O—, or C$_4$-C$_{10}$carbohydryl, C$_4$-C$_{10}$carbohydryloxy, or C$_4$-C$_{10}$alkanoyl is substituted with one phenyl, naphthyl, pyridyl, pyrimidinyl, pyrazinyl, thienyl, pyrrolyl, furanyl, pyrazoloyl, imidazolyl, pyrrolidinyl, piperidinyl, piperazinyl, morpholinyl, C$_3$-C$_7$cycloalkyl, or 5- to 7- membered heterocycloalkyl, each of which is substituted with 0 or 1 or more independently chosen halogen, hydroxyl, cyano, C$_1$-C$_4$alkyl, C$_1$-C$_4$alkoxy, C$_2$-C$_4$alkanoyl, mono- and di-C$_1$-C$_4$alkylamino, C$_1$-C$_2$haloalkyl, and C$_1$-C$_2$haloalkoxy; and the other of R$_5$ and R$_6$ is hydrogen, halogen, cyano,—COOH, —CONH$_2$, C$_1$-C$_2$alkyl, C$_1$-C$_2$alkoxy, methylester, methylsulfonyl, trifluormethyl, or trifluoromethoxy; OR One of R$_5$ and R$_6$ is phenoxy, benzyloxy, or indanyloxy; each of which is substituted with 0, 1 or 2 substituents independently chosen from halogen, cyano, C$_1$-C$_2$alkyl, C$_1$-C$_2$alkoxy, mono- or di-C$_1$-C$_4$alkylamino, trifluoromethyl, or trifluoromethoxy;

the other of R$_5$ and R$_6$ is halogen, hydroxyl, amino, cyano, —COOH, —CONH$_2$, C$_1$-C$_2$alkyl, C$_1$-C$_2$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy; OR One of R$_5$ and R$_6$ is (cyclohexyl)C$_1$-C$_2$alkyl or (cyclohexyl)C$_1$-C$_2$alkoxy and the other of R$_5$ and R$_6$ is hydrogen, —COOH, —CONH$_2$, C$_1$-C$_2$alkyl, C$_1$-C$_2$alkoxy, methylester, C$_1$-methylsulfonyl, trifluoromethyl, or trifluoromethoxy; and the other of R$_6$ is halogen, hydroxyl, amino, cyano, —COOH, —CONH$_2$, C$_1$-C$_4$alkyl, C$_1$-C$_4$alkoxy, C$_2$-C$_4$alkanoyl, C$_1$-C$_2$alkylester, C$_1$-C$_2$alkylsulfonyl, C$_1$-C$_2$haloalkyl, or C$_1$-C$_2$haloalkoxy; OR R$_5$ and R$_6$ are taken together to form a 5- or 6-membered heterocyclic ring containing 1 or 2 heteroatoms independently chosen from O and N, which ring is partially unsaturated or aromatic, and is substituted with 0, 1, or 2 substituents independently chosen from halogen, hydroxyl, amino, cyano, C$_1$-C$_{10}$alkyl, C$_2$-C$_{10}$alkenyl, C$_1$-C$_{10}$alkoxy, and (phenyl)C$_0$-C$_4$alkyl; and R$_7$ is hydrogen, halogen, or methyl.

22. A compound or salt of claim 21, wherein R$_3$ is fluoro.

23. A compound or salt of claim 1 of the Formula

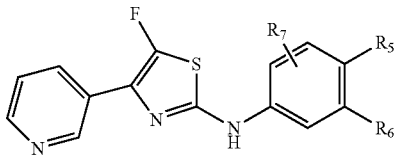

wherein:

R$_5$ is C$_4$-C$_{10}$alkyl or C$_4$-C$_{10}$alkoxy, each of which is substituted with 0 or 1 or more halogen, hydroxyl, cyano, C$_1$-C$_2$alkyl, C$_1$-C$_2$alkoxy, C$_2$-C$_4$alkanoyl, mono- or di-C$_1$-C$_2$alkylamino, C$_1$-C$_2$haloalkyl, or C$_1$-C$_2$haloalkoxy; and R$_6$ is halogen, cyano, —CONH$_2$, —COOH, methyl, methoxy, acetyl, trifluoromethyl, —CF$_2$CH$_3$, or trifluoromethoxy; and R$_7$ is hydrogen, halogen, or methyl.

24. A compound of claim 1 or a pharmaceutically acceptable salt thereof, wherein the compound is N-(4-(2-(heptylsulfonyl)ethyl)phenyl)-4-(pyridin-3-yl)thiazol-2-amine;

N-(4-(5-phenylpentyloxy)-3-(trifluoromethyl)phenyl)-4-(pyridin-3-yl)thiazol-2-amine;

4-(pyridin-3-yl)-N-(4-(4-o-tolylbutoxy)-3-(trifluoromethyl)phenyl)thiazol-2-amine;

N-(4-(4-(4-chlorophenyl)butoxy)-3-(trifluoromethyl)phenyl)-4-(pyridin-3-yl)thiazol-2-amine;

N-(4-(4-(4-fluorophenyl)but-3-ynyloxy)-3-(trifluoromethyl)phenyl)-4-(pyridin-3-yl)thiazol-2-amine;

N-(4-methyl-3-(octyloxy)phenyl)-4-(pyridin-3-yl)thiazol-2-amine;

N-(4-methyl-3-(pentyloxy)phenyl)-4-(pyridin-3-yl)thiazol-2-amine;

2-(pentyloxy)-4-(4-(pyridin-3-yl)thiazol-2-ylamino)benzonitrile;

5-fluoro-N-(4-methyl-3-(octyloxy)phenyl)-4-(pyridin-3-yl)thiazol-2-amine;

5-fluoro-N-(4-methyl-3-(pentyloxy)phenyl)-4-(pyridin-3-yl)thiazol-2-amine;

4-((5-fluoro-4-(pyridin-3-yl)thiazol-2-ylamino)-2-(pentyloxy)benzonitrile;

5-fluoro-N-(4-octylphenyl)-4-(pyridin-3-yl)thiazol-2-amine;

(E)-2-(1-(4-(octyloxy)phenyl)-2-propylidenehydrazinyl)-4-(pyridin-3-yl)thiazole;

(E)-2-(2-ethylidene-1-(4-(octyloxy)-3-(trifluoromethyl)phenyl)hydrazinyl)-4-(pyridin-3-yl)thiazole;

(E)-2-(2-ethylidene-1-(4-(octyloxy)phenyl)hydrazinyl)-4-(pyridin-3-yl)thiazole;

5-fluoro-N-(4-octyl-3-(trifluoromethyl)phenyl)-4-(pyridin-3-yl)thiazol-2-amine;

N-(4-methyl-3-(2-phenoxyethoxy)phenyl)-4-(pyridin-3-yl)thiazol-2-amine;

N-(3-(cyclohexylmethoxy)-4-methylphenyl)-4-(pyridin-3-yl)thiazol-2-amine;

2-(1-(4-(octyloxy)-3-(trifluoromethyl)phenyl)hydrazinyl)-4-(pyridin-3-yl)thiazolo;

N-(4-phenoxy-3-(trifluoromethyl)phenyl)-4-(pyridin-3-yl)thiazol-2-amine;

4-(4-(pyridin-3-yl)thiazol-2-ylamino)-2-(trifluoromethyl)phenoxy)benzonitrile;

N-(4-(4-ethylphenoxy)-3-(trifluoromethyl)phenyl)-4-(pyridin-3-yl)thiazol-2-amine;

N-(4-(4-chlorophenoxy)-3-(trifluoromethyl)phenyl)-4-(pyridin-3-yl)thiazol-2-amine;
5-fluoro-N-(4-methyl-3-(2-phenoxyethoxy)phenyl)-4-(pyridin-3-yl)thiazol-2-amine;
N-(3-(cyclohexylmethoxy)-4-methylphenyl)-5-fluoro-4-(pyridin-3-yl)thiazol-2-amine;
2-pentyl-N-(4-(pyridin-3-yl)thiazol-2-yl)benzo[d]oxazol-5-amine;
N-(5-fluoro-4-(pyridin-3-yl)thiazol-2-yl)-2-pentylbenzo[d]oxazol-5-amine;
2-pentyl-N-(4-(pyridin-3-yl)thiazol-2-yl)benzo[d]oxazol-6-amine;
N-(5-fluoro-4-(pyridin-3-yl)thiazol-2-yl)-2-pentylbenzo[d]oxazol-6-amine;
N-(3-(octyloxy)-4-(trifluoromethyl)phenyl)-4-(pyridin-3-yl)thiazol-2-amine;
N-(3-(pentyloxy)-4-(trifluoromethyl)phenyl)-4-(pyridin-3-yl)thiazol-2-amine;
5-fluoro-N-(4-phenoxy-3-(trifluoromethyl)phenyl)-4-(pyridin-3-yl)thiazol-2-amine;
4-(pyridin-3-yl)-N-(4-(5-p-tolylpentyl)-3-(trifluoromethyl)phenyl)thiazol-2-amine;
5-fluoro-N-(3-(octyloxy)-4-(trifluoromethyl)phenyl)-4-(pyridin-3-yl)thiazol-2-amine;
5-fluoro-N-(3-(pentyloxy)-4-(trifluoromethyl)phenyl)-4-(pyridin-3-yl)thiazol-2-amine;
N-(3-octyl-5-(trifluoromethyl)phenyl)-4-(pyridin-3-yl)thiazol-2-amine;
1-(5-(5-fluoro-4-(pyridin-3-yl)thiazol-2-ylamino)-2-phenoxyphenyl)ethanone;
N-(3-(1,1-difluoroethyl)-4-phenoxyphenyl)-5-fluoro-4-(pyridin-3-yl)thiazol-2-amine;
1-(2-(4-chlorophenoxy)-5-(4-(pyridin-3-yl)thiazol-2-ylamino)phenyl)ethanone;
1-(2-(4-chlorophenoxy)-5-(4-(pyridin-3-yl)thiazol-2-ylamino)phenyl)ethanone;
1-(2-phenoxy-5-(4-(pyridin-3-yl)thiazol-2-ylamino)phenyl)ethanone;
N-(4-(4-(4-(dimethylamino)phenyl)butoxy)-3-(trifluoromethyl)phenyl)-4-(pyridin-3-yl)thiazol-2-amine;
5-fluoro-4-(pyridin-3-yl)-N-(4-(4-(thiophen-2-yl)butoxy)-3-(trifluoromethyl)phenyl)thiazol-2-amine;
4-(pyridin-3-yl)-N-(4-(3-(m-tolyloxy)propyl)-3-(trifluoromethyl)phenyl)thiazol-2-amine;
5-fluoro-4-(pyridin-3-yl)-N-(4-(3-(m-tolyloxy)propyl)-3-(trifluoromethyl)phenyl)thiazol-2-amine;
N-(5-fluoro-4-(pyridin-3-yl)thiazol-2-yl)-2-heptylbenzo[d]oxazol-5-amine;
N-(3,5-difluoro-4-octylphenyl)-4-(pyridin-3-yl)thiazol-2-amine;
N-(4-(4-chlorophenoxy)-3-(trifluoromethyl)phenyl)-5-fluoro-4-(pyridin-3-yl)thiazol-2-amine;
N-(4-(4-ethylphenoxy)-3-(trifluoromethyl)phenyl)-5-fluoro-4-(pyridin-3-yl)thiazol-2-amine;
4-(4-(5-fluoro-4-(pyridin-3-yl)thiazol-2-ylamino)-2-(trifluoromethyl)phenoxy)benzonitrile;
5-(2-(4-octyl-3-(trifluoromethyl)phenylamino)thiazol-4-yl)pyridin-2-ol;
5-(5-fluoro-2-(4-octyl-3-(trifluoromethyl)phenylamino)thiazol-4-yl)pyridin-2-ol;
N-(3-phenoxy-4-(trifluoromethyl)phenyl)-4-(pyridin-3-yl)thiazol-2-amine;
N-(4-(3-(4-chlorophenoxy)propyl)-3-(trifluoromethyl)phenyl)-4-(pyridin-3-yl)thiazol-2-amine;
N-(4-(3-(4-chlorophenoxy)propyl)-3-(trifluoromethyl)phenyl)-5-fluoro-4-(pyridin-3-yl)thiazol-2-amine;
N-(4-hexyl-3-(trifluoromethyl)phenyl)-4-(pyridin-3-yl)thiazol-2-amine;
N-(2-octylbenzofuran-5-yl)-4-(pyridin-3-yl)thiazol-2-amine;
5-fluoro-4-(pyridin-3-yl)-N-(4-(4-p-tolylbutoxy)-3-(trifluoromethyl)phenyl)thiazol-2-amine;
5-fluoro-N-(3-phenoxy-4-(trifluoromethyl)phenyl)-4-(pyridin-3-yl)thiazol-2-amine;
5-chloro-4-(pyridin-3-yl)-N-(4-(4-p-tolylbutoxy)-3-(trifluoromethyl)phenyl)thiazol-2-amine;
N-(3,5-difluoro-4-(octyloxy)phenyl)-4-(pyridin-3-yl)thiazol-2-amine;
1-(4-(4-(pyridin-3-yl)thiazol-2-ylamino)phenyl)octan-1-one;
5-fluoro-N-(4-hexyl-3-(trifluoromethyl)phenyl)-4-(pyridin-3-yl)thiazol-2-amine;
N-(2-octylbenzofuran-6-yl)-4-(pyridin-3-yl)thiazol-2-amine;
4-(6-methylpyridin-3-yl)-N-(2-octylbenzofuran-6-yl)thiazol-2-amine;
5-fluoro-4-(pyridin-3-yl)-N-(4-(4-(p-tolyloxy)butyl)-3-(trifluoromethyl)phenyl)thiazol-2-amine;
4-(pyridin-3-yl)-N-(4-(4-(p-tolyloxy)butyl)-3-(trifluoromethyl)phenyl)thiazol-2-amine;
4-(pyridin-3-yl)-N-(4-(3-(p-tolyloxy)propyl)-3-(trifluoromethyl)phenyl)thiazol-2-amine;
N-(3,5-difluoro-4-(octyloxy)phenyl)-5-fluoro-4-(pyridin-3-yl)thiazol-2-amine;
5-fluoro-2-(1-(4-(octyloxy)-3-(trifluoromethyl)phenyl)hydrazinyl)-4-(pyridin-3-yl)thiazole;
N-(4-(4-(4-(dimethylamino)phenyl)butoxy)-3-(trifluoromethyl)phenyl)-4-(pyridin-3-yl)thiazol-2-amine;
N-(2-octyl-2,3-dihydrobenzofuran-6-yl)-4-(pyridin-3-yl)thiazol-2-amine;
4-(6-methylpyridin-3-yl)-N-(2-octyl-2,3-dihydrobenzofuran-6-yl)thiazol-2-amine;
4-(pyridin-3-yl)-N-(3-(4-p-tolylbutoxy)-4-(trifluoromethyl)phenyl)thiazol-2-amine;
5-fluoro-4-(pyridin-3-yl)-N-(3-(4-p-tolylbutoxy)-4-(trifluoromethyl)phenyl)thiazol-2-amine;
5-fluoro-4-(pyridin-3-yl)-N-(3-(4-(p-tolyloxy)propyl)-3-(trifluoromethyl)phenyl)thiazol-2-amine;
5-fluoro-N-(2-octylbenzofuran-5-yl)-4-(pyridin-3-yl)thiazol-2-amine;
5-fluoro-N-(2-octyl-2,3-dihydrobenzofuran-6-yl)-4-(pyridin-3-yl)thiazol-2-amine;
1-(2-(4-chlorophenoxy)-5-(5-fluoro-4-(pyridin-3-yl)thiazol-2-ylamino)phenyl)ethanone;
1-(2-(4-ethylphenoxy)-5-(5-fluoro-4-(pyridin-3-yl)thiazol-2-ylamino)phenyl)ethanone;
N-(4-(4-phenoxybutyl)-3-(trifluoromethyl)phenyl)-4-(pyridin-3-yl)thiazol-2-amine;
4-(pyridin-3-yl)-N-(4-(4-(quinolin-3-yl)butoxy)-3-(trifluoromethyl)phenyl)thiazol-2-amine;
2-phenyl-6-(4-(pyridin-3-yl)thiazol-2-ylamino)-4H-chromen-4-one;
1-(5-(5-fluoro-4-(pyridin-3-yl)thiazol-2-ylamino)-2-(octyloxy)phenyl)ethanone;
N-(2-tert-butylbenzofuran-5-yl)-4-(pyridin-3-yl)thiazol-2-amine;
N-(3-(methylsulfonyl)-4-(octyloxy)phenyl)-4-(pyridin-3-yl)thiazol-2-amine;
5-(2-(4-(octyloxy)-3-(trifluoromethyl)phenylamino)thiazol-4-yl)pyridin-3-ol;
N-(2-phenethylbenzofuran-5-yl)-4-(pyridin-3-yl)thiazol-2-amine;

methyl 2-(octyloxy)-5-(4-(pyridin-3-yl)thiazol-2-ylamino)benzoate;
2-(octyloxy)-5-(4-(pyridin-3-yl)thiazol-2-ylamino)benzoic acid;
2-(octyloxy)-5-(4-(pyridin-3-yl)thiazol-2-ylamino)benzamide;
5-((dimethylamino)methyl)-N-(4-(octyloxy)-3-(trifluoromethyl)phenyl)-4-(pyridin-3-yl)thiazol-2-amine;
$N^4$-(5-chloro-4-(pyridin-3-yl)thiazol-2-yl)-$N^1$-methyl-$N^1$-octyl-2-(trifluoromethyl)benzene-1,4-diamine;
5-fluoro-N-methyl-N-(4-(octyloxy)-3-(trifluoromethyl)phenyl)-4-(pyridin-3-yl)thiazol-2-amine;
5-fluoro-N-methyl-N-(4-octyl-3-(trifluoromethyl)phenyl)-4-(pyridin-3-yl)thiazol-2-amine;
5-fluoro-N-(4-(4-(4-fluorophenyl)but-3-ynyloxy)-3-(trifluoromethyl)phenyl)-4-(pyridin-3-yl)thiazol-2-amine;
N-(4-(octyloxy)-3-(trifluoromethyl)phenyl)-5-(pyridin-3-yl)thiazol-2-amine;
(Z)-5-fluoro-N-(4-(oct-5-enyloxy)-3-(trifluoromethyl)phenyl)-4-(pyridin-3-yl)thiazol-2-amine;
5-fluoro-N-(4-(octyloxy)-3-(trifluoromethyl)phenyl)-4-(pyridin-4-yl)thiazol-2-amine;
5-fluoro-N-(4-octyl-3-(trifluoromethyl)phenyl)-4-(pyridin-4-yl)thiazol-2-amine;
4-(6-fluoropyridin-3-yl)-N-(4-octyl-3-(trifluoromethyl)phenyl)thiazol-2-amine;
1-(5-(5-chloro-4-(pyridin-3-yl)thiazol-2-ylamino)-2-(octyloxy)phenyl)ethanone;
N-(4-(2,3-dihydro-1H-inden-2-yloxy)-3-(trifluoromethyl)phenyl)-4-(pyridin-3-yl)thiazol-2-amine;
(Z)-5-fluoro-N-(4-(oct-3-enyloxy)-3-(trifluoromethyl)phenyl)-4-(pyridin-3-yl)thiazol-2-amine;
N-(4-(3-cyclopentylpropoxy)-3-(trifluoromethyl)phenyl)-5-fluoro-4-(6-fluoropyridin-3-yl)thiazol-2-amine;
5-fluoro-4-(6-fluoropyridin-3-yl)-N-(4-octyl-3-(trifluoromethyl)phenyl)thiazol-2-amine;
5-fluoro-4-(6-fluoropyridin-3-yl)-N-(4-(octyloxy)-3-(trifluoromethyl)phenyl)thiazol-2-amine;
N-(4-(2,3-dihydro-1H-inden-2-yloxy)-3-(trifluoromethyl)phenyl)-5-fluoro-4-(pyridin-3-yl)thiazol-2-amine;
5-(2-(4-octyl-3-(trifluoromethyl)phenylamino)thiazol-4-yl)nicotinonitrile;
5-(5-fluoro-2-(4-(octyloxy)-3-(trifluoromethyl)phenylamino)thiazol-4-yl)nicotinonitrile;
5-(5-fluoro-2-(4-octyl-3-(trifluoromethyl)phenylamino)thiazol-4-yl)nicotinonitrile;
N-(3-chloro-2-octylbenzofuran-5-yl)-4-(pyridin-3-yl)thiazol-2-amine;
N-(3-chloro-2-octylbenzofuran-5-yl)-5-fluoro-4-(pyridin-3-yl)thiazol-2-amine;
N-(4-(4-cyclopentylbutoxy)-3-(trifluoromethyl)phenyl)-5-fluoro-4-(pyridin-3-yl)thiazol-2-amine;
N-(4-(4-cyclopentylbut-3-ynyloxy)-3-(trifluoromethyl)phenyl)-5-fluoro-4-(pyridin-3-yl)thiazol-2-amine;
5-fluoro-N-(4-(5-propoxypentyl)-3-(trifluoromethyl)phenyl)-4-(pyridin-3-yl)thiazol-2-amine;
5-fluoro-4-(6-fluoropyridin-3-yl)-N-(4-octyl-3-(trifluoromethyl)phenyl)thiazol-2-amine;
5-fluoro-4-(6-fluoropyridin-3-yl)-N-(4-(octyloxy)-3-(trifluoromethyl)phenyl)thiazol-2-amine;
N-(4-(2,3-dihydro-1H-inden-2-yloxy)-3-(trifluoromethyl)phenyl)-5-fluoro-4-(pyridin-3-yl)thiazol-2-amine;
5-(2-(4-octyl-3-(trifluoromethyl)phenylamino)thiazol-4-yl)nicotinonitrile;
5-(5-fluoro-2-(4-(octyloxy)-3-(trifluoromethyl)phenylamino)thiazol-4-yl)nicotinonitrile;
5-(5-fluoro-2-(4-octyl-3-(trifluoromethyl)phenylamino)thiazol-4-yl)nicotinonitrile;
5-(2-(2-octylbenzofuran-5-ylamino)thiazol-4-yl)nicotinonitrile;
N-(3-chloro-2-octylbenzofuran-5-yl)-4-(pyridin-3-yl)thiazol-2-amine;
N-(3-chloro-2-octylbenzofuran-5-yl)-5-fluoro-4-(pyridin-3-yl)thiazol-2-amine;
N-(4-(4-cyclopentylbutoxy)-3-(trifluoromethyl)phenyl)-5-fluoro-4-(pyridin-3-yl)thiazol-2-amine;
N-(4-(4-cyclopentylbut-3-ynyloxy)-3-(trifluoromethyl)phenyl)-5-fluoro-4-(pyridin-3-yl)thiazol-2-amine;
5-fluoro-N-(4-(5-propoxypentyl)-3-(trifluoromethyl)phenyl)-4-(pyridin-3-yl)thiazol-2-amine;
1-(4-(5-fluoro-4-(pyridin-3-yl)thiazol-2-ylamino)-2-(trifluoromethyl)phenyl)octan-1-one;
N-(4-(5-(4-fluorophenyl)pentyl)-3-(trifluoromethyl)phenyl)-4-(pyridin-3-yl)thiazol-2-amine;
5-fluoro-N-(4-(5-(4-fluorophenyl)pentyl)-3-(trifluoromethyl)phenyl)-4-(pyridin-3-yl)thiazol-2-amine;
5-fluoro-N-(4-(nonan-2-yloxy)-3-(trifluoromethyl)phenyl)-4-(pyridin-3-yl)thiazol-2-amine;
5-fluoro-N-(4-(3-(pentyloxy)propyl)-3-(trifluoromethyl)phenyl)-4-(pyridin-3-yl)thiazol-2-amine;
5-fluoro-N-(4-(2-methylnonan-2-yloxy)-3-(trifluoromethyl)phenyl)-4-(pyridin-3-yl)thiazol-2-amine;
5-fluoro-N-(4-(4-propoxybut-1-ynyl)-3-(trifluoromethyl)phenyl)-4-(pyridin-3-yl)thiazol-2-amine;
$N^2$-(4-(octyloxy)-3-(trifluoromethyl)phenyl)-4-(pyridin-3-yl)thiazole-2,5-diamine;
N-(4-(5-(cyclohexyloxy)pentyl)-3-(trifluoromethyl)phenyl)-5-fluoro-4-(pyridin-3-yl)thiazol-2-amine;
5-fluoro-N-(4-(5-isopropoxypentyl)-3-(trifluoromethyl)phenyl)-4-(pyridin-3-yl)thiazol-2-amine;
5-fluoro-N-(4-(5-isobutoxypentyl)-3-(trifluoromethyl)phenyl)-4-(pyridin-3-yl)thiazol-2-amine;
N-(4-(6-ethoxyhexyl)-3-(trifluoromethyl)phenyl)-5-fluoro-4-(pyridin-3-yl)thiazol-2-amine;
N-(4-(5-(cyclopentyloxy)pentyl)-3-(trifluoromethyl)phenyl)-5-fluoro-4-(pyridin-3-yl)thiazol-2-amine; or N-(4-(8-chlorooctyl)-3-(trifluoromethyl)phenyl)-5-fluoro-4-(pyridin-3-yl)thiazol-2-amine.

25. A pharmaceutical composition comprising a compound or salt of claim 1, containing at least one pharmaceutically acceptable carrier.

* * * * *